(12) United States Patent  
Chandrasekhar

(10) Patent No.: US 8,518,324 B2
(45) Date of Patent: Aug. 27, 2013

(54) MICROWAVE REMEDIATION OF MEDICAL WASTES

(71) Applicant: Ashwin-Ushas Corporation, Inc., Marlboro, NJ (US)

(72) Inventor: Prasanna Chandrasekhar, Holmdel, NJ (US)

(73) Assignee: Ashwin-Ushas Corporation, Inc., Holmdel, NJ (US)

( * ) Notice: Subject to any disclaimer, the term of this patent is extended or adjusted under 35 U.S.C. 154(b) by 0 days.

(21) Appl. No.: 13/650,585

(22) Filed: Oct. 12, 2012

(65) Prior Publication Data

US 2013/0041041 A1 Feb. 14, 2013

Related U.S. Application Data

(62) Division of application No. 12/483,398, filed on Jun. 12, 2009, now Pat. No. 8,318,086.

(51) Int. Cl.
*A61L 2/00* (2006.01)

(52) U.S. Cl.
USPC .................................. 422/21; 502/5; 514/723

(58) Field of Classification Search
USPC ............. 422/21, 38, 291, 292, 300, 301, 307; 502/5; 514/723
See application file for complete search history.

(56) References Cited

U.S. PATENT DOCUMENTS

| | | | |
|---|---|---|---|
| 5,019,344 A | 5/1991 | Kutner | |
| 5,178,828 A | 1/1993 | Uesugi | |
| 5,223,231 A | 6/1993 | Drake | |
| 5,246,674 A | 9/1993 | Katsching | |
| 5,270,000 A | 12/1993 | Goldner | |
| 5,348,235 A | 9/1994 | Pappas | |
| 5,397,551 A | 3/1995 | Won Sam | |
| 5,403,564 A | 4/1995 | Katsching | |
| 5,407,641 A | 4/1995 | Katsching | |
| 5,413,757 A | 5/1995 | Kutner | |
| 5,429,799 A | 7/1995 | Shieh | |

(Continued)

FOREIGN PATENT DOCUMENTS

| | | |
|---|---|---|
| CA | 2073213 | 1/1994 |
| CN | 1698984 | 11/2005 |

(Continued)

OTHER PUBLICATIONS

Aracil et al., "Semi-volatile compounds from the pyrolysis and combustion of polyvinyl chloride", J. Anal. Applied Pyrolysis, 74: 465-478 (2005).

(Continued)

*Primary Examiner* — Walter D Griffin
*Assistant Examiner* — Timothy Cleveland
(74) *Attorney, Agent, or Firm* — Thomas H. Walls; Dann, Dorfman, Herrell and Skillman, P.C.

(57) ABSTRACT

Methods, devices, and remediation compositions for the microwave remediation of medical wastes are provided. The remediation compositions include a microwave active fluid including a microwave active liquid, a microwave enhancer, and a viscosity modifying agent. Methods include immersing medical waste in the remediation composition and then irradiating the medical waste and the remediation composition to remediate the medical waste. The devices include a container for the medical waste and the remediation composition, a microwave radiation source and a temperature monitoring device.

10 Claims, 22 Drawing Sheets

(56) References Cited

U.S. PATENT DOCUMENTS

| | | | |
|---|---|---|---|
| 5,552,112 A | 9/1996 | Schiffmann | |
| 5,580,521 A | 12/1996 | Gagne | |
| 5,607,612 A | 3/1997 | Held | |
| 5,609,820 A | 3/1997 | Bridges | |
| 5,641,423 A | 6/1997 | Bridges | |
| 5,645,748 A | 7/1997 | Schiffmann | |
| 5,708,259 A | 1/1998 | Shieh | |
| 5,709,842 A | 1/1998 | Held | |
| 5,759,486 A * | 6/1998 | Peterson | 422/21 |
| 5,759,488 A | 6/1998 | Eser | |
| 5,792,421 A | 8/1998 | Riley | |
| 5,811,769 A | 9/1998 | Schiffmann | |
| 5,833,922 A | 11/1998 | Held | |
| 5,837,977 A | 11/1998 | Schiffmann | |
| 5,879,643 A | 3/1999 | Katsching | |
| 5,951,947 A | 9/1999 | Hunt | |
| 5,968,400 A | 10/1999 | Wicks | |
| 6,097,015 A | 8/2000 | McCullough | |
| 6,159,422 A | 12/2000 | Graves | |
| 6,187,988 B1 * | 2/2001 | Cha | 423/235 |
| 6,245,985 B1 | 6/2001 | Sasaki | |
| 6,248,985 B1 | 6/2001 | Tomasello | |
| 6,262,405 B1 | 7/2001 | Wicks | |
| 6,280,702 B1 * | 8/2001 | Carter et al. | 424/9.1 |
| 6,344,638 B1 | 2/2002 | Tomasello | |
| 6,524,539 B1 | 2/2003 | Katsching | |
| 6,537,493 B1 | 3/2003 | Mednikov | |
| 6,646,241 B1 | 11/2003 | Varma | |
| 6,830,662 B2 | 12/2004 | Cha | |
| 7,028,623 B1 | 4/2006 | Pearson | |
| 8,318,086 B2 | 11/2012 | Chandrasekhar | |
| 2002/0068011 A1 | 6/2002 | Kongmark | |
| 2002/0189928 A1 | 12/2002 | Cha | |
| 2005/0228694 A1 | 10/2005 | Firestone et al. | |
| 2007/0072787 A1 * | 3/2007 | Hazenkamp et al. | 510/446 |
| 2007/0102279 A1 | 5/2007 | Novak | |
| 2007/0248548 A1 | 10/2007 | Blondino et al. | |

FOREIGN PATENT DOCUMENTS

| | | |
|---|---|---|
| CN | 2741684 Y | 11/2005 |
| DE | 3913472 | 10/1990 |
| DE | 3505570 | 1/1991 |
| DE | 4201491 | 7/1993 |
| EP | 0313527 | 4/1989 |
| EP | 0454122 | 10/1991 |
| EP | 1700610 | 9/2006 |
| GB | 2299271 | 2/1996 |
| GB | 2320247 | 6/1998 |
| GB | 2435039 | 8/2007 |
| JP | 3-68487 | 3/1991 |
| JP | 3068487 | 3/1991 |
| JP | 3-126462 | 5/1991 |
| JP | 30126462 | 5/1991 |
| JP | 5-15866 | 1/1993 |
| JP | 5015866 | 1/1993 |
| JP | 5-57268 | 3/1993 |
| JP | 5057268 | 3/1993 |
| JP | 5-95992 | 4/1993 |
| JP | 5095992 | 4/1993 |
| JP | 6-98930 | 4/1994 |
| JP | 6098930 | 4/1994 |
| JP | 7-47112 | 2/1995 |
| JP | 7047112 | 2/1995 |
| JP | 2001-314847 | 11/2001 |
| JP | 5-23657 | 2/2003 |
| JP | 5023657 | 2/2003 |
| JP | 2004-181022 | 7/2004 |
| JP | 2004181022 | 7/2004 |
| JP | 2004-358036 | 12/2004 |
| JP | 2006-204374 | 8/2006 |
| KR | 10-2006-0017907 | 2/2006 |
| RU | 2221592 | 1/2004 |
| WO | 94/07545 | 4/1994 |
| WO | 9514496 | 6/1995 |
| WO | 97/35623 | 10/1997 |
| WO | 01/37887 | 5/2001 |
| WO | 03/066105 | 8/2003 |

OTHER PUBLICATIONS

Bose et al., "More Chemistry for less pollution: Applications for process development", Synthesis, 11: 1578-1591 (2002).

Bose et al., "Microwave assisted synthesis of an unusual dinitro phytochemical", Tet. Lett., 45: 1179-1181 (2004).

Bose et al., "More Chemistry in a Microwave", Chemtech, 27: 18-24 (1997).

Banik et al., "Microwave Assisted Rapid and Simple Hydrogenation", J. Org. Chem., 64: 5746-5753 (1999).

Stinson Chemical & Engineering News, May 20, p. 45 (1996).

Dagawi Chemical & Engineering News, p. 26, Feb. 10, 1997.

Lattimer et a l., "Mass spectral analysis of low-temperature pyrolysis products from poly(ethylene glycol)", J. Anal. Applied Pyrolysis, 56: 61-78 (2000).

Levendis et al., "PAH and soot emissions from burning components of medical waste: examination/surgical gloves and cotton pads", Chemosphere, 42: 775-783 (2001).

Lidström et al., "Microwave Assisted Organic Synthesis—A Review", Tetrahedron, 57: 9225-9283 (2001).

Majetich et al., "The use of microwave heating to promote organic reactions", J. Microwave Power & Electromagnetic Energy, 30: 27-45 (1995).

Oda, "Dielectric processing of hazardous materials—present and future opportunities", Mat. Res. Soc. Symp. Proc., 269: 453-464 (1992).

Pramanik et al., "Microwave-enhanced enzyme reaction for protein mapping by mass spectrometry: A new approach to protein digestion in minutes", Protein Science, 11: 2676-2687 (2002).

Pramanik et al., "Rapid cyclopeptide analysis by microwave enhanced Akabori reaction", Tet. Lett., 44: 2565-2568 (2003).

Whittaker et al., "The application of microwave heating to chemical syntheses", J. Microwave Power & Electromagnetic Energy, 29: 195-219 (1994).

International Search Report and Written Opinion, dated Nov. 18, 2010 for counterpart PCT Application No. PCT/US2010/038225.

Dauerman et al., "Microwave treatment of hazardous wastes: physical chemical mechanisms", Mat. Res. Soc. Symp. Proc., 269: 465-469 (1992).

Wicks et al., "Microwave technology for waste management applications, including disposition of electronic circuitry", Microwaves III, Proc. Am. Ceramic Soc., 79 (1992).

Manhas et al., "Vinyl-b-lactams as Efficient Synthons. Eco-friendly Approaches via Microwave Assisted Reactions", Tetrahedron, 56: 5587-5601 (2000).

Form PCT/ISA/206 dated Sep. 16, 2010 for counterpart PCT Application No. PCT/US2010/038225.

* cited by examiner

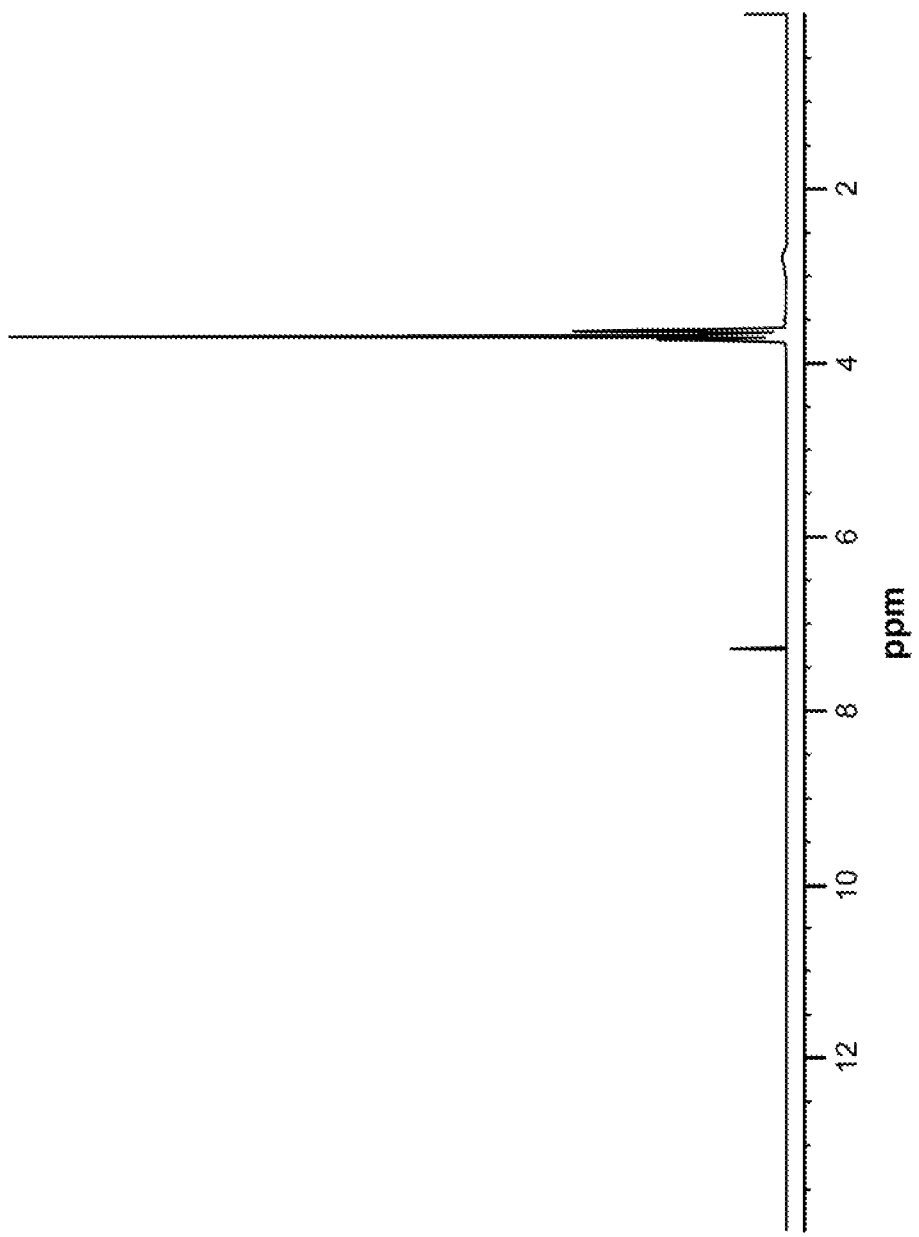

US 8,518,324 B2

MICROWAVE REMEDIATION OF MEDICAL WASTES

REFERENCE TO RELATED APPLICATIONS

This application is a divisional of U.S. patent application Ser. No. 12/483,398, filed Jun. 12, 2009, the entirety of which is incorporated herein by reference.

REFERENCE TO GOVERNMENT GRANT

This invention was supported in part by funds obtained from the U.S. Government (United States Army, Chemical and Biological Defense Division, contract number M67854-02-C-1106). The U.S. Government may have certain rights in the invention.

FIELD OF THE INVENTION

This invention relates to a method, an apparatus and chemical compositions for the microwave remediation of medical wastes.

BACKGROUND OF THE INVENTION

Medical wastes, e.g., infectious hospital medical wastes, represent a major component of hazardous wastes generated in the U.S. annually. In 2000, the U.S. generated more than 4.5 million tons of medical wastes. The method used most widely for their disposal continues to be incineration. Incineration suffers from problems of high handling, packaging and transportation costs, residual environmental pollution, high overall cost and severe local opposition. Those problems have been exacerbated by the provisions of the Clean Air Act of 1990. Alternatives to incineration, such as on-site autoclaving and shred-and-steam (with the steam generated by microwaves) suffer from similar drawbacks.

In current practice, medical wastes in hospitals, physicians' offices, medical labs, or other medical settings are currently segregated at the point of generation as "bio-medical waste", "bio-hazard (sharps)" and regular non-infective trash. Those medical wastes are then collected and transported to a centralized facility. From there, part of the medical wastes, typically about 35%, are treated by microwave-steam methods in very large, plant-like facilities set up in large, dedicated rooms or in multiple, mobile tractor-trailers (e.g. those offered by Stericycle Inc (Lake Forest, Ill.) or Sanitec Inc (Sun Valley, Calif.)). The remaining medical waste is transported off-site, frequently to another state or province, for incineration in very large incineration facilities. The entire centralized collection methodology entails a large overhead with, e.g., specialized training required for the medical waste transporters.

What current technology lacks is a relatively small-footprint, local-area, relatively portable, relatively inexpensive, point-of-service system for remediation of the medical wastes at or close to where they are generated. Current technology also lacks the ability to treat medical wastes on site in a cost-effective and facile manner.

Microwave chemistry and biology utilize microwave radiation, frequently from domestic (2.45 GHz) microwave ovens, to take the place of heat reflux or catalysts in carrying out organic and inorganic reactions. Reactions that may take days under thermal reflux at high temperatures can be completed in under an hour and sometimes in minutes under microwave radiation.

Among the requirements for a microwave version of a conventional chemical reaction is a microwave-active solvent or reactant, or both. The requirement for microwave activity is the presence of a dipole. Thus, for instance, a Cl-benzene, which has a dipole and is thus microwave active, may be substituted as a solvent for benzene, which is microwave-inactive. A key feature of microwave reactions is complete penetration and activation of the entire reaction mass from the inside of the mass. Large reaction masses are completely penetrated with microwave energy instantly, rather than being heated "from the outside", as in conventional heating, with the heat slowly penetrating to the interior. There is no "penetration depth" or "gradient". Even the strongest microwave-absorbers absorb only about 15% of the total microwave radiation, the rest passing through them. Scattering from small metal components, if present, is reabsorbed by surrounding components. Due to this feature, microwave reactions do not require stirring or mixing.

It is important to recognize that microwave chemistry is not just an alternative method of heating, although rapid and penetrating heating is one of the important effects of microwaves.

Microwave radiation causes rapid rotational and rotational/vibrational activation and relaxation at the microwave frequency, e.g. 2.45 GHz or 2.45 billion times a second. This causes microwave-induced bond cleavage and rapid bringing together of activated reaction complexes. Thus, heating is just one of several effects of microwaves.

This "not just heating" effect of microwaves has been documented in innumerable literature studies of chemical reactions. For example, there are innumerable cases of, e.g., a particular chemical reaction requiring reflux at a specific temperature for, say, 36 hours, whilst a corresponding microwave reaction, verified with fiber optic sensors to occur at the very same temperature, is complete in, say, 1 hour. If the microwave effect were a pure heating effect, then the microwave reaction would also require about 36 hours, not 1 hour. Examples of reactions for which such a direct microwave-vs.-heat comparison is available are listed in detail by Lidström et al. for more than 300 specific types of microwave reactions with specific references cited. Lidström, P.; Tierney, J.; Wathey, B.; Westman, J., "Microwave Assisted Organic Synthesis—A Review", *Tetrahedron*, 57, 9225-9283 (2001) and references therein; Majetich, G., Hicks, R., "The use of microwave heating to promote organic reactions", *J. Microwave Power & Electromagnetic Energy*, 30, 27-45 (1995); Whittaker, A. G., Mingos, D. M. P., "The application of microwave heating to chemical syntheses", *J. Microwave Power & Electromagnetic Energy*, 29, 195-219 (1994); Dauerman, L.; Windgasse, G.; Zhu, N.; He, Y., "Microwave treatment of hazardous wastes: physical chemical mechanisms", *Mat. Res. Soc. Symp. Proc.*, 269, 465-469 (1992); Wicks, G. G.; Clark, D. E.; Schulz, R. L.; Folz, D. C., "Microwave Technology for waste management applications, including disposition of electronic circuitry", *Microwaves III, Proc. Am. Ceramic Soc.* 79 (1992); and Oda, S. J., "Dielectric processing of hazardous materials—present and future opportunities", *Mat. Res. Soc. Symp. Proc.*, 269, 453-464 (1992). Some examples of these include: N-alkylation (including urea and hydrazide formation); alkylation (including C-alkylation, N-alkylation); radical Michael addition; Knoevenagel, Wittig and other condensations; cycloadditions; esterification and trans-esterification; reactions with heterocycles.

The solvent medium is an important component in microwave chemistry/biology. The presence of an efficacious microwave-active solvent can be determinative of success. It is also true to say that, in spite of extensive theoretical and experimental studies, many aspects of microwave chemistry/biology are still not completely understood. For example, it is not completely understood why certain reactions progress extremely well under microwaves while others do not. Published studies that document these issues include the following: Writeups on the work of Prof. Ajay Bose's group at Stevens Institute of Technology (Hoboken, N.J.) in: *Chemical & Engineering News*, May 20, 1996 and Feb. 10, 1997, and refs. Therein; Bose, A. K.; Banik, B. K.; Lavlinskaia, N.; Jayaraman, M.; Manhas, M. S., "MORE Chemistry in a Microwave", *Chemtech*, 27, 18-24 (1997), references cited therein; Bose, A. K.; Manhas, M. S.; Ganguly, S, N.; Sharma, A. N. and Banik, B. K. *MORE* Chemistry for less pollution: Applications for process development. *Synthesis* 2002, 11 1578-1591. Bose, A. K.; Ganguly, S, N.; Manhas, M. S.; Vidyanathan, S.; Bhattacharjee, A; Sochanchinwung, R. and Sharma, A. N. Microwave assisted synthesis of an unusual dinitro phytochemical. *Tet. Lett.*, 2004, 45, 1179-1181; Pramanik, B. N.; 1 ng, Y. H.; Bose, A. K.; Zhang, L. K.; Liu, Y. H.; Ganguly, S, N. and Bartner, P. L. Rapid cyclopeptide analysis by microwave enhanced Akabori reaction. *Tet. Lett.*, 2003, 45, 2565-2568; Pramanik, B. N.; Mirza, U. A.; Ing, Y. H.; Liu, Y. H.; Bartner, P. L.; Weber, P. C. and Bose, A. K. Microwave-enhanced enzyme reaction for protein mapping by mass spectrometry: A new approach to protein digestion in minutes. *Protein Science*, 2002, 11, 2676-2687; Manhas, M. S.; Banik, B. K.; Mathur, A.; Vincent, J. E.; Bose, A. K., "Vinyl β-Lactams as Efficient Synthons: Eco-Friendly Approaches via Microwave Assisted Reactions", in "Recent Aspects of β-Lactam Chemistry", *Tetrahedron Symposia in Print*, 56, 5587-5601 (2000); Bose, A. K.; Manhas, M. S.; Banik, B. K.; Barakat, K. J.; Wagle, D. R., "Microwave Assisted Rapid and Simple Hydrogenation", *J. Org. Chem.*, 64 (16), 5746-5753 (1999); Pramanik, B. N., Mirza, U. A., 1 ng, Y. H., Liu, Y. H., Bartner, P. L., Weber, P. C. and Bose, A. K. "Microwave-enhanced enzyme reaction for protein mapping by mass spectrometry: A new approach to protein digestion in minutes". *Protein Science*, 2002, 11, 2676-2687; Pramanik, B. N., Ing, Y. H., Bose, A. K., Zhang, L. K., Liu, Y. H., Ganguly, S, N. and Bartner, P. L "Rapid cyclopeptide analysis by microwave enhanced Akabori Reaction." *Tet. Lett.*, 2003, 44, 2565-2568.

Among theories seeking to explain the unique microwave chemistry phenomenon is one that posits that extensive rotation induced by microwaves (again, 2.45 billion times a second for 2.45 GHz microwaves) leads to greater probability of collision of reactive molecules in the precise rotational conformation required for chemical reaction to occur successfully.

Peterson (U.S. Pat. No. 5,759,486) discloses an apparatus and method for microwave sterilization of medical, surgical, veterinary and dental instruments at atmospheric pressure. The apparatus uses a microwave oven, a sterilization chemical, and water. The method requires a sterilization chemical that has a boiling point greater than 100° C., and utilizes poly(ethylene glycol) (PEG). Among the possible sterilizing chemicals cited are glycerin, propylene glycol, and di(propylene glycol). Instruments to be sterilized are placed in a tray, covered with the sterilizing chemical, the tray covered and placed in microwave oven. The tray and cover can be stainless steel, glass and microwave-transparent plastics such as polyimides. The microwave oven is activated for 4 to 5 minutes. The sterilizing chemical is drained and sterile water then used to wash the instruments. The method requires the separate production of sterile water by distillation of the rinsates.

Cha (U.S. Pat. No. 6,830,662) discloses a process for microwave destruction of harmful substances such as chemical and biological warfare ("CW" and "BW") agents as well as certain types of biological wastes such as animal remains. Acetonitrile is utilized as an example of a chemical agent that is related to a class of cyanide containing CW agents. Acetonitrile gas is passed over a carbonaceous bed containing a silica-based oxidation catalyst mixed with SiC particles. Upon directing 400 watts of 2.45 GHz microwave power at the bed, "complete destruction" of the acetonitrile is noted. In a typical, similar application to pyrolysis of solid medical waste, a two-stage reactor having carbonaceous beds is employed. In another application, sterilization of an *Escherichia coli* culture flowing over a bed of activated carbon, while subject to the same microwave power, was achieved rapidly.

Mednikov (U.S. Pat. No. 6,537,493) discloses an apparatus for microwave sterilization of wastes. The key feature of this invention is circular waveguides directing 2.45 GHz microwaves from opposite directions into a sterilization chamber where they "collide". The invention uses a pressure-retaining, hermetically sealable sterilization chamber. Microwaves are used to generate steam from a liquid reservoir substantially within the chamber.

Schiffmann et al. (U.S. Pat. No. 5,811,769, U.S. Pat. No. 5,645,748 and U.S. Pat. No. 5,552,112) disclose a sterilization method and system that uses a container for containing metallic medical instruments while being subjected to microwave radiation. An enclosed outer space having a microwave-active layer is used to generate heat, which raises the temperature of an enclosed inner space sufficient for sterilization. The invention does not use water/steam, but rather relies on the maintenance of a temperature of at least 204.4° C. (400° F.) for a period of time sufficient for sterilization. Schifmann et al. (U.S. Pat. No. 5,837,977) describe a heating container with a microwave-reflective dummy load, in which a reflective inner container is contained within a microwave-transparent outer container, for use in a sterilization apparatus.

Other examples of methods and systems for remediation of medical waste include Tomasiello (U.S. Pat. No. 6,344,638 and U.S. Pat. No. 6,245,985), Held et al. (U.S. Pat. No. 5,833,922 and U.S. Pat. No. 5,709,842), Bridges et al. (U.S. Pat. No. 5,641,423 and U.S. Pat. No. 5,609,820), Held et al. (U.S. Pat. No. 5,607,612), Goldner et al. (U.S. Pat. No. 5,270,000), Katschnig et al. (U.S. Pat. Nos. 6,524,539, 5,879,643, 5,403,564, 5,407,641 and 5,246,674), Goldner (German Pat specification 3,505,570), McCullough et al. (U.S. Pat. No. 6,097,015), Wicks et al. (U.S. Pat. No. 6,262,405 and U.S. Pat. No. 5,968,400), Kutner et al. (U.S. Pat. No. 5,413,757 and U.S. Pat. No. 5,019,344), Riley (U.S. Pat. No. 5,792,421), Graves et al. (U.S. Pat. No. 6,159,422), Eser et al. (U.S. Pat. No. 5,759,488), Pearson (U.S. Pat. No. 7,028,623), Pappas (U.S. Pat. No. 5,348,235), Drake (U.S. Pat. No. 5,223,231), Varma et al. (U.S. Pat. No. 6,646,241), Uesugi (U.S. Pat. No. 5,178,828), Shieh et al. (U.S. Pat. No. 5,708,259 and U.S. Pat. No. 5,429,799), Kawashima et al. (Japanese Pat specification No. 6098930), Kamata et al. (Japanese Pat specification 7047112), Fukui et al, (Japanese Pat specification 5095992), Kameda et al. (Japanese Pat specification 5023657, Japanese Pat specification 5015866, and Japanese Pat specification 5057268), Terayama et al. (Japanese Pat specification No. 2001-314847), Kawahara et al. (Japanese Pat specification 2004-358036), Takahashi et al. (Japanese Pat specification No. 2004-181022), Kunieda et al. (Japanese Pat specification No. 2006-204374), Nakajima (Japanese Pat specification No. 3126462), Mori et al. (Japanese Pat specification No. 3068487), Won Sam (U.S. Pat. No. 5,397,551 and Canadian Pat No. 2,073,213), Schiller (German Pat specification No. 4,201,491), Marshall et al. (PCT application WO95/14,496), Hunt (U.S. Pat. No. 5,951,947), Langenegger (British Pat specification No. 2,320,247), Podzorova et al. (Russian Pat specification No. 2,221,592), Tang et al. (Chinese Pat. specification 2741684Y), Zhang et al. (Chinese Pat specification 1698984), Sin(Korean Pat specification 2006-0017907), Novak (U.S. Pat App. Pub. No. 2007/0102279 and British Pat specification No. 2,435,039), Pilema (German Pat No. 3,913,472).

However, there is still a need for a simple, inexpensive, ambient-pressure, environmentally benign, non-toxic, low-power, point-of-service method and apparatus for remediation of medical waste at or close to the point of its generation, and its further rendition into unrecognizable medical wastes suitable for disposal as ordinary refuse or "Class 10 municipal medical waste". Thus, it is an object of the invention to provide a simple, inexpensive, ambient-pressure, environmentally benign, non-toxic, low-power, point-of-service method and apparatus for remediation of medical waste at or close to the point of its generation, and its further rendition into unrecognizable medical wastes suitable for disposal as ordinary refuse or "Class 10 municipal medical waste".

SUMMARY OF THE INVENTION

A microwave-active fluid ("MAF") composition for medical waste remediation is provided. The MAF includes a microwave active liquid ("MAL") having a boiling point from about 150° C. to about 300° C., a microwave enhancer, and a viscosity modifying agent which modifies the viscosity of the microwave active liquid. The rotational excitation of microwaves causes a breakdown in the tertiary and quaternary structure of proteins (including such elements as specific H-bonds). Microwaves thus cause rapid breakdown and denaturing of proteins, thus killing individual organisms, be they bacteria or viruses. Furthermore, the deep and instant penetration of the reaction mass by microwaves facilitates access to bacteria or viruses that may be lodged in parts of amorphous wastes that are otherwise inaccessible to methods such as standard autoclaving or heat sterilization, unless these are carried out for extended lengths of time. In summary, microwaves achieve sterilization of wastes with a combination of the dual effects of heating (i.e., temperature) and the microwave-induced bond-cleavage (denaturing effect).

The invention is further directed to a method for preparing the microwave active liquid composition for medical waste remediation comprising the steps of:

(a) mixing a viscosity modifying agent into a microwave active liquid (MAL) having a boiling point from about 150° C. to about 300° C. to form a solution, while maintaining the temperature of the solution at about 100° C. to about 150° C. during mixing to form a solution;

(b) cooling the solution of (a) to less than about 30° C. to form a gel comprising the microwave active liquid;

(c) adding a microwave enhancer to the microwave active liquid in the gel of (b) under conditions sufficient to form a sol;

(d) cooling the sol of (c) to at least 30° C. for a time sufficient for any unincorporated microwave enhancer to separate from said sol;

(e) irradiating the cooled sol of (d) under conditions sufficient to heat the sol to at least about 150° C.;

(f) cooling the irradiated sol of (e) to at least about 100° C.;

(g) optionally repeating steps (e) and (f) at least one time;

(h) irradiating the cooled sol of (d) under conditions sufficient to heat the sol to at least about 150° C.;

(i) cooling the irradiated sol of (h) to less than about 3° C. to form a gel and (j) isolating the gel formed in (i) to yield the microwave active liquid composition for medical waste remediation.

Alternatively, the method for preparing a composition for medical waste remediation, a microwave active fluid, includes mixing a viscosity modifying agent into a MAL having a boiling point from about 150° C. to about 300° C. to form a solution, while maintaining a temperature of about 100° C. to about 150° C. during mixing. The solution is cooled to less than about 30° C. where it forms a gel. A microwave enhancer is mixed into the gel to form a sol. A dispersing agent is added to the sol and the sol/dispersing agent mixture is milled. The sol is separated from the dispersing agent to form the medical waste remediation composition.

A method for microwave irradiation of medical waste is also provided. The method includes placing the medical waste in a microwave-transparent container. A remediation composition is added to the container in a quantity sufficient to immerse the medical waste therein. The remediation composition includes a microwave-active fluid including a microwave active liquid having a boiling point from about 150° C. to about 300° C., a microwave enhancer, and a viscosity modifying agent. The container with the medical waste immersed in the remediation composition is irradiated for a time sufficient to remediate the medical waste.

A system for medical waste remediation is provided. The system includes a container and a container lid. The system also includes a waste receptacle for holding medical waste. The waste receptacle allows the medical waste to be immersed in a remediation composition, and is sized to fit in the container. The remediation composition includes a microwave-active fluid including a microwave active liquid having a boiling point from about 150° C. to about 300° C., a microwave enhancer, and a viscosity modifying agent. The system also includes a temperature probe for measuring the temperature of the remediation composition, and a microwave oven for irradiating the medical waste and the remediation composition.

A device for medical waste remediation utilizing microwave radiation is provided. The device includes a housing including a remediation chamber having an aperture, a remediation chamber closure for placement on the aperture of the remediation chamber; a rotatable cutter assembly for cutting waste in the remediation chamber; a motor driving the cutter assembly and a magnetron for delivering microwave radiation into the remediation chamber. The device also includes a first waste receptacle, a reservoir for containing a remediation composition, a pump, and a controller. The first waste receptacle is sized to fit within the remediation chamber. The reservoir is in fluid communication with the remediation chamber. The pump is in fluid communication with the reservoir and the remediation chamber, and transfers the remediation composition from the reservoir to the remediation chamber. The controller controls the device and is in communication with the motor, the cutter assembly, the magnetron, and the pump.

Another device for medical waste remediation utilizing microwave radiation is provided. The device includes a first chamber and a remediation chamber. The first chamber includes an opening for introducing medical waste and at least one grinder for grinding the medical waste. The remediation chamber is in fluid communication with the first chamber, and includes a drain for draining a microwave active fluid for remediating the medical waste. The device also includes at least one magnetron for delivering microwave radiation to at least the remediation chamber, at least one motor for driving the grinder, and a fluid reservoir for housing the microwave active fluid. The fluid reservoir is in fluid communication with at least the remediation chamber.

Yet another device for medical waste remediation utilizing microwave radiation is provided. This device comprises:

a housing including a remediation chamber having a bottom with an adjustable opening; a remediation chamber top assembly, the assembly comprising a chamber top including an opening therethrough and a rotatable cutter and piston assembly extending through the opening; a motor in communication with a means to rotate a first waste receptacle and in communication with the cutter and piston assembly; a magnetron;

a waveguide to direct microwave radiation from the magnetron into the remediation chamber;

a first waste receptacle sized to fit within the remediation chamber, the first waste receptacle having a plurality of openings therein, the first waste receptacle adapted for at least a portion of the chamber top; the chamber top adapted for covering the first waste receptacle;

a reservoir to contain a remediation composition, the reservoir in fluid communication with the remediation chamber;

a pump to transfer the remediation composition between the reservoir and the first waste receptacle;

a second waste receptacle, the second waste receptacle positioned adjacent the first waste receptacle wherein the adjustable opening is adapted for transfer of medical waste from the first waste receptacle to the second waste receptacle, and wherein the second waste receptacle further comprises a grinder and shredder for reducing the size of the medical waste after microwave irradiation thereof;

a controller attached to the housing and in communication with the motor, the cutter and piston assembly, the magnetron, the waste receptacles, the pump, and the adjustable opening;

a temperature probe, the temperature probe being in communication with the first waste receptacle and the controller; and a liquid sensor for determining the liquid content of the medical waste in the first waste receptacle, the liquid sensor being in communication with the controller.

Another device for medical waste remediation utilizing microwave radiation comprises:

a first chamber comprising a means for introducing medical waste and at least one grinder for grinding the medical waste;

a remediation chamber in fluid communication with a first chamber, the remediation chamber optionally comprising a drain for draining a microwave active fluid for remediating the medical waste;

at least one magnetron for delivering microwave radiation to at least the remediation chamber;

at least one motor for driving the grinder; and a fluid reservoir for housing the microwave active fluid, the fluid reservoir in fluid communication with at least the remediation chamber.

Yet another device for medical waste remediation utilizing microwave radiation encompassed by the invention comprises a device for medical waste remediation utilizing microwave radiation, the device comprising:

a first chamber comprising a means for introducing medical waste, at least one rotatable cutter assembly for cutting medical waste in said first chamber, a means for directing said medical waste to said rotatable cutter assembly and floor for directing said medical waste to a remediation chamber;

a remediation chamber which is in fluid communication with said first chamber, said remediation chamber comprising a waste receptacle and a cooling supply for cooling fluid in said remediation chamber;

a fluid permeable layer separating the first chamber from the second chamber;

a reservoir in fluid communication with the remediation chamber, said remediation chamber comprising a drain for draining a microwave active fluid for remediating medical waste;

at least one motor driving the rotatable cutter assembly;

at least one means (e.g., a magnetron) for delivering microwave radiation to at least the remediation chamber and at least one motor driving the cooling supply for cooling fluid in said remediation chamber.

A method for medical waste remediation using a device of the present invention is provided. The method includes loading the medical waste into a first waste receptacle and then loading the first waste receptacle into a remediation chamber of a housing. The housing includes the remediation chamber having an aperture, a remediation chamber assembly for placement on the remediation chamber, a motor driving a cutter assembly and a magnetron for delivering microwave radiation into the remediation chamber. The medical waste is immersed in a remediation composition in the first waste receptacle. Microwave radiation from the magnetron is delivered to irradiate the medical waste for a time sufficient to remediate the medical waste. The remediation composition is drained from the first waste receptacle and the remediation chamber and may be transferred from the first waste receptacle to a second waste receptacle for disposal. In a particular embodiment, the size of the medical waste may be reduced anytime after loading the medical waste into the first waste receptacle and before transferring the waste from the first waste receptacle to a second waste receptacle. Alternatively, the irradiated medical waste is transferred to a second waste receptacle where the size of the irradiated medical waste is reduced. The size of the medical waste may be reduced by shredding and grinding and optionally cutting and/or compacting.

BRIEF DESCRIPTION OF THE DRAWINGS

For the purpose of illustrating the invention there is shown in the drawings various forms, which are presently preferred; it being understood, however, that this invention is not limited to the precise arrangements and instrumentalities particularly shown.

FIG. 14(a) shows a proton spectrum for pure PEG.

DETAILED DESCRIPTION OF THE INVENTION

Figure 1:
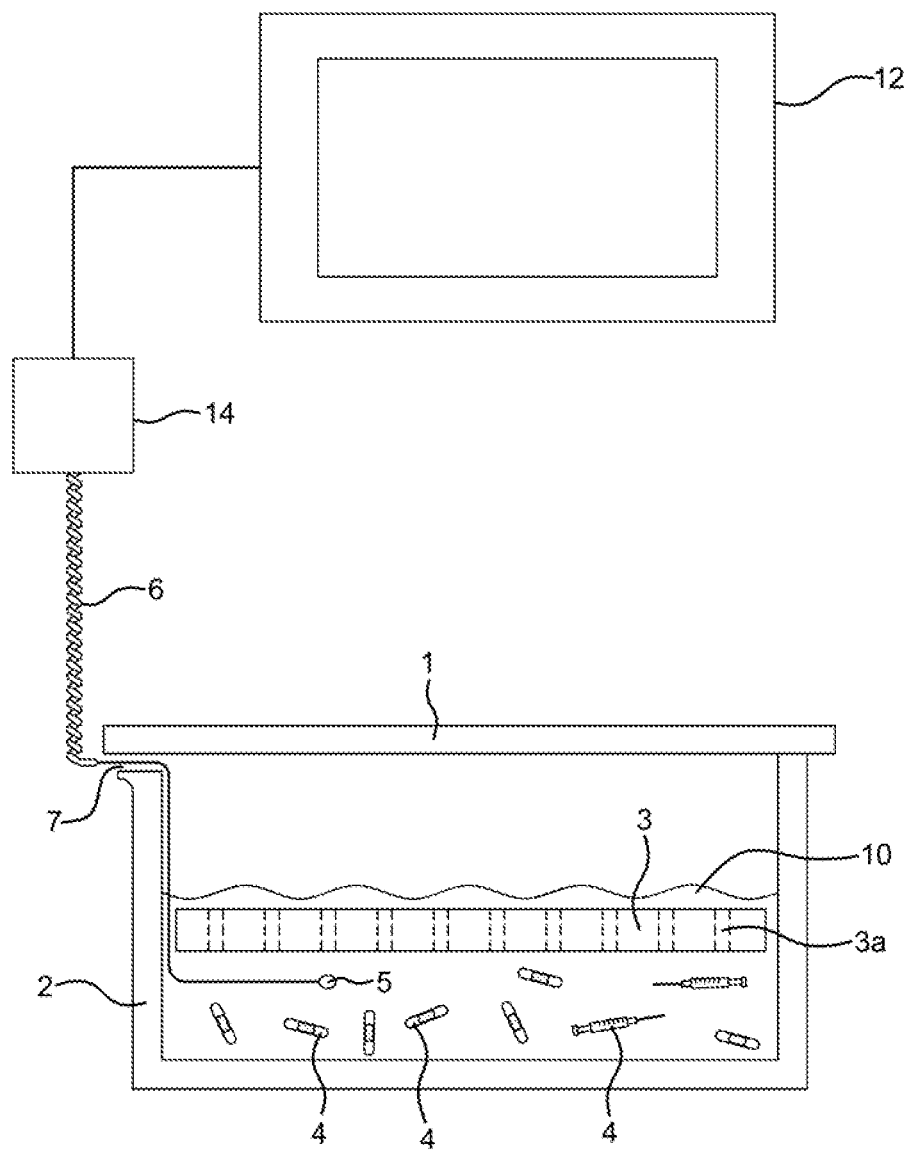
FIG. 1 is a schematic view of an apparatus for microwave treatment of medical waste.

While the compositions, methods and devices heretofore are susceptible to various modifications and alternative forms, exemplary embodiments will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

Unless defined otherwise, all technical and scientific terms used herein have the same meaning as commonly understood by one of ordinary skill in the relevant art. Although any methods and materials similar or equivalent to those described herein can also be used, the preferred methods and materials are now described.

A microwave-active fluid (MAF) composition for remediation of medical waste is provided. As used herein, "medical waste" includes, but is not limited to, medical, hospital, biological, and other related wastes. For example, medical waste includes, but is not limited to, any of the following or combinations thereof: gloves, cotton swabs, bandages, pads, tapes, tissues and culture dishes, partly or substantially infected and/or contaminated. Medical waste also includes metallic "sharps", including needles, syringes, scalpels, suture tools, other disposable surgical tools, blades and glass items, again partly or substantially infected and/or contaminated; cultures/stocks of infectious agents; blood and blood products; pathological wastes; bodily fluids and related liquid wastes, whether contaminating items such as cotton bandages or present alone; and animal waste. Liquid wastes generally make up less than about 5 wt. % (weight/weight) of medical wastes. However, medical wastes as used herein are not limited to those percentages. That is, medical wastes as used herein includes compositions having less than about 5 wt. % liquid waste, compositions having about 5 wt. % liquid waste, and compositions having greater than about 5 wt. % medical waste. Preferably, metallic sharps make up less than about 25 wt. % of the medical waste, and more preferably less than about 20 wt. % of the medical waste.

Medical waste is immersed in the MAF and both the medical waste and MAF are exposed to microwave radiation to remediate the medical waste. As used herein, "remediate" means sterilizing and chemically breaking down (e.g., breaking down protein structures) of material such that biological activity of pathogens and other microbes is inhibited or terminated. As used herein, "microwave radiation" includes radio-frequency radiation in the range from about 0.3 to about 300 GHz. Preferably the radio-frequency radiation is from about 0.4 to about 6 GHz. This preferred range includes the common microwave frequencies employed in heating, 0.915 GHz for industrial applications and 2.45 GHz for domestic (e.g. kitchen) applications.

The medical waste can be placed in a microwave-transparent container to which a remediation composition can be added in a quantity sufficient to immerse the medical waste therein. The remediation composition includes an MAF including a microwave active liquid ("MAL"), a microwave enhancer, and a viscosity modifying agent. The MAL, the microwave enhancer, and the viscosity modifying agent are combined to form the MAF. The medical waste immersed in the remediation composition may be covered with a microwave-transparent weight. Alternatively, the microwave-transparent weight can be placed on the medical waste before the medical waste is immersed in the remediation composition. A microwave-transparent lid is place onto the container and the container with the immersed medical waste is placed into a device that generates microwaves. The device is activated to irradiate the immersed medical waste for a time period sufficient to remediate the medical waste.

A temperature probe can be inserted into the remediation composition to monitor the temperature of the remediation composition before, during and/or after irradiation.

The irradiation step can be continuous or intermittent. Preferably, the total irradiation time (including any pauses in the irradiation cycle) is less than about 240 minutes. More preferably, the total irradiation time is from 5 minutes to about 60 minutes.

Without wishing to be bound by any theory, it is believed that effectiveness of the MAF in remediating the medical waste can be ascribed, at least in part, to the rotational excitation caused by microwave radiation, which results in a breakdown in the tertiary and quaternary structure of proteins (including such elements as specific H-bonds). Microwave radiation causes rapid breakdown and denaturing of proteins, thus killing individual organisms such as bacteria or viruses. The deep and instant penetration of the reaction mass by microwave radiation also facilitates access to individual organisms such as bacteria or viruses that may be lodged in parts of amorphous medical wastes that are otherwise inaccessible to methods such as standard autoclaving or heat sterilization, unless these are carried out for extended lengths of time. As a result, microwave radiation, as described herein can achieve remediation of medical wastes with a combination of the dual effects of heating (i.e., temperature) and the microwave-induced bond-cleavage (denaturing) effect of the radiation on the medical waste.

The MALs selected for the MAF of the present invention have a boiling point from about 150° C. to about 300° C. Preferably, the boiling point is from about 210° C. to about 285° C. Preferably, the MALs have a high microwave activity. As used herein with respect to MALs, "high microwave activity" means exhibiting a temperature rise under microwave irradiation, for a given volume and irradiation time, of at least about 1.5 times and preferably greater than about 2 times that of water. Preferably, the MALs are non-toxic and environmentally benign and do not generate significant toxic, hazardous or gaseous products, upon microwave irradiation, and resultant heating up to their boiling point. Preferably, the MALs are water-soluble. Preferably, the MALs have an ability to retain solid microwave enhancers such as activated carbon, SiC and $Fe_3O_4$ as a stable sol or gel with or without the assistance of a viscosity modifying agent (e.g., an emulsifying, gelling or sol-stabilizing agent).

Preferred MALs that satisfy the above criteria include the family of poly(glycols), such as poly(ethylene glycol) (PEG) and poly(propylene glycol) (PPG) of all molecular weights. The MAL can be glycerol and its acid esters, such as glycerol monostearate and glycerol lactate, and combinations thereof. The MALs can be a combination of different liquids. For example, the MALs can be a combination of different poly (glycols).

Other potential MALs, such as di(ethylene glycol), di(propylene glycol) and triethanolamine, which all possess microwave activity, do not fulfill the above requirements. Most notably those potential MALs lack non-toxicity and high microwave activity.

In one embodiment, the MAL is PEG having a molecular weight, $M_n$, less than about 420, and preferably from about 200 and about 420, where it remains a liquid. At $M_n$ above about 420, PEG generally is a highly viscous liquid and at $M_n$ significantly above 420, PEG is a waxy solid. Highly viscous and waxy solid PEGs are generally not preferred in this invention.

PEG also has relatively low thermal and electrical conductivity when compared to those properties of water. The low electrical conductivity aids in eliminating any arcing effect (i.e., electrical current flowing through normally nonconductive material such as air) of thin metal films in the immersed medical wastes. As long as metallic medical wastes remain immersed in PEG, no arcing is observed during the microwave process. Metallic films, which may be present in medical waste, include, but are not limited to, films on metalized plastic, films on compact discs, and the like. The low thermal conductivity of PEG minimizes heat transfer to the container or outer vessels while maximizing the "temperature effect" component of the remediation mechanism (i.e., the remediation of the medical waste through exposure to high temperatures).

PEG and other poly(glycols) are water-rinsable and have rinsates that are benign and are disposed of readily. The presence of small amounts, less than about 10 v/v % (volume/volume), of water or aqueous solutions in the poly(glycols) does not significantly affect their remediation properties. PEG and other poly(glycols) are also inexpensive.

When irradiated with microwave radiation, the MAL can aid in remediating medical waste immersed therein in two ways. First, when irradiated, the MAL heats up, thereby exposing the medical waste to increased temperatures. Second, when irradiated, the MAL exhibits denaturing properties that allow the irradiated MAL to break down proteins and chemical bonds in other biological molecules in the medical waste.

The MAF also includes one or more microwave enhancers. The microwave enhancers contribute to the heating of the MAF, thereby contributing to the heating portion of the dual microwave effect (heating effect combined with the microwave-induced chemical bond-cleavage effect) which aides in the remediation of medical wastes. Microwave enhancers preferably have a high microwave-activity. As used herein with respect to microwave enhancers, "high microwave activity" means exhibiting a temperature rise under microwave irradiation, for a given weight and irradiation time of at least about 1.5 times and preferably greater than about 2 times that of water. Preferably, the microwave enhancers are non-toxic and environmentally benign and do not, upon microwave irradiation, generate toxic, hazardous or gaseous products.

Microwave enhancers include solids having significant microwave activity due to the presence of strong dipoles. The microwave enhancers include meso-, micro- or nano-particulate microwave-active solids. Among these are materials such as SiC, $Fe_3O_4$ and activated carbon. In a particular embodiment, the activated carbon is a decolorizing activated charcoal. The microwave enhancer may be activated carbon, SiC, $Fe_3O_4$ or any combination thereof. Preferably, the microwave enhancer is activated carbon.

Activated carbon is believed to derive its polarity from adsorbed impurities. Activated carbon includes, but is not limited to, the following commercially available varieties: decolorizing activated charcoal; activated carbon, granular, mesh 2 to 150 and (−)100 mesh; carbon nanopowder, amorphous. SiC may include, but is not limited to, the following commercially available varieties: (−)400 mesh; 100 to 450 mesh; and nanopowder. $Fe_3O_4$ may include, but is not limited to, the following commercially available varieties: powder, average particle size 5 microns; and nanopowder, particle size 20 to 30 nm.

SiC is a refractory material used in microwave instrumentation such as pyrolyzers and ashing systems, e.g. those manufactured by Milestone, Inc., Shelton, Conn. and others. As an illustration of the microwave absorption properties of SiC, 2 g of SiC (mesh size −400) placed at the midpoint of the platen in a 1.2 KW oven such as a Sears KENMORE® microwave oven (Model 721.62461, 1.2 KW, 2.45 GHz, 13.5 Amp) irradiated for 10 minutes achieves a temperature of over 1000° C. Activated carbon and $Fe_3O_4$ have somewhat smaller temperature effects, i.e. achieve somewhat lower temperatures under identical conditions. It should be appreciated that the temperature achieved by irradiating the microwave enhancer is simply a measure of the microwave activity of the material. Besides their microwave activity, SiC, $Fe_3O_4$ and activated carbon also possess other advantageous properties, such as non-toxicity, environmental benignness and fair chemical inertness.

The microwave enhancer can be from about 0.25 wt. % to about 5 wt. % of the MAF. Preferably, the microwave enhancer is from about 0.5 wt. % to about 2 wt. % of the MAF.

The MAF also includes one or more viscosity modifying agents. The viscosity modifying agents assist in incorporating the microwave enhancers into the MAL such that a milk-like sol results. Viscosity modifying agents are soluble in the selected MAL. Preferably, the viscosity modifying agents have a sol-forming ability in the MALs. Preferably, the viscosity modifying agents have an ability to act as gelling agent and/or emulsifier for the microwave enhancers.

Viscosity modifying agents include, for example, gelling agents, emulsifiers and stabilizers of the MAL. In one embodiment, the viscosity modifying agent is poly(ethylene oxide) (PEO), of average molecular weight, $M_v$, 100,000 to 8,000,000. Other potential gelling agents, such as, by way of example, poly(vinyl alcohol) (PVA), do not fulfill the requirement of solubility and gelling capability.

In one embodiment, the viscosity modifying agent includes PEO of $M_v$, 100,000 to 500,000. In another embodiment the viscosity modifying agent includes PEO of $M_v$, 200,000, at a concentration of about 1 wt. % in the MAF.

The viscosity modifying agent can be from about 0.01 wt. % to about 5 wt. % of the MAF. Preferably, the viscosity modifying agent is from about 0.1 wt. % to about 1 wt. % of the MAF.

In a particular embodiment, the viscosity modifying agent is soluble in microwave active liquid. An example is PEO. In one embodiment, where PEO is the viscosity modifying agent and PEG is the MAL, the PEO, at concentrations from 0.01 wt. % to 5 wt. %, acts as a sol-stabilizing agent to a stable sol in the PEG. PEO is transparent to microwaves, i.e. microwave-inactive. PEO also aids in the rendering into sols in PEG of microwave enhancers such as SiC, activated carbon and $Fe_3O_4$, materials that would normally simply precipitate out of the PEG. Sols of activated carbon (1% w/w) and PEO (1% w/w) in PEG can maintain their stability and milk-like homogeneity over extended periods, for example, up to about eight months.

Preferred components of the MAF, such as PEG, PEO, SiC, activated carbon and $Fe_3O_4$, are generally environmentally benign, non-toxic and chemical inert. PEG is listed in the Merck Index as a food additive. PEG at an $M_n$ of about 285 to about 315 has a boiling point at about 270° C., which precludes the production of vapors, harmful or otherwise, from both the PEG itself and any medical wastes immersed in the PEG during the heating that occurs during microwaving.

The MAF can be prepared by first dissolving a viscosity modifying agent such as PEO into a MAL such as PEG to form a solution, while mixing the solution and maintaining the temperature of the solution at about 100° C. to about 15° C. The solution can be cooled to less than about 50° C., preferably less than about 30° C., and most preferably from about 15° C. to about 30° C. to form a gel. A microwave enhancer can then be mixed into the gel to form a sol.

Preferably, when the microwave enhancer added the gel, it is first mixed with the gel for greater than about 10 minutes. More preferably, the mixing time is greater than about 30 minutes. Most preferably, the mixing time is greater than about 60 minutes. In one embodiment, the mixing time is from about 60 minutes to about 90 minutes. In another embodiment, the mixing time is from about 60 minutes to about 120 minutes. The mixing can be continuous or intermittent. The mixing can be performed by standard mixing techniques such as stirring with a magnetic stir bar. Mixing is performed at a temperature ranging from 90° C.-130° C. and preferably at about 100° C.

The mixture may then be cooled to less than about 20° C. to about 40° C. and preferably about 30° C. after mixing for a time sufficient to separate any unreacted microwave enhancer from the sol, for example, from about three hours to about 16 hours. The cooled sol is then irradiated (e.g., microwave) under conditions sufficient to heat the sol to at least about 150° C. and preferably between about 150° C.-250° C. The irradiated sol is cooled to at least about 100° C. and preferably between about 50° C. to about 100° C. The irradiation and cooling steps may be repeated at least once and may be repeated up to 20 times. The cooled sol is then irradiated under conditions sufficient to heat the sol to at least 150° C. and preferably between about 150° C.-250° C. The irradiated sol is cooled to less than about 30° C. to form a gel. The gel formed is isolated, by, for example, decantation to separate from unreacted solid microwave enhancer. This solid microwave enhancer is removed and microwave active liquid composition for medical waste remediation is obtained.

A dispersing agent may be optionally added to the sol to act as a milling agent. The sol/dispersing agent mixture can be milled and then the sol separated from the dispersing agent to yield a composition for medical waste remediation, i.e., the MAF. The dispersing agent, if employed, preferably is added to the sol at a concentration from about 30 v/v % to about 70 v/v % of the sol. More preferably, the dispersing agent is added to the sol to a concentration from about 40 v/v % to about 60 v/v %. Most preferably, the dispersing agent is added to a concentration of about 50 v/v %.

The sol containing the dispersing agents can be milled in a standard jar, or ball mill, for example. The milling time is preferably at least about 5 minutes, more preferably at least about 10 minutes, and most preferably at least about 30 minutes. Preferably, the milling time is less than about 120 minutes. More preferably, the milling time is less than about 60 minutes. Most preferably, the milling time is from about 30 minutes to about 60 minutes. The milling can be continuous or intermittent. The milling can be performed by standard milling techniques.

In one embodiment, the sol containing the dispersing agents is milled from about 10 minutes to about 60 minutes. The resultant sol is decanted to separate the sol from the dispersing agents. The dispersing agents can be washed with water for reuse. The decanting produces a gel or sol of the microwave enhancer in the solution of the viscosity modifying agent (i.e., sol-stabilizer) in the MAL, i.e. it yields the MAF.

In one embodiment of preparing the MAF, about 0.01 to about 5 wt. % of PEO is dissolved with stirring at about 100° C. to about 150° C., in PEG of $M_n$ about 200 to about 415 for about 1 hour. In another embodiment, about 1 wt. % PEO of $M_v$ about 200,000 can be dissolved with stirring at 100° C. to 150° C., in PEG of $M_n$ about 200 to about 415 for about 1 hour.

Preferably, the PEG/PEO solution is allowed to cool to less than about 50° C., more preferably to less than about 30° C., and most preferably to room temperature (i.e., about 25° C.) to form a gel. The solution can be stirred during cooling and then allowed to stand after the cooling is complete. The solution can be capped or covered. If allowed to stand, the gel is preferably mixed before the microwave enhancer is added to the gel to form a sol. Preferably, the microwave enhancer is added at a concentration of about 0.01 to about 5.0 wt. %, more preferably at a concentration of about 0.1 to about 1.0 wt. %, and most preferably at a concentration of about 0.5 wt. % of the sol.

In one embodiment of the present invention, the dispersing agent added to the sol comprises spherical or partially spherical solid or hollow objects. The objects can be one or more of glass beads or balls, ceramic beads or balls, metal beads or balls, or stainless steel beads or balls, for example. Preferably, the objects have a diameter from about 0.1 mm to about 20 mm, more preferably from about 0.1 mm to about 10 mm, and most preferably from about 2 mm to about 4 mm. Preferably, the objects are added to the sol at an amount from about 30 to about 70 v/v % of the sol, more preferably about 40 to about 60 v/v %, and most preferably about 50 v/v %.

The MAF is effective in remediating bacteria-infected medical wastes and medical wastes infected with other biological molecules. It is believed that the MAF is also effective in remediating virus-infected medical waste.

What follows is a discussion of a device and method with reference to the drawings, where like numerals identify like elements. There is shown in FIG. 1 an embodiment of a system for microwave remediation of medical waste. The system is considered to be a "manual" or "laboratory test" system; and generally used for testing the efficacy of various MAF formulations, but the embodiment is not limited to that use. The system includes a vessel 2 containing medical waste 4, and an MAF composition 10.

Preferably, the vessel 2 is made of microwave-transparent material. As used herein, "microwave-transparent materials" are "low-loss materials" in microwave parlance. They are characterized by low value of microwave extinction parameter "E". Microwave-transparent materials include materials that are microwave transparent and materials that are substantially microwave transparent. Examples of microwave-transparent materials include borosilicate glass, PTFE ((polytetrafluoroethylene, sold under the trademark TEFLON®, DuPont Corporation, Wilmington Del.), poly(imide) (PI) or poly(ether imide) (PEI). In addition to the microwave transparency of PTFE, PI and PEI, those materials also have an ability to withstand high temperatures. PTFE, PI and PEI withstand maximum MAF temperatures of 240 to 300° C., which may be achieved practicing the medical waste remediation methods described herein. PTFE, PI and PEI and are substantially chemically inert to substances generally found in medical wastes.

The medical waste 4 may be retained by a weight 3 to insure that the medical waste 4 is immersed in the MAF composition 10. As shown in FIG. 1, the MAF composition 10 is added so that the fluid level is above the level of the weight 3. The weight 3 can be made of PTFE or other microwave-transparent materials. The weight can be of a thickness and density that allows the weight 3 to weigh down the medical waste 4 within the MAF composition 10, while allowing for circulation of the MAF composition 10 within the vessel 2. The weight 3 can include perforations or holes 3a to allow flow of the MAF composition 10 within the vessel 2, and which can ease the submersion of the weight 3 in the MAF composition 10.

The vessel 2 is covered with a lid 1, preferably made of the same material as the vessel 2. The lid 1 can be, for example, about 1 to about 2 cm thick. The lid 1 can be loose-fitting or provide a tight seal with the vessel 2. The lid 1 may take the form of a plate or an inverted dish.

A temperature probe 5, which may be fiber optic temperature sensor, can be inserted within the vessel 2 to monitor the internal temperature of the MAF composition 10 during the microwave treatment of the medical waste 4. In a particular embodiment, the amount of irradiation in the microwave chamber is based on the temperature reading from the temperature probe.

The microwave oven 12 can, for example, be a domestic ("kitchen") microwave oven, such as a Sears KENMORE® microwave oven (Model 721.62461, 1.2 KW, 2.45 GHz, 13.5 Amp). With this microwave oven 12, the loaded vessel 2 can be placed in the microwave oven 12 and irradiated for about 10 to about 30 minutes to remediate the medical waste 4. If a different size microwave oven is used (e.g., 500 W to 5 KW), the irradiated times necessary to remediate the medical waste 4 would be adjusted accordingly.

As shown in FIG. 1, the vessel 2 includes an opening 7 on a side. The opening 7 is of a size sufficient to accommodate a cable 6 from the temperature probe 5. The temperature probe 5 is placed in the center of the immersed medical waste 4, with its cable 6 transiting the vessel through the opening 7 described above. The cable 6 can be an optical fiber cable for probe 5 where probe 5 is a fluoro-optic temperature sensor. The cable 6 of the temperature probe 5 can be made of a material having a size that is sufficient and durable to exit the microwave oven through its closed door, without impeding the functioning of the probe 5 or the microwave oven 12. In one embodiment, the opening has a diameter of no greater than 2 mm, and the temperature probe 5 is a LUXTRON® model One sensor (registered trademark of Luxtron, Inc., Santa Clara, Calif.), used to measure temperature within the MAF composition 10.

For a typical collection of medical wastes, the proportion of MAF composition 10 to medical wastes 4 can be, for example, about 1.5:1 (vol/weight), which generally is sufficient to immerse all types of medical wastes in the MAF composition 10. For example, for 100 g of medical waste 4, 150 mL of the MAF composition 10 can be employed, and for 400 g of medical waste 4, about 600 mL of MAF composition 10. The parameter that determines the actual volume of the MAF composition 10 used is that the medical waste 4 should be completely immersed in the MAF. If necessary, the medical waste can be compressed by the administration of a weight 3 on top of the medical waste 4 and/or by applying mechanical pressure to the medical waste 4. Preferably, the medical waste 4 is compressed before being immersed in the MAF composition 10, but it can be compressed after immersion.

The microwave remediation is carried out for a time sufficient to remediate the medical waste 4. Preferably, the total irradiation time is from about 5 minutes to about 60 minutes. The precise irradiation time will be dependent on factors such as size and power of microwave oven 12, amount of medical waste 4, and other similar factors. The exact time can be determined by feedback from the temperature probe 5. The feedback can be monitored manually and manual adjustments to the irradiation cycle can be made. Alternatively, the feedback can be automated with a controller 14. The controller 14 can receive temperature inputs from the temperature probe 5 and adjust the irradiation cycle accordingly. For example, the controller can be programmed to shut off the microwave oven once a predetermined temperature is reached. After a period of cooling, the controller can then restart the microwave oven after a predetermined time or when a predetermined "cooled" temperature is reached or the controller can signal that remediation is complete.

It is contemplated that a minimum residence time of about 5 minutes at about 200° C. is a threshold to ensure remediation. It is further contemplated that this residence time and temperature applies to a large variety of medical waste types, varied infectious organisms (both bacteria and viruses), varied medical waste/MAF ratios, and varied microwave irradiation times. In keeping with the above residence time, the microwave irradiation may be turned off for short periods of time, for example, about 120 seconds or less, during the total irradiation cycle, either manually or automatically, depending on the feedback from the temperature probe. Preferably, the temperature is maintained at least about 40° C. below the boiling point or the decomposition temperature of the MAF. For example, when PEG is used as the MAL, a maximum temperature of 240° C. may be set in the feedback loop that controls the microwave oven based on the temperature information. When this temperature is reached, the microwave irradiation can be shut off for, for example, about 30 to about 90 seconds, then turned on again for, for example, about a 60-second period. The cycle can be repeated as needed. This process can be done manually or automatically by programming the controller 14 to interact with the temperature probe 5 and the microwave oven 12.

In a particular embodiment, a typical 400 g sample of medical waste 4 immersed in 600 mL of MAF composition 10 and placed in the microwave oven 12. The microwave oven is run for about 15 minutes, at which time the microwave oven is temporarily shut off. Through 30 minutes, the number of such shutoffs does not exceed two, each not exceeding about 60 seconds. A typical final temperature for the MAF is in the range of about 230° C. to about 235° C. After the final temperature is reached, the microwave oven is shut off and the vessel is removed from the microwave oven. The MAF is then allowed to cool to near ambient (room) temperature. The cooling period in ambient air is approximately twice the microwave irradiation time.

The MAF advantageously has the consistency of a very thin gel at ambient temperature and a milk-like sol at the higher temperatures reached in the microwave process; it remains so throughout the procedure. As a result of this temperature control, negligible vapors will be produced during the remediation, and any such vapors are contained within the vessel and its lid. These vapors are seen to be absent on cooling of the vessel, indicating either condensation or dissolution into the MAF. Little (about 1%) to none of the microwave enhancers of the MAF is lost onto the medical waste substrates, due to the sol-like nature of the MAF.

After cooling, the medical waste 4 may be press-strained to remove the MAF composition 10 from the medical waste 4. The MAF composition 10 can be press-strained directly into the microwave vessel 2 or into another container. The press-straining can be done by hand, by pressing down on the weight 3 to effect the straining, or by other known means. Generally, less than about 10% of the volume of the MAF composition 10 is retained in the medical waste 4. The more rigorous the press-straining, the less the volume of MAF composition 10 that is lost in the medical waste 4. It is contemplated that the volume of the MAF composition 10 in the medical waste can be reduced to below about 2.5%. The recovered MAF composition 10 can be re-used multiple times. It is contemplated that the MAF composition 10 can be reused as many as 20 or more times.

Detailed chemical and other analyses of the MAF following multiple (greater than about 20) uses of MAF according to the invention have shown no hazardous or toxic products; the data are given in Example 8 below. After approximately 20 uses, the MAF's volume generally is sufficiently reduced such that the lost volume must be made up with the addition of fresh MAF. The MAF can be discarded in ordinary sewerage by non-commercial entities, with negligible financial and environmental implications. For example, when PEG, a food additive, is used as the MAL, it has been determined that the MAF can generally be discarded in household sewerage without any pre-treatment.

Another embodiment of a system of the invention is shown in FIGS. 2-9. FIG. 8 is a block diagram of the microwave remediation procedure using this embodiment. The remediation instrument represented in these figures is referred to generally as remediator 100.

For treatment in the system of FIGS. 2-9, medical waste 4 is collected in one of several ways. In one collection method, medical waste 4 such as medical waste is collected in a "red bag", e.g. 182 in FIG. 2B. A "red bag" is a bag used for collection of biohazardous medical waste. Such bags are available commercially from suppliers such as ScienceWare/Bel-Art or other commercial vendors. One or more of the bags can be held within a larger, preferably perforated, microwave-transparent (PTFE such as DuPont TEFLON®) waste receptacle 102 shown in FIG. 2B. When full or when it is desired to treat or empty the medical waste 4, the entire waste receptacle 102 is transported to the remediator 100, where it can interlock into a main remediation chamber 120 (the bag can be tied or sealed first, depending on the type being used). The advantage of this approach is that multiple waste receptacles 102, i.e., waste receptacles deployed at multiple points of medical waste collection, can feed into a single remediator 100. The cost of the waste receptacles 102 is small in relation to the cost of the remediator 100, and this mode of use also facilitates maximum use of the remediator 100.

Figure 7:
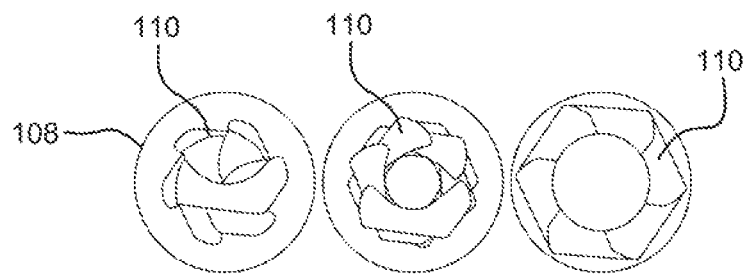
FIG. 7 illustrates the operation of an adjustable opening of the apparatus of FIG. 2A.

In another collection method, medical waste 4 is collected in a standard, commercially available "sharps/bio-hazard" container which may be made of propylene. The sharps container can be kept in the same manner within the larger waste receptacle, and interlocked with the remediator 100 when full. The waste receptacle 102 can be made of any of the same materials as described for vessel 2. PTFE is the preferred material for the waste receptacle 102 due to its microwave transparency. In addition, PTFE is chemically inert and has thermal durability (to over 280° C.). The waste receptacle 102 comprises a wall 104 and a base 106. The base 106 includes one or more adjustable openings 108. As shown in FIG. 7, the adjustable opening 108 may include an iris diaphragm 110, having a plurality of blades 110. Alternatively, the adjustable opening 108 may include a gate valve, a "flower-petal" valve, a hinged door, or another similar arrangement. The adjustable opening can be controlled manually such as with a hand crank or wheel. The adjustable opening can be controlled automatically, for example, being programmed such that its operation is under the control of controller 114. The adjustable opening can be controlled through a combination of automatic and manual control, such as automatic control with a manual override feature. As shown, the wall 104 is cylindrical, but other shapes can be utilized. As shown in FIG. 2B, the wall 104 can be perforated with a plurality of holes 112 to permit MAF ingress and egress. The holes 112 in the waste receptacle 102 wall 104 can be spaced randomly, asymmetrically or evenly spaced. As shown in FIG. 2B, the holes 112 are evenly spaced in the waste receptacle 102. The size of the holes or perforations depends on the desired microwave frequency. For example, for a microwave frequency from about 2 to about 3 GHz, the size of the holes or perforations are preferably greater than about 1 cm, more preferably greater than about 2 cm, and most preferably greater than 3 cm.

The waste receptacle 102 may be of various sizes, with the determinative factor on size being the waste receptacle's ability to fit into the remediator 100. The waste receptacle 102 can have a circular, triangular, or rectangular cross section, and it can have a cross section of any other symmetrical or asymmetrical shape. A cylindrical waste receptacle may have, for example, dimensions of about 12 cm diameter by about 20 cm depth, with a resultant volume capacity slightly over 2 liters. A cylindrical waste receptacle of that size can hold approximately 1.4 kg of medical waste.

The waste receptacle 102 can be interlocked into the main remediation chamber 120, which may have, for example, dimensions of about 18 cm diameter by 30 cm depth, with a resultant volume capacity of about 7.5 liters. In this embodiment, the MAF reservoir 130 holds about 7.5 L of fluid at room temperature, and about 7.4 L at an MAF temperature of 220° C. Generally, less than half of the maximum capacity of the MAF reservoir 130 is utilized during remediation. The overall dimensions of the remediator 100 preferably are approximately those of a tabletop photocopier.

The dimensions and capacities for the waste receptacle, remediation chamber and the MAF reservoir are merely illustrative and in no way limit the scope of the invention. The precise dimensions and capacities will be determined based on demand, space requirements, and other similar factors.

After the waste receptacle 102 has been placed into the remediation chamber 120, the chamber can be closed by placement and/or attachment of a chamber assembly 140. In this embodiment, the chamber assembly 140 includes a chamber closure 142 to close the top aperture of the remediation chamber 120. The chamber closure 142 may be a lid, a cover, a door, or other similar devices to close the aperture of the remediation chamber. The aperture can be located on top of the remediator 100, on the side of the remediator 100, or on the bottom of the remediator 100.

Figure 2A:
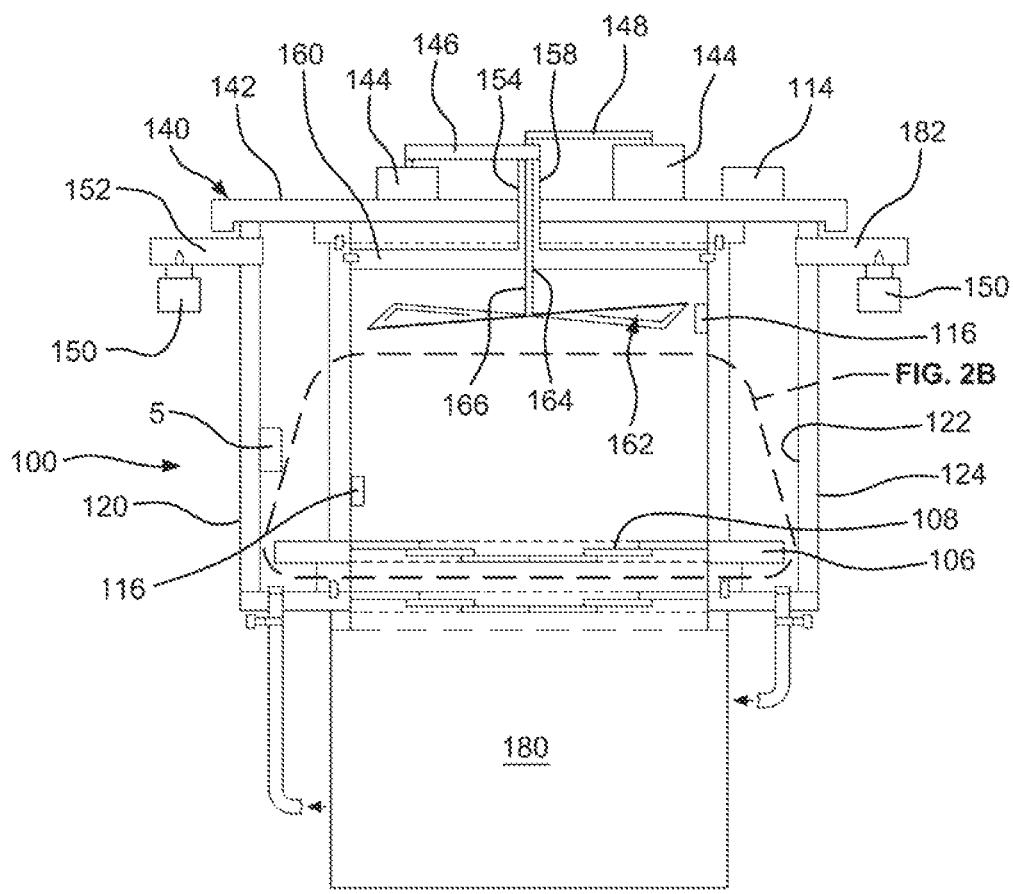
FIGS. 2A and 2B are schematic views of another apparatus for microwave treatment of medical waste.
Figure 2B:
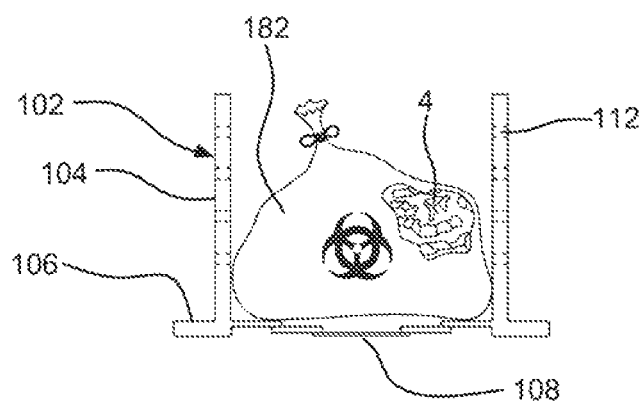
Figure 3:
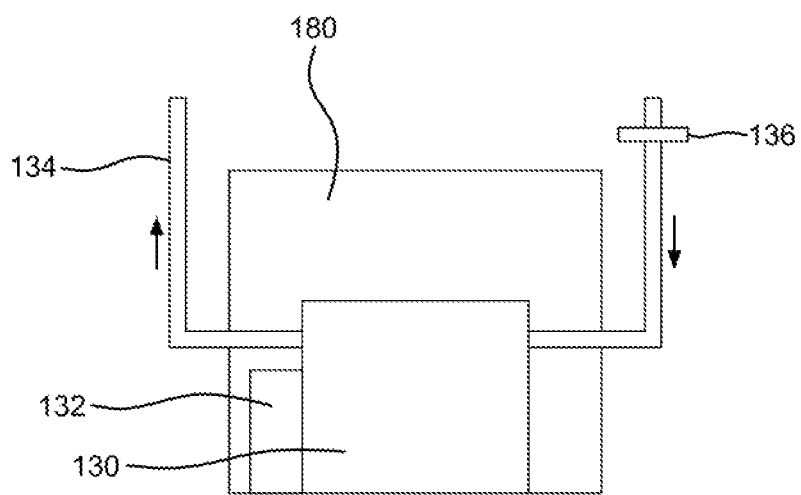
FIG. 3 is a rear view of the MAF reservoir of the apparatus shown in FIG. 2A.
Figure 4:
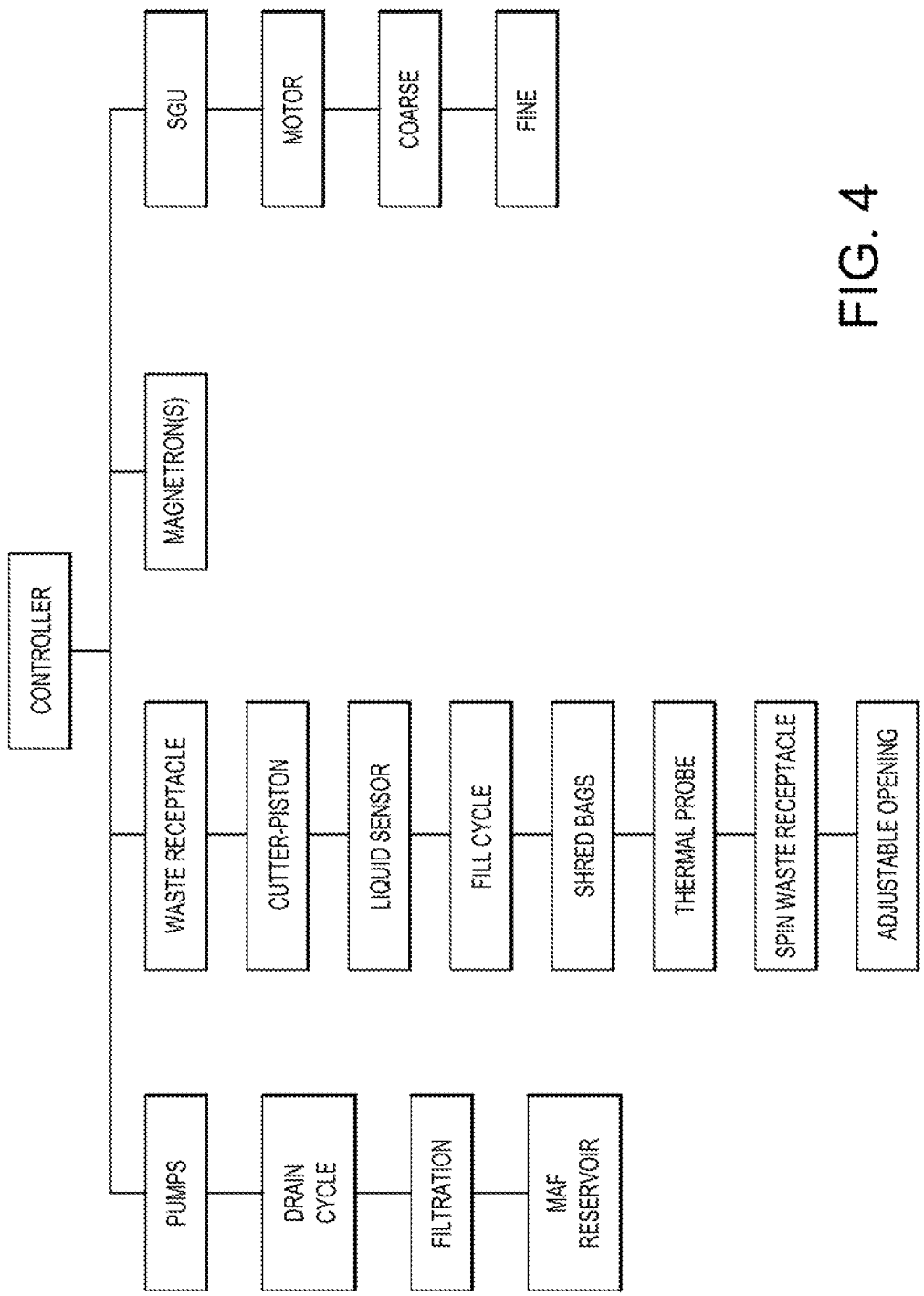
FIG. 4 is a schematic illustration of the interaction between the controller and the components of the apparatus of FIG. 2A.

As shown in FIG. 2A, the chamber assembly 140 also includes motors 144, drivers 146 and 148, a magnetron 150, and an optional waveguide 152. The chamber assembly also includes a central opening 154 through which pass a pair of shafts 156 and 158. The pair of shafts 156 and 158 are positioned such that inner shaft 156 is rotationally positioned inside outer shaft 158. The pair of shafts 156 and 158 is attached to the lid 160 of the waste receptacle 102, and to a cutter blade 162. The motors 144 and magnetron 150 are in communication with the controller 114, attached to chamber closure 142. Alternatively, the magnetron 150 and the motors 144 can be separately positioned.

When the chamber assembly 140 is attached, lid 160 is slidably retained within the waste receptacle 102. The lid 160 contains the medical waste 4 and the added MAF composition 10. The lid 160 can act as a piston to facilitate removal of the remediated medical waste from the waste receptacle 102. The lid 160 can also aid in directing the remediated medical waste into a second waste receptacle 180, which can include a grinder, which includes shredders and other devices that can reduce the size of the medical waste. The second waste receptacle may be adjacent to the first waste receptacle and the first and second waste receptacles may be oriented to allow transfer of the medical waste from the first waste receptacle to the second waste receptacle through an adjustable opening in the remediation chamber. Lid 160 contains an opening 164, through which passes inner shaft 156. Outer shaft 158 is attached to the outer surface 166 of lid 160, and drives the rotation of the waste receptacle 102.

The waveguide 152 directs microwave radiation from the magnetron 150 into the remediation chamber 120. The remediator 100 can operate without a waveguide 152 if, for example, the magnetron 150 is mounted more centrally.

A first motor 144 controls the operation of the waste receptacle 102 and is in communication with a means to rotate the first waste receptacle, and second motor 144 drives the cutter assembly and thus controls operation of the cutter blade 162, the cutter blade 162 being kept beneath the lid 160 when the cutter blade 162 is not being used for cutting bags of medical waste. The inner cutter blade shaft 156 is connected to first motor 144 by a driver 146, which can be a drive belt or other means of directing power from a motor to a shaft, as known to those skilled in the art. While the cutter blade 162 is shown as a fan-like blade extending from the top of the remediator 100, other orientations are contemplated. For example, the cutter assembly and thus the blade 162 can extend from the bottom, side, top, through the remediator chamber closure and any combination thereof. Other designs are also contemplated. For example, the blade 162 can comprise vertical blades like kitchen blender blades. Various sizes are also contemplated, the size generally being dependent on the size of the remediator 100.

Second motor 144 is connected to the outer shaft 158 by a driver 148, which may be a drive belt or other means of directing power from a motor to a shaft, as known to those skilled in the art. The drivers 146 and 148 may be different or identical, depending upon manufacturing decisions. Second motor 144 controls rotation of the waste receptacle 102.

As shown in FIG. 2A, the remediation chamber 120 includes at least one temperature probe 5. Preferably, the remediation chamber 120 includes at least two temperature probes 5. The temperature probe 5 may, for example, be a LUXTRON® One sensor described earlier. Alternatively, the temperature probe 5 may be a thermocouple with a suitably shielded connector. The temperature probe 5 can be attached to the inner wall 122 of the remediation chamber 120. The temperature probe is in communication with the first waste receptacle and controller.

FIG. 2A illustrates two magnetrons 150 as sufficient to provide microwave irradiation of the remediation chamber 120. The magnetrons 150 can be, for example, Panasonic 2M265 (Matsushita Electrical, Japan), Hitachi 2M21A magnetron (Hitachi, Ibaraki, Japan) or MWO 1420B (Sun Rise Ltd., Japan). The total power of both magnetrons is less than 2.5 KW. Greater and lesser amount of power is contemplated and may be dependent on factors such as size of the remediation chamber 120, amount of MAF, amount of medical waste, orientation of the magnetrons 150 in relation to the remediation chamber 120, and other similar factors.

An outer shell 124 and an inside shell 122 of the remediation chamber 120 preferably are metal. Preferably, the inside shell 122 is a metal with an MAF resistant coating, or stainless steel. Appropriate waveguides 152 channel microwaves generated at the two magnetrons 150 into the remediation chamber 120.

As will be apparent to those skilled in the art, the dimensions described herein are for purposes of illustration only, and larger or smaller remediators 100, and its component parts, may be constructed without departing from the spirit and scope of this invention.

The operation of the remediator 100 is described as follows and in FIG. 8A.

Figure 8A:
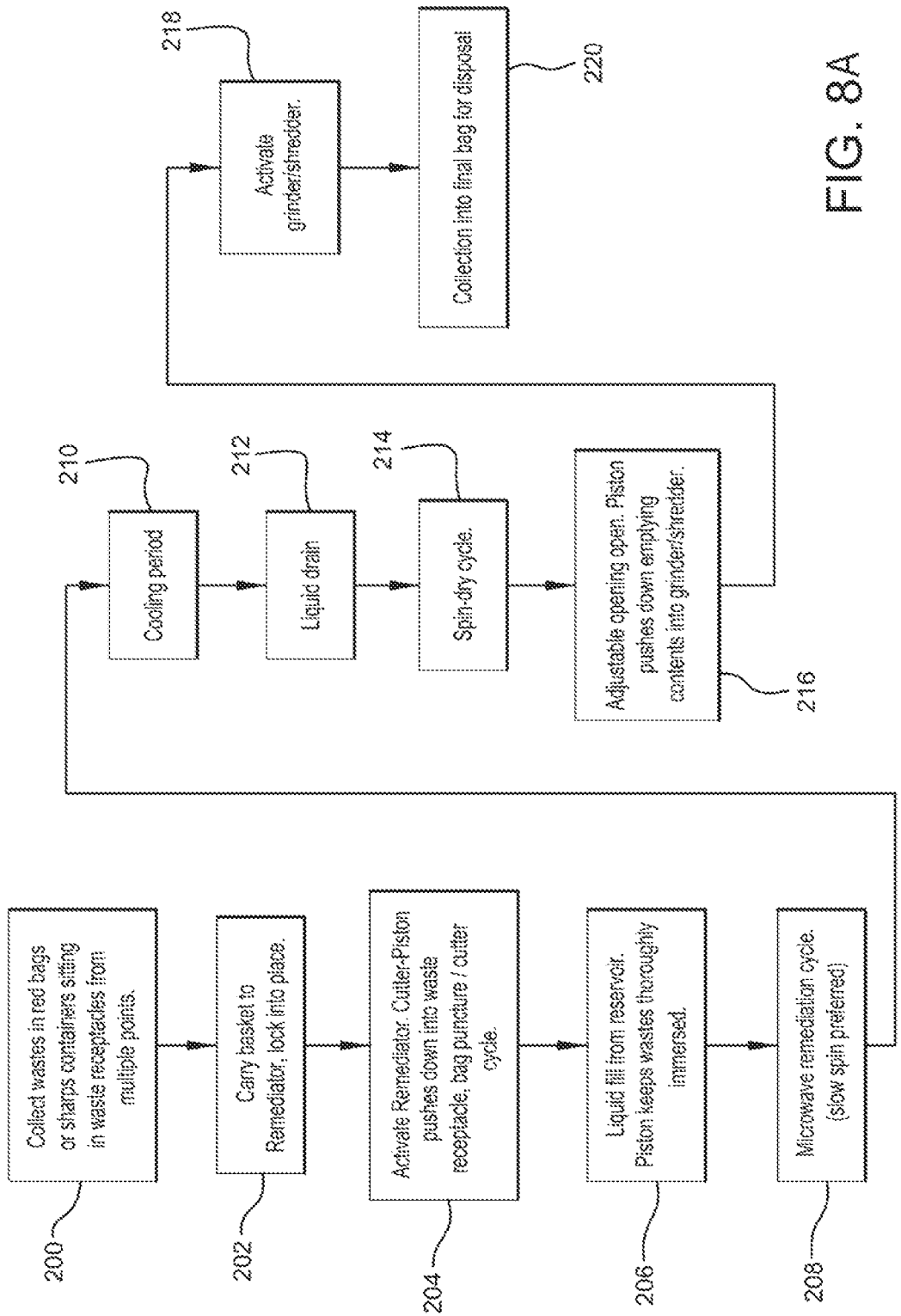
FIGS. 8A, B and C are flow charts describing a process for microwave treatment of medical waste.

After loading of the medical wastes (Step 202) in the remediator 100, its main cycle is activated at step 204 (FIG. 8A). This causes the cutter-piston 162 to come down into the bag 182, cutting it open (if it is sealed) as well as dispersing and compacting the contents. Step 204 can be completed in from a few seconds to tens of minutes. Preferably, medical waste 4 is homogenously distributed in the remediation chamber 120. The initial cutter-piston cycle aids in puncturing the bags holding the medical waste 4, and aids in distribution of the medical waste within the remediation chamber 120. The cutter-piston cycle can also serve to compact the medical waste 4. Compaction may reduce the volume of the medical waste 4 to a greater extent than having a shredder/grinder unit before the microwave cycle. The reduction in volume before the microwave irradiation cycle is commenced may be about 50%.

Preferably, step 204 is completed in from about 1 minute to about 2 minutes. Step 206 can be initiated after step 204 is completed. Alternatively, Step 204 and step 206 can be run concurrently either for the entire time of Step 204 or for only a portion of time of step 204. In step 204, the MAF composition 10 fills the remediation chamber 120 from the MAF reservoir 130. The volume of MAF composition 10 added is generally about 3 L for the embodiment described herein but can be more or less depending on the size of the remediator 100, and its component parts, and on the amount of medical waste 4 in the remediation chamber 120. A pump 132, also in communication with controller 114, dispenses the MAF composition 10 into the remediation chamber 120 through tubing 134. Once sufficient amounts of the MAF composition 10 are in the remediation chamber 120, step 208 can be initiated which includes beginning irradiation. Step 208 can range from about 10 minutes to about 30 minutes. The irradiation times can be adjusted, preferably to ensure residence times at 200° C. of at least 5 minutes. The waste receptacle 102 can be rotated within the remediator 100 during this time period. Preferably, the rotation is at a slow spin, generally from about 2 to about 20 revolutions per minute ("rpm"). The rotation can be accomplished by having the waste receptacle 102 on a rotating plate (e.g. a turntable), having a rotating arm descending from the top assembly attached to the waste receptacle 102, or by other means known by those skilled in the art.

After completion of step 208, there is a cooling period of step 210. The cooling period preferably is from about three to about five minutes in duration. During or after step 210, the MAF composition 10 is drained in step 212. During step 212, the MAF composition 10 preferably passes through a filter 136, which acts as a sieve to separate the MAF composition 10 from any small-particulate remediated medical wastes, including any partially molten plastics, that may be small enough to be carried with the MAF composition 10 during the fill/drain cycles. Typically, the small-particulate remediated medical wastes that may need to be filtered out of the MAF composition 10 comprises less than 1% by weight of the total medical wastes. The filter unit 136 may be physically removed and cleaned of accumulated (i.e., filtered) debris, preferably every five remediation cycles. The drain cycle may also serve to further cool the MAF composition 10. Step 214 is then initiated and may comprise rotating the first waste receptacle between the draining step and transferring the waste to remove liquid from the irradiated medical waste. In particular, Step 214 includes spinning the medical waste 4 after the MAF composition 10 has been removed, thereby further drying the medical waste 4. This step can be run for a period of from about 1 to 10 minutes, preferably about 5 minutes. Preferably, the rotation is a fast spin, which is generally on the order of between 10-20 times the slow speed described above for the waste receptacle 102. Steps 206, 208, 212, and 214 are like those of a clothes washing machine, and the waste receptacle 102 has a configuration that resembles a top-loading washing machine.

At the end of step 214, the medical waste 4 is nearly dry, about as dry as clothes from a clothes washer after a comparable spin cycle. The absorbent components of the medical waste 4, such as cotton swabs or tissues, retain some of the MAF composition 10. The amount of MAF composition 10 retained by the medical waste 4 is generally less than about 2.5% of the original volume of the MAF composition 10. The small retention of the MAF composition 10 in the medical waste 4 is aided by using only about half of the volume capacity of the microwave chamber, which allows for rapid cooling of the MAF composition 10. The rapid cooling allows for easier draining of the MAF composition 10 because the MAF composition 10 is less viscous at lower temperatures.

The final temperature achieved in the MAF after microwave irradiation and the temperature drop at the end of the cooling period will vary with the type and amount of medical wastes remediated. Generally, in one embodiment, the final temperature after irradiation is about 250° C., and the temperature after 5 minutes of cooling is about 175° C.

Figure 5:
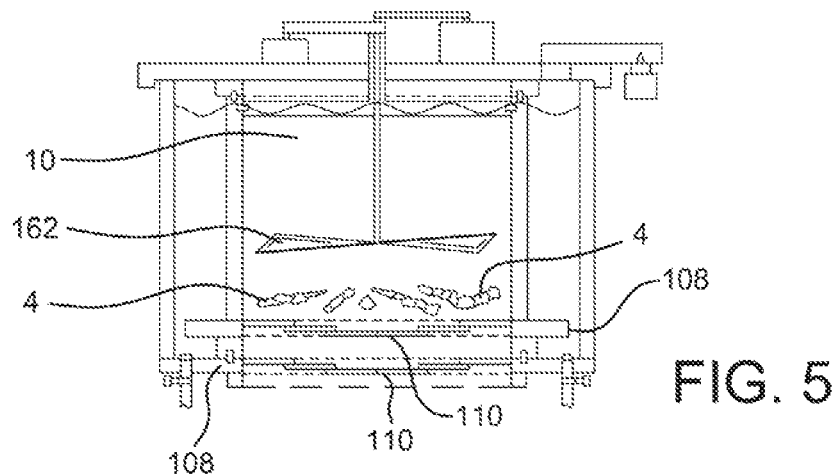
FIG. 5 illustrates operation of the apparatus of FIG. 2A after addition of the MAF into the remediation chamber.
Figure 6:
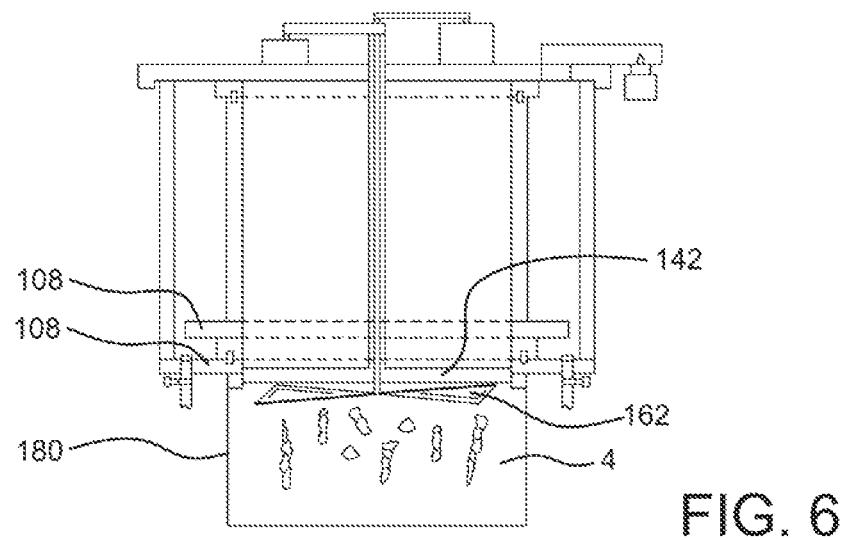
FIG. 6 illustrates transfer of the treated medical waste into the second waste receptacle of the apparatus of FIG. 2A.
Figure 9:
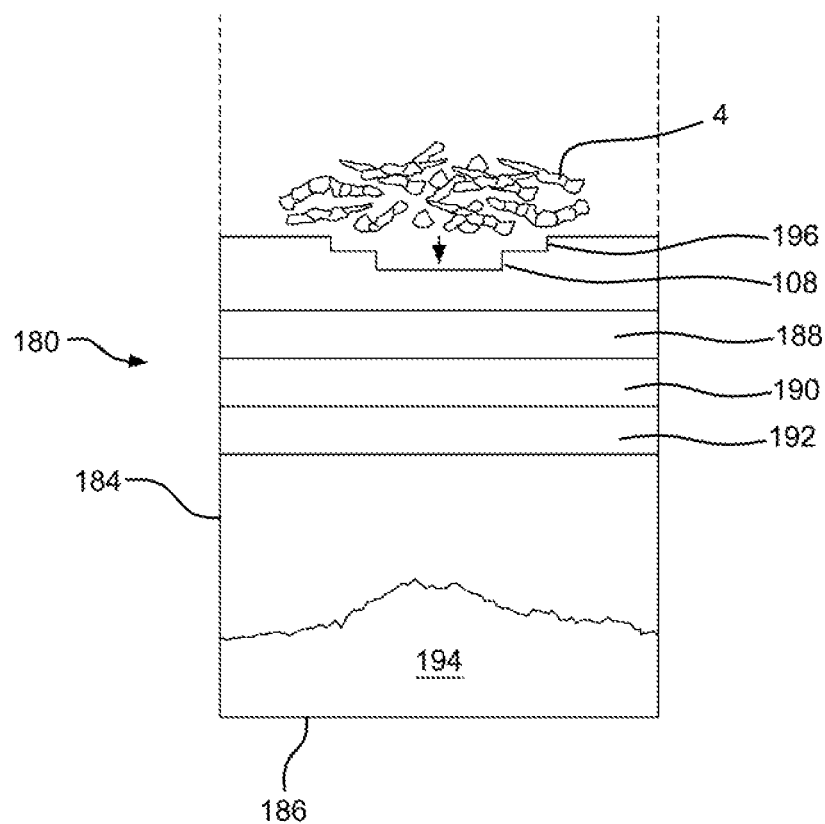
FIG. 9 is a schematic illustration of a second waste receptacle of the apparatus of FIG. 2A.

Step 216 follows completion of the spin-dry cycle. In step 216, the irises 108 at the bottom 106 of the waste receptacle 102 open and the remediated medical wastes are dumped into the second waste receptacle 180, as shown in FIGS. 5-6 and 9. Step 218 is performed in the second waste receptacle 180, which can include shredding and grinding of the irradiated medical waste 4. The second waste receptacle 180 may be assembled from commercially procured components. Inexpensive grinder/shredder heads of varied size and capacity and specifically designed for medical wastes are available from various commercial sources per se (i.e. not as part of a full shredder unit). Exemplary vendors are SSI Shredding Systems Inc. (Wilsonville, Oreg.), Franklin-Miller (Livingston, N.J.) and Gross (Heilbronn, Germany). As shown in FIG. 9, two shredder heads 190 and 192 can be used serially. A preferable serial arrangement includes a coarse grinder 190, with a larger spacing, for large objects, e.g. larger syringes and pieces of gowns; and a second, fine grinder 192, for finer grinding. The second waste receptacle 180 may be customized for a specific application, such as, for example, use within a hospital ward, an Intensive Care Unit ("ICU"), a doctor's clinic and so on.

The second waste receptacle 180 includes a wall 184 and a bottom 186. A divider 196 that contains an adjustable opening 108, such as a second iris diaphragm, can serve as a top for the second waste receptacle 180. Alternatively, the adjustable opening 108 can be positioned on the side or bottom of the second waste receptacle 180. While the size of the second waste receptacle 180 can vary in different embodiments, its capacity should be at least that of a fully loaded waste receptacle 102. The second waste receptacle 180 includes a motor 188 in communication with the controller 114, one or more shredder heads 190 and 192, and/or the adjustable opening 108.

The final product, at the end of the processing cycle, is generally an unrecognizable fine-particulate solid medical waste 194, classified as Class 10 municipal waste and suitable for disposal as ordinary household refuse, in landfills, and the like. This product can be bagged and sealed as part of step 220. An optional compactor step may be added as the final step, which would further compact the treated medical wastes, further reducing the volume and removing an additional, small amount of MAF still present in the treated medical wastes.

Due to the comparatively high MAF temperatures encountered during the remediation process, the joint seals and valves used in the apparatus shown in FIG. 2 et seq. should be made for function with high temperature fluids. High temperature joint seals and valves are widely available from both commercial suppliers as well as scientific suppliers, for example, retailers such as McMaster-Carr Supply Co., Grainger, Cole-Parmer and Anko Products.

The advantage of the shredding/grinding the medical waste after remediation, as embodied in the present invention, is that the shredder/grinder unit does not have to be decontaminated after each use because the medical waste passing through it has already been remediated. The design of the remediator 100 and the microwave irradiation cycles ensure that all its components become remediated at the end of the irradiation cycle, primarily through being immersed in the MAF during microwaving. The MAF drained back into the liquid reservoir after the cycles are complete is sterile.

An optional, final step in the remediation process may be further compaction of the medical wastes after they have been processed through the second waste receptacle 180. Although this step is not explicitly shown in the drawings, FIGS. 5-6 illustrates the medical waste being pushed into the second waste receptacle 180 by the cutter-blade 162. By pushing the cutter blade 162 further into the second waste receptacle 180, further compaction can occur. This step can squeeze out an additional approximately 50% of the MAF still remaining absorbed in the medical wastes.

Figure 8B:
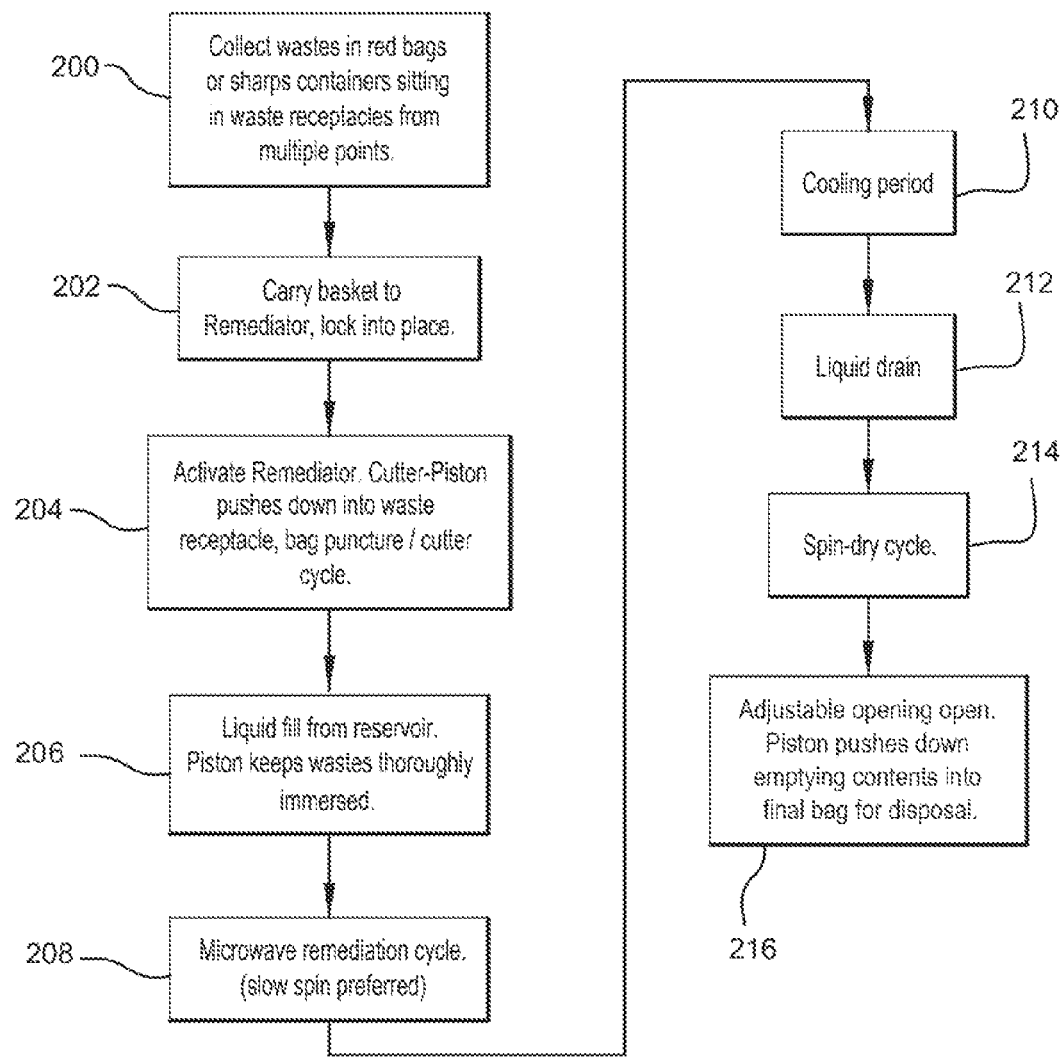
Figure 8C:
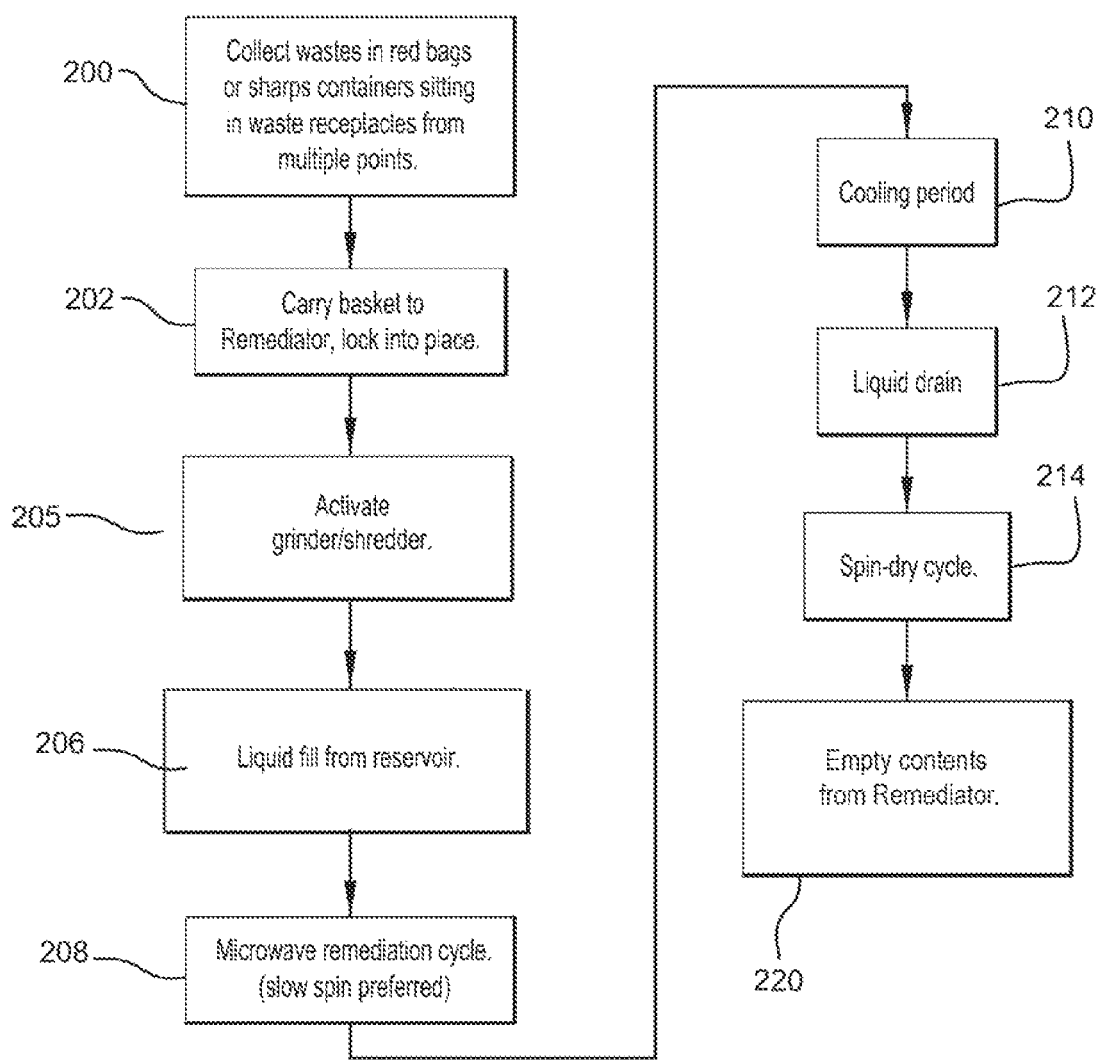

Other embodiments are set forth in FIGS. 8B and 8C. In FIG. 8B, Steps 200-204 are generally the same as set forth for FIG. 8A. However, in FIG. 8B, the Cutter/Piston, may act to also shred the waste in Step 204. In yet another embodiment set forth in FIG. 8C, step 204 may be eliminated and the grinder/shredder is activated immediately after step 202. The procedure followed is similar to that set forth step 218 in FIG. 8A. The shredding/grinding step designated step 205 (as in FIG. 8A) is followed by Steps 206, 208, 210, 214, 216 and 220. Step 208, the irradiation step, may range from about 20 to about 240 minutes. The time may be dependent on the total MAF volume, which may vary from about 3 L to about 70 L. The cooling period in step 210 may range from about 5 to about 20 minutes. Further, in step 220, the medical waste may be removed from the waste container.

Preferred approximate times for each of the steps for the operation of the apparatus as described above, and with a typical medical waste sample may be as shown in Table 1.

TABLE 1

Operation of Apparatus (Steps)

| Step | Description | Preferred Time Range |
| --- | --- | --- |
| 204 (FIG. 8A, B) | Cutter-piston cycle | about 1 to about 2 minutes |
| 206 (FIG. 8A, 8B, 8C) | MAF fill cycle | about 1 minute |
| 208 (FIG. 8A, 8B, 8C) | Microwave irradiation cycle | about 10 to about 240 minutes |
| 210 (FIG. 8A, 8B, 8C) | Cooling period | about 3 to about 20 minutes |
| 212 (FIG. 8A, 8B, 8C) | MAF drain cycle | about 1 to about 2 minutes |
| | Sieve emptying step | about 0.5 to about 1 minute |
| 214 (FIG. 8A, B, C) | Spin-dry cycle | about 5 minutes |
| 216 (FIG. 8A, B) | Load second waste receptacle | about 0.5 to about 1 minute |
| 218 (FIG. 8A) 205 (FIG. 8C) | Shredding/ grinding | about 2 minutes |
| 220 (FIG. 8A, C) | Seal final medical waste bag | about 0.5 to about 1 minute |

The total of these times ranges from about 25 to about 260 minutes. These times do not include the optional, final step of further compaction.

The process can be performed at ambient pressure without any seals of any kind.

All cycles described in the foregoing, i.e. the entire microwave remediation process, can be automated, with a central, programmable, microprocessor-based controller 114. The controller 114 can include a feedback loop from the two temperature sensors 5 within the main remediation chamber 120. The controller 114 can control the power to the magnetron 150, the adjustable opening 108, the shedder/grinder of the second waste receptacle 180, the pumps 132, the motors 144, the cutter blade 162, and any other component that can be controlled by automation. The control can be based on predetermined time intervals, feedback from the temperature probes 5, and on other similar parameters.

Remediator 100 can also include a liquid sensor 116 to determine the liquid content of the medical waste. The liquid sensor 116 can be positioned approximately one-tenth of the way up the remediation chamber wall 122. If the liquid content of the medical waste exceeds a specified concentration, for example, 10% liquid by volume, the sensor 116 will send a signal to the control means 114 to alert the operator to dispose of the MAF liquid after the remediation cycle has been completed, rather than to reuse it, since the MAF would then be diluted ca. 10% with non-MAF liquids, reducing its efficacy. Thus, at the end of the remediation cycle, the used MAF is removed from the remediator 100, and discarded, and the reservoir 130 can be replenished with a fresh quantity of MAF.

Figure 10:
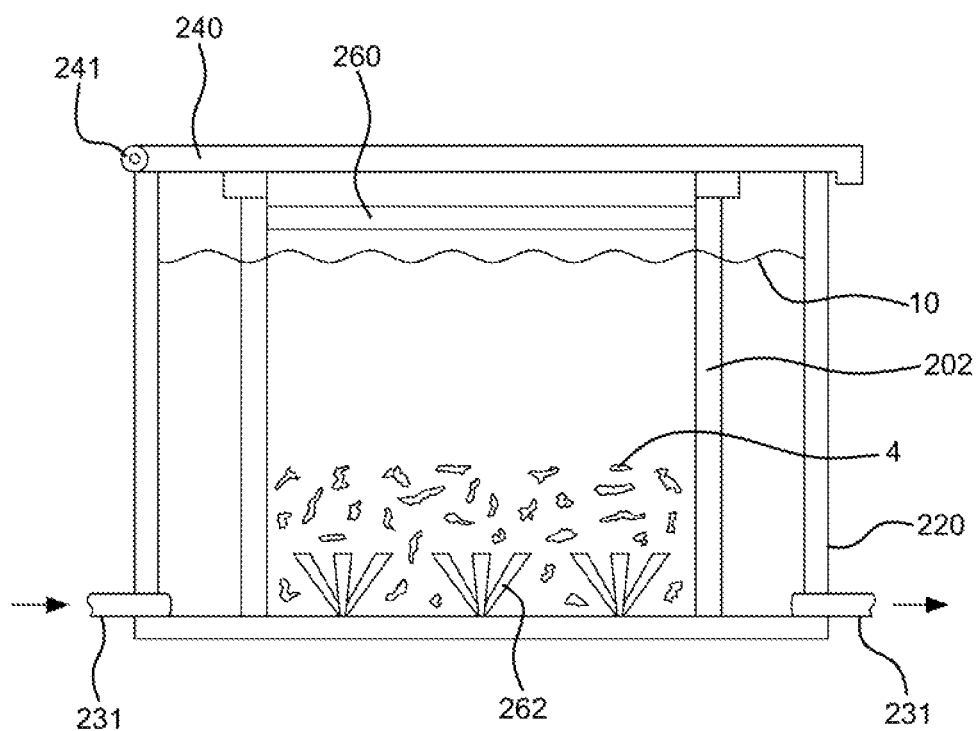
FIG. 10 is a schematic of another apparatus for microwave treatment of medical waste.

Another system of the invention is illustrated in FIG. 10, which shows a remediator 200. Remediator 200 shares many of the same components as remediator 100. Remediator 200 includes a main remediation chamber 220 wherein a waste receptacle 202 can be placed. The remediation chamber 220 and the waste receptacle 202 may have the same components and characteristics described above for remediation chamber 120 and waste receptacle 102, respectively. As with remediator 100, medical waste 4 is immersed in the MAF composition 10, which may be added and removed from the remediation chamber 220 through piping or tubing 231 in fluid communication with an MAF reservoir. The MAF reservoir can be integral with remediator 200 or can be a separate apparatus.

Remediator 200 includes a chamber assembly 240, which is connected to the main remediation chamber 220 by hinge 241. Other connections are also contemplated and it is also contemplated that the chamber assembly 240 can be placed on the remediation chamber 220 without connecting it. The chamber assembly includes a lid 260 that closes the medical waste receptacle 202. Alternatively, the lid 260 can be independent of the chamber assembly 240.

Remediator 200 includes blades 262 for cutting the medical waste 4. As shown, the blades 262 are oriented at the bottom of the remediation chamber 220 as a series of blade clusters. Alternatively, it is contemplated that the cutting of medical waste 4 can be performed by a single blade, a series of single blades, a blade cluster, and/or a series of blade clusters oriented on the top, sides, and/or bottom of the remediation chamber 220.

The remediator 200 can include a second waste receptacle for grinding the remediated medical waste. Alternatively, the second waste receptacle can be a unit separate from the remediator 200. The remediated medical waste in the remediator 200 may be disposed into the separate second waste receptacle through a raise-swivel-and-dump mechanism, much like the way contents of a dumpster are emptied into a trash truck.

Figure 11A:
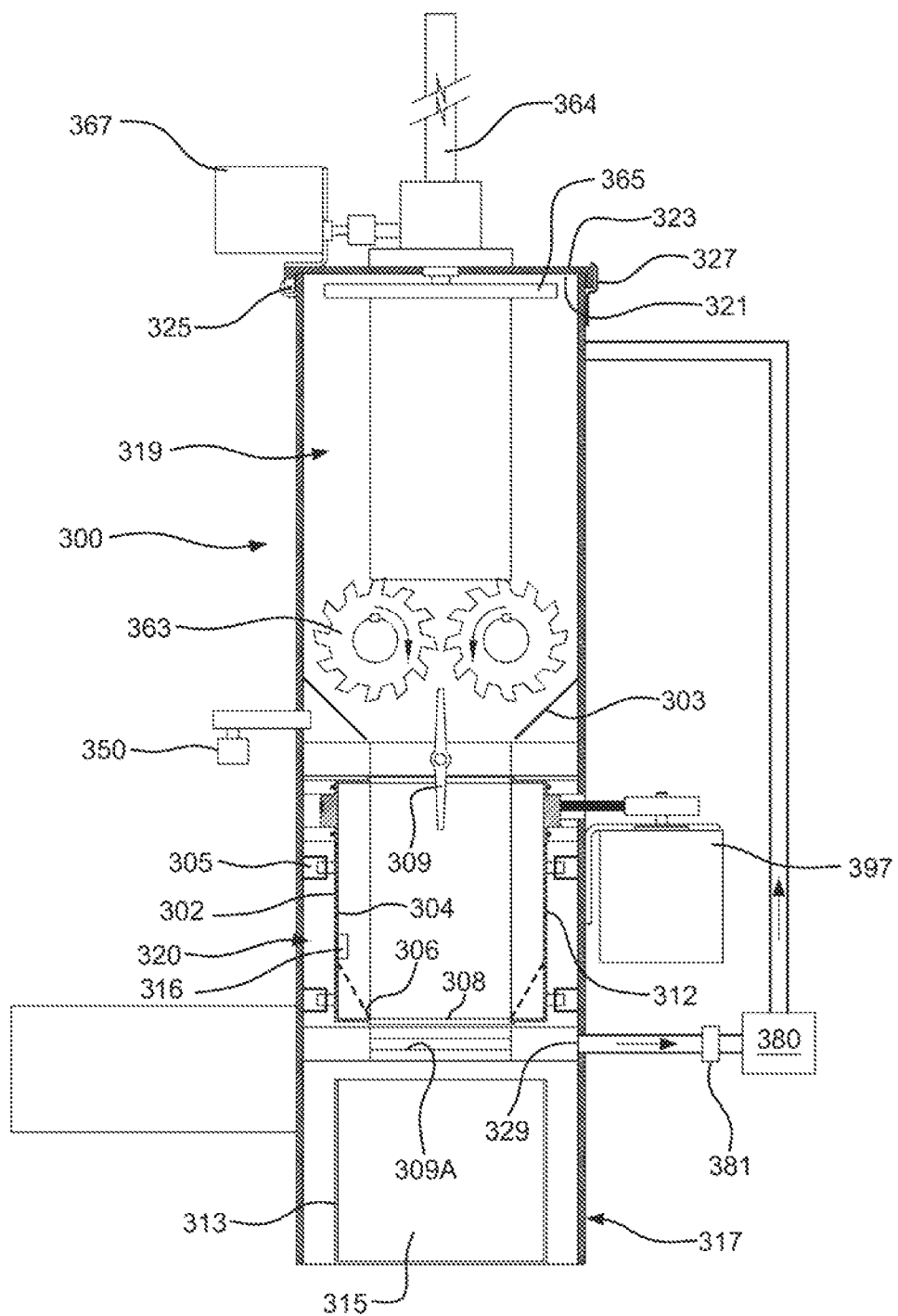
FIGS. 11A and 11B are schematic views of an apparatus for microwave treatment of medical waste, the apparatus having multiple grinders to grind the medical waste prior to remediation.
Figure 11B:
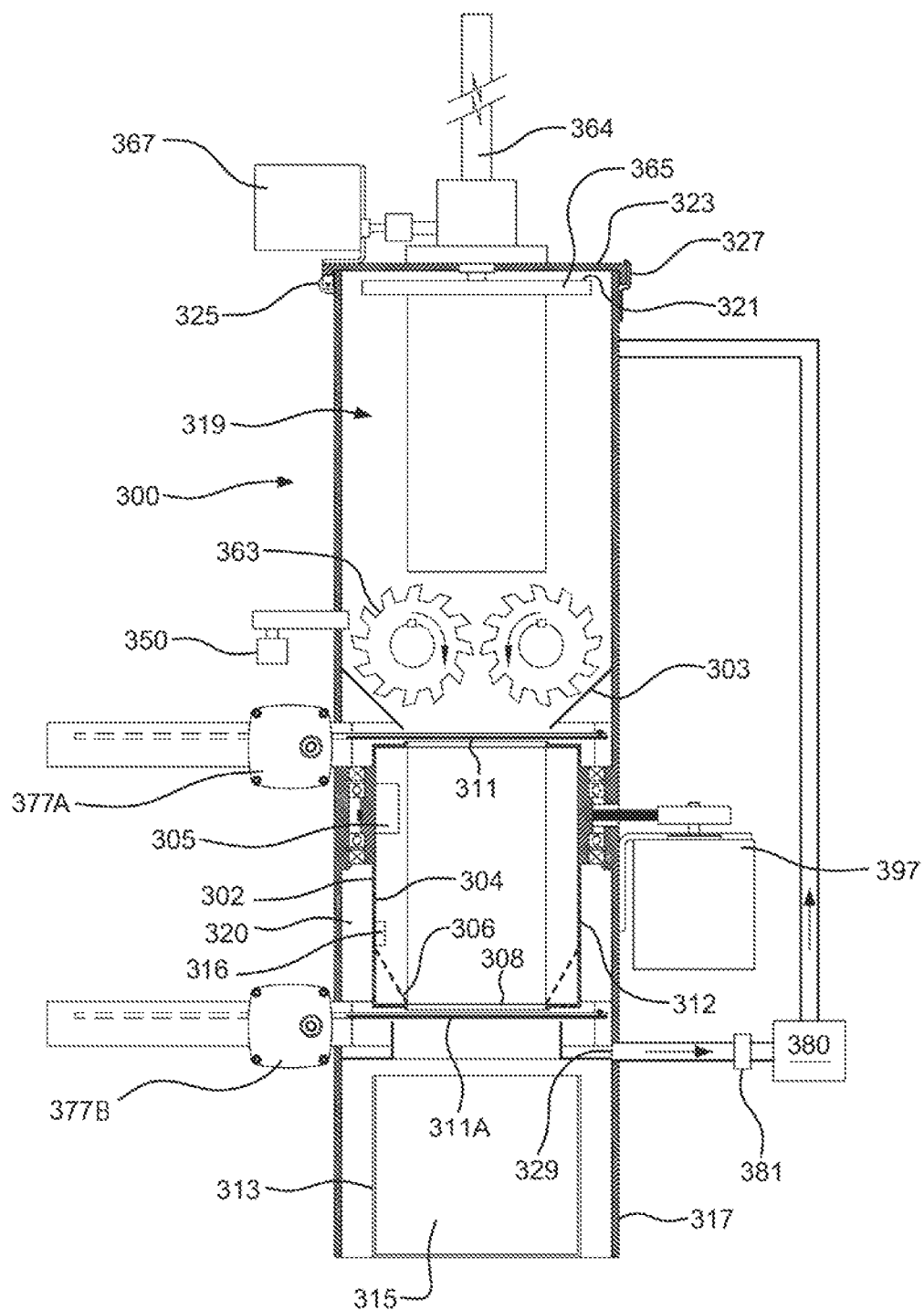

Another system of the invention is illustrated in FIGS. 11A and 11B, which show a remediator 300. The remediator 300 includes a first chamber 319. The first chamber 319 includes an opening 321 into which medical waste can be introduced. As shown, the opening is closed by a lid 323 having a hinge 325 and a latch 327. The latch 327 locks the lid 323 to the first chamber 319.

Closures other than the illustrated lid 323 are contemplated. For example, the remediator 300 can include a snug fit closure, a sliding closure, a loose fit closure, a center opening closure, and other closures known to one skilled in the art.

Locking mechanisms other than the illustrated latch 327 are contemplated. For example, the remediator 300 can include a lock and bolt setup, a hook and loop arrangement, a snap, a button, and other similar mechanisms.

As shown in FIGS. 11A and 11B, on top of the lid 323 is a piston assembly 364, which includes a motor 367 and a piston arm 364. The piston arm 364 extends through the lid to a piston head 365. In operation, the piston head 365 compacts medical waste in the first chamber 319, and directs the medical waste to two grinders 363 that grind the medical waste prior to remediation.

The grinders 363 may be driven by at least one motor. As shown, the grinders 363 rotate in opposite directions, which directs the medical waste between the grinders 363 thereby allowing the grinders 363 to reduce the size of the medical waste. The grinders 363 preferably can cut steel (e.g., syringes) and other similar materials that are commonly found in medical waste. The grinders 363 may be commercial off the shelf grinders or custom designed grinders.

Preferably, the grinders 363 produce ground medical waste in which substantially all of the medical waste is less than about 1 inch in size, more preferably less than about 0.5 inch in size, and most preferably less than about 0.25 inch in size. The smaller size allows for better treatment of the medical waste. For example, a smaller size allows for remnant liquids trapped in partially cut syringes, etc. to be remediated more effectively.

As shown, the first chamber 319 also includes an angled floor 303 for directing the ground medical waste to a remediation chamber 320, which is in fluid communication with the first chamber 319. The first chamber 319 and the remediation chamber 320 may be separated by, for example, a fluid permeable layer. The fluid permeable layer comprises a valve. As shown in FIG. 11A, the valve is a butterfly valve 309. As shown in FIG. 11B, the valve is a mesh gate valve 311. Other valves are contemplated and may be selected based on, for example, the ability of the valve to hold the weight of the medical waste. Preferably, the valve, when closed, allows fluid transfer between the remediation chamber 320 and the first chamber 319, but prevents solids from passing between the two chambers. For example, the valve may be a mesh gate valve.

The remediation chamber includes a waste receptacle 302, which houses the ground waste during remediation. The waste receptacle 302 may be made of any of the same materials as described for vessel 2. PTFE is the preferred material for the waste receptacle 302 due to its microwave transparency, chemical inertness and thermal durability (to over 280° C.). The waste receptacle 302 includes a wall 304 and a base 306. The base 306 includes an opening 308, which may be an adjustable opening such as the adjustable opening 108 of remediator 100 described above.

As shown, the wall 304 is cylindrical, but other shapes can be utilized. The wall 304 can be perforated with a plurality of holes 312 to permit MAF ingress and egress. The holes 312 in the waste receptacle wall 304 can be spaced randomly, asymmetrically or spaced evenly. The size of the holes or perforations depend on the desired microwave frequency. For example, for a microwave frequency from about 2 to about 3 GHz, the size of the holes or perforations are preferably greater than about 1 cm, more preferably greater than about 2 cm, and most preferably greater than 3 cm.

The waste receptacle 302 may be of various sizes, with the determinative factor on size being the waste receptacle's ability to fit into the remediator 300. The waste receptacle 302 can have a circular, triangular, or rectangular cross section, and it can have a cross section of any other symmetrical or asymmetrical shape. A cylindrical waste receptacle may have, for example, dimensions of about 12 cm diameter by about 20 cm depth, with a resultant volume capacity slightly over 2 liters. A cylindrical waste receptacle of that size can hold approximately 1.4 kg of medical waste.

Preferably, the remediation chamber includes a means for rotating the medical waste to allow for a more even application of the microwave radiation to the medical waste in the waste receptacle 302. For example, the waste receptacle 302 can be rotatable. Preferably, the rotation is at a slow spin, generally from about 2 to about 20 revolutions per minute ("rpm"). The rotation can be accomplished by having the waste receptacle 302 on a rotating plate (e.g. a turntable), having a rotating arm attached to the waste receptacle 302, or by other means known by those skilled in the art. Preferably, the waste receptacle includes a bar across the bottom to assist in forcing the medical waste to the sides of the waste receptacle 302 during rotation. The waste receptacle may contain one or more supports 305.

The remediation chamber 320 includes a drain 329 for draining a MAF, which is used in remediating the medical waste. The drain is in fluid communication with a MAF reservoir 380. After remediation, the MAF can be drained from the remediation chamber, run through a filter 381, and then stored in the MAF reservoir 380 until it is needed again. When it is needed, the MAF can be pumped from the MAF reservoir 380 to the first chamber 319 though piping, conduits, or any other manner known to one skilled in the art. Alternatively, the MAF is pumped into the remediation chamber 320. The remediation chamber further comprises a motor 397 for filling and draining of liquid. The remediation chamber 320 may include one or more temperature sensors as described with respect to remediator 100. The remediation chamber 320 may include one or more liquid sensors as described with respect to remediator 100.

The remediator 300 also includes at least one magnetron 350 for delivering microwave radiation to at least the remediation chamber. As shown, the magnetron 350 is centrally located on the remediator 300 such that microwave radiation can be delivered to the remediation chamber 320 and the first chamber 319. The remediator may have multiple (e.g., 2-6) magnetrons. As previously noted, the remediator contains a slanting floor 303. In a particular embodiment, the slanting floor 303 microwave transparent (e.g., made of PTFE) and the magnetron(s) is placed to the outside of the slanting floor. In the event that the slanting floor or subfloor 303 is made of metal, the magnetron is placed in a different location. The remediator 300 may also include a waveguide for directing the microwave radiation from the magnetron into at least the remediation chamber 320, and preferably into the remediation chamber 320 and the first chamber 319. More than one waveguide may be used.

The remediator 300 also includes a finish chamber 317 for receiving remediated medical waste from the remediation chamber 320. The finish chamber 317 is, as shown, separated from the remediation chamber 320 by a non-permeable layer such as a valve or door. The valve or door may be part of the remediation chamber 320, part of the finish chamber 317, or integral to both the remediation chamber 320 and the finish chamber 317. As shown in FIG. 11A, the valve is a butterfly valve 309A. As shown in FIG. 11B, the valve is a gate valve 311A. In a particular embodiment, as shown in FIG. 11B, the operation of these valves and movement of material between the upper and lower chambers and between the lower chamber and waste receptacle may be controlled by motors 377A and 377B respectively.

The finish chamber 317 includes a waste container 313 for receiving the remediated medical waste. Preferably, the waste container 313 is removable through an opening 315. The opening 315 may be at the bottom of the finish chamber 317 or on one of the sides of the finish chamber 317.

Remediator 300 and its associated components may be automated and/or controlled by a controller as described with respect to remediator 100.

Figure 12A:
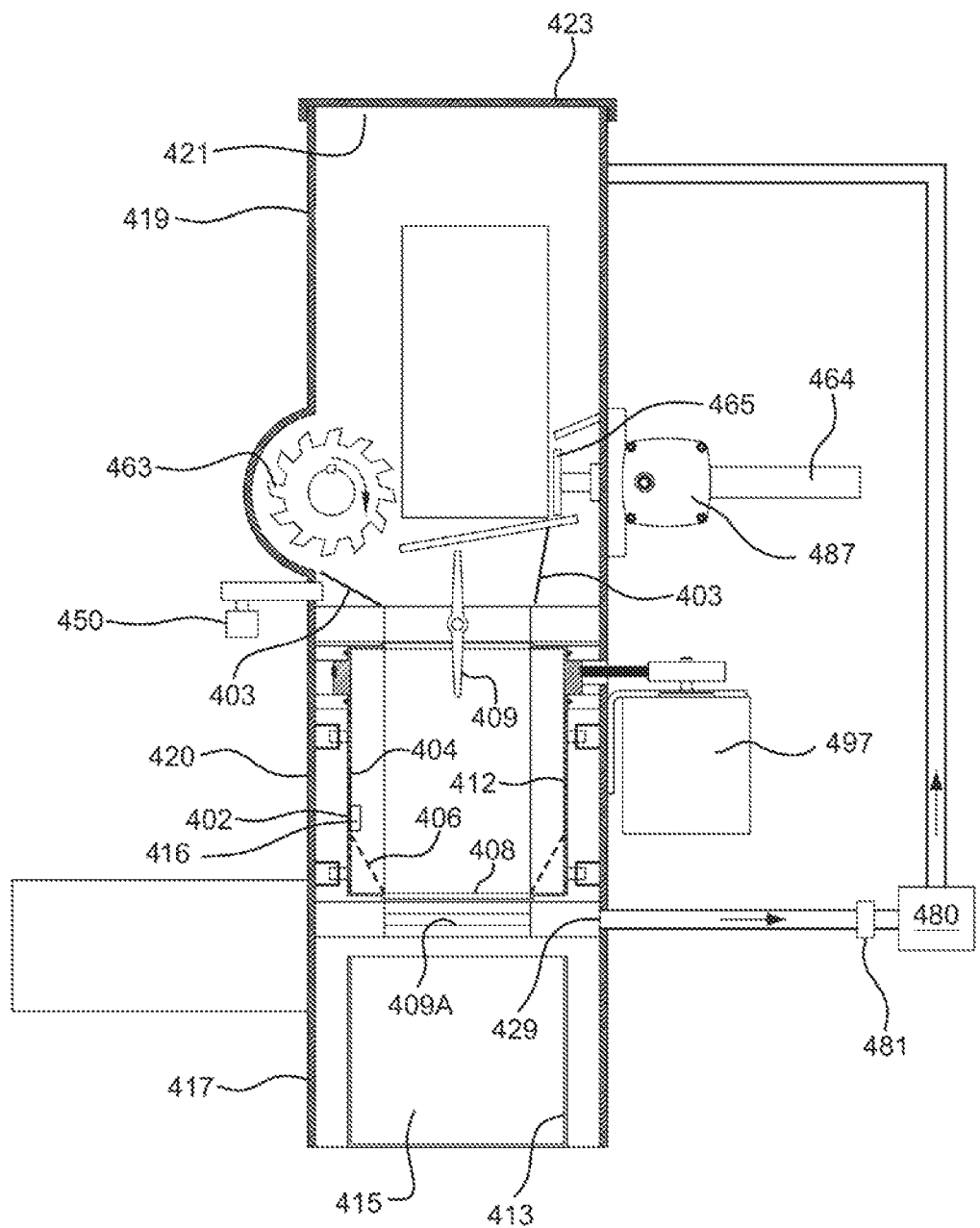
FIGS. 12A and 12B are schematic views of apparatus for microwave treatment of medical waste, the apparatus having a grinder to grind the medical waste prior to remediation.
Figure 12B:
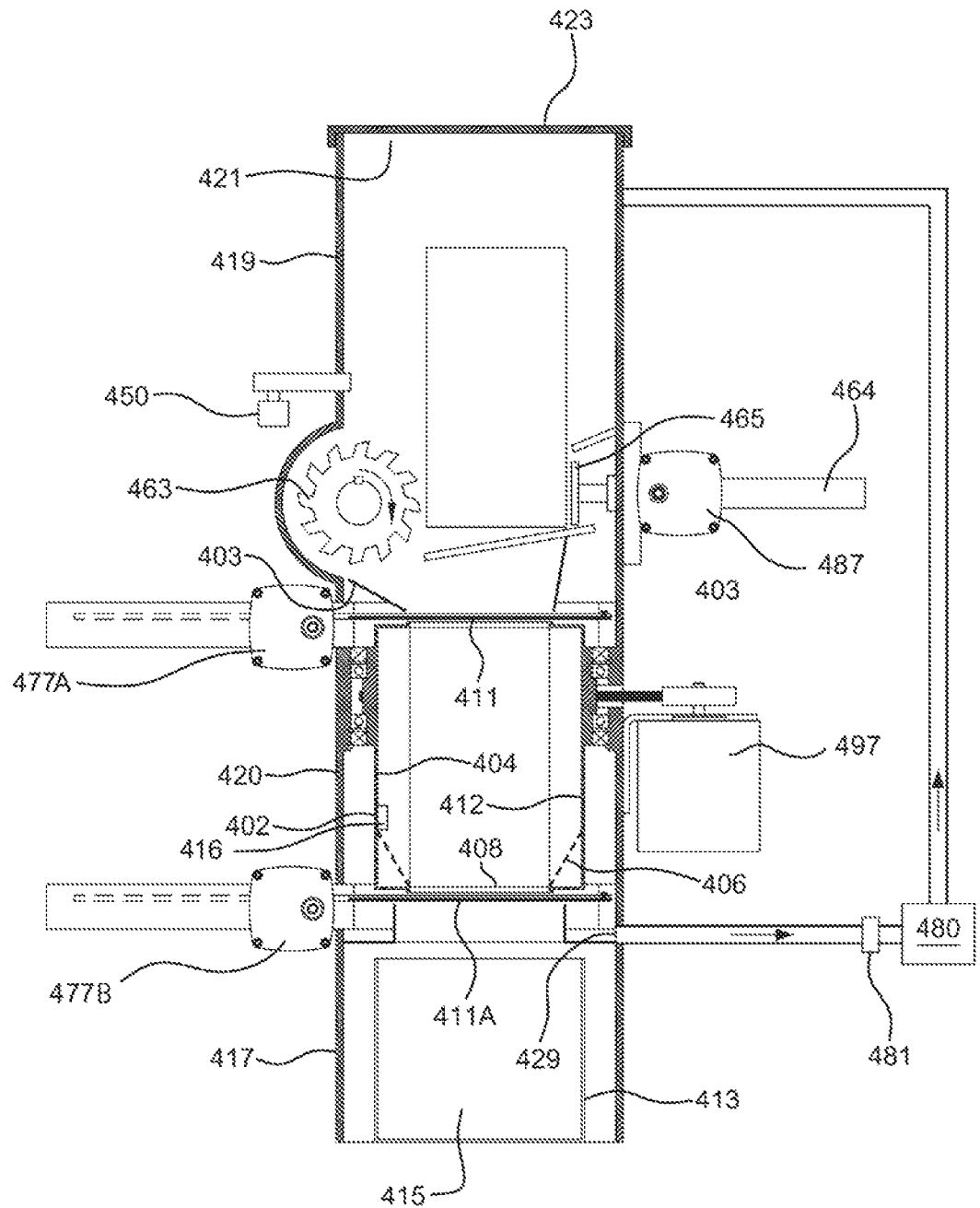

Another system of the invention is illustrated in FIGS. 12A and 12B, which shows a remediator 400. Remediator 400 shares many of the same elements as remediator 300. The remediator 400 includes a first chamber 419, a remediation chamber 420, and a finish chamber 417.

The first chamber 419 includes an opening 421 into which medical waste can be introduced. The opening is closed by a lid 423. As shown in FIGS. 12A and 12B, the lid 423 is a snug fit closure. Other closures such as the ones described above with respect to the remediator 300 are also contemplated.

The first chamber 419 includes a motor 487 and a piston arm 464. The piston arm 464 extends through the side of the first chamber 419 to a piston head 465. As shown, the piston head 465, in its fully retracted position, is offset from the wall of the first chamber 419. The offset allows for full decontamination of the piston head 465. In operation, the piston head 465 directs the medical waste in the first chamber 419 toward a grinder 463 that grinds the medical waste prior to remediation. The medical waste is also guided by a subfloor 403, which aids in preventing the medical waste from passing through the first chamber 419 without being reduced in size.

The grinder 463 may be driven by at least one motor. The grinder 463 preferably can cut steel (e.g., syringes) and other similar materials that are commonly found in medical waste. The grinder 463 may be a commercial off the shelf grinder or custom designed grinder.

Preferably, the grinder 463 produces ground medical waste in which substantially all of the medical waste is less than about 1 inch in size, more preferably less than about 0.5 inch in size, and most preferably less than about 0.25 inch in size. The smaller size allows for better treatment of the medical waste. For example, a smaller size allows for remnant liquids trapped in partially cut syringes, etc. to be remediated more effectively.

As shown, the first chamber 419 also includes an angled floor (also referred to as "sub-floor") 403 for directing the ground medical waste to a remediation chamber 420, which is in fluid communication with the first chamber 419. The first chamber 419 and the remediation chamber 420 may be separated by, for example, a fluid permeable layer. The first chamber 419 and the remediation chamber 420 may be separated by, for example, a valve. As shown in FIG. 12A, the valve is a butterfly valve 409. As shown in FIG. 12B, the valve is a gate valve 411. Other valves are contemplated and may be selected based on, for example, the ability of the valve to hold the weight of the medical waste. Preferably, the valve, when closed, allows fluid transfer between the remediation chamber 420 and the first chamber 419, but prevents solids from passing between the two chambers. For example, the valve may be a mesh gate valve.

The remediation chamber includes a waste receptacle 402, which houses the ground waste during remediation. The waste receptacle 402 may be made of any of the same materials as described for vessel 2. PTFE is the preferred material for the waste receptacle 402 due to its microwave transparency, chemical inertness and thermal durability (to over 280° C.). The waste receptacle 402 includes a wall 404 and a base 406. The base 406 is angled to an opening 408, which may be an adjustable opening such as the adjustable opening 108 of remediator 100 described above. The chamber may further comprise one or more supports 405.

As shown, the wall 404 is cylindrical, but other shapes can be utilized. The wall 404 can be perforated with a plurality of holes 412 to permit MAF ingress and egress. The holes 412 in the waste receptacle wall 404 can be spaced randomly, asymmetrically or spaced evenly. The size of the holes or perforations depend on the desired microwave frequency. For example, for a microwave frequency from about 2 to about 3 GHz, the size of the holes or perforations are preferably greater than about 1 cm, more preferably greater than about 2 cm, and most preferably greater than 3 cm.

The waste receptacle 402 may be of various sizes, with the determinative factor on size being the waste receptacle's ability to fit into the remediator 400. The waste receptacle 402 can have a circular, triangular, or rectangular cross section, and it can have a cross section of any other symmetrical or asymmetrical shape. A cylindrical waste receptacle may have, for example, dimensions of about 12 cm diameter by about 20 cm depth, with a resultant volume capacity slightly over 2 liters. A cylindrical waste receptacle of that size can hold approximately 1.4 kg of medical waste.

Preferably, the remediation chamber 420 includes a means for rotating the medical waste to allow for a more even application of the microwave radiation to the medical waste in the waste receptacle 402. For example, the waste receptacle 402 can be rotatable. Preferably, the rotation is at a slow spin, generally from about 2 to about 20 revolutions per minute ("rpm"). The rotation can be accomplished by having the waste receptacle 402 on a rotating plate (e.g. a turntable), having a rotating arm attached to the waste receptacle 402, or by other means known by those skilled in the art. Preferably, the waste receptacle includes a bar across the bottom to assist in forcing the medical waste to the sides of the waste receptacle 402 during rotation.

The remediation chamber 420 includes a drain 429 for draining a microwave active fluid, which is used in remediating the medical waste 4. The drain is in fluid communication with a MAF reservoir 480. After remediation, the MAF can be drained from the remediation chamber, run through a filter 481, and then stored in a MAF reservoir 480 until it is needed again. When it is needed, the MAF can be pumped from the MAF reservoir 480 to the first chamber 419 though piping, conduits, or any other manner known to one skilled in the art. The remediation chamber further comprises a motor 497 for filling and draining of liquid.

The remediation chamber 420 may include one or more temperature sensors as described with respect to remediator 100. The remediation chamber 420 may include one or more liquid sensors 416 as described with respect to remediator 100.

The remediator 400 also includes at least one magnetron 450 for delivering microwave radiation to at least the remediation chamber. The remediator may have multiple (e.g., 2-6) magnetrons. In a particular embodiment, the subfloor 403 is microwave transparent (e.g., made of PTFE) and the magnetron is placed to the outside of the subfloor 403. In the event that the subfloor 403 is made of metal, the magnetron is placed in a different location. As shown, the magnetron 450 is centrally located on the remediator 400 such that microwave radiation can be delivered to the remediation chamber 420 and the first chamber 419. The remediator 400 may also include a waveguide for directing the microwave radiation into at least the remediation chamber 420, and preferably into the remediation chamber 420 and the first chamber 419. More than one waveguide may be used.

The remediator 400 also includes a finish chamber 417 for receiving remediated medical waste from the remediation chamber 420. The finish chamber 417 is, as shown, separated from the remediation chamber 420 by a non-permeable layer such as a valve or door. The valve or door may be part of the remediation chamber 420, part of the finish chamber 417, or integral to both the remediation chamber 420 and the finish chamber 417. As shown in FIG. 12A, the valve is a butterfly valve 409A. As shown in FIG. 12B, the valve is a gate valve 411A. In a particular embodiment, as shown in FIG. 11B, the operation of these valves and movement of material between the upper and lower chambers and between the lower chamber and waste receptacle may be controlled by motors 477A and 477B respectively.

The finish chamber 417 includes a waste container 413 for receiving the remediated medical waste. Preferably, the waste container 413 is removable through an opening 415. The opening 415 may be at the bottom or the finish chamber 417 or on one of the sides of the finish chamber 417.

Remediator 400 and its associated components may be automated and/or controlled by a controller as described with respect to remediator 100.

In operation, remediator 300 operates in a similar manner as remediator 400, and thus the operation of the two is described together. With the valve 309, 311, 409, 411 between the first chamber 319, 419 and the remediation chamber 320, 420 closed, a user or mechanical device lifts the lid 323, 423 and inserts medical waste into the first chamber 319, 419. The lid 323, 423 is closed and, if present, the latch 327 is closed. MAF from the MAF reservoir 380 or 480 is added to the first chamber so as to fill the first chamber 319, 419 and the remediation chamber 320, 420. Thus, the MAF, the remediation composition is dispensed from a reservoir for immersing medical waste. The piston head 365, 465 presses the medical waste into the grinders 363, 463 (in remediator 300, the piston head 365 pushes the medical waste vertically into the grinders 363, while in remediator 400, the piston head 465 pushes the medical waste horizontally into the grinder 463). The grinders 365, 465 grind the medical waste, thereby reducing the size of it.

MAF is added into either the first chamber 319, 419 or the remediation chamber 320, 420, and allowed to fill up all of the remediation chamber 320, 420 and a portion of the first chamber 319, 419.

The MAF can be added before, during, or after the addition of the medical waste. For example, the MAF may be added before the medical waste is placed in the first chamber 319, 419. The MAF may be added after the medical waste has been placed in the first chamber 319, 419, but before the medical waste is compacted by the piston head 365, 465 and/or ground by the grinders 363, 463. Adding the MAF before grinding aids in the grinding. The MAF may be added after the medical waste has passed through the grinders 363, 463.

After the medical waste has been ground, it is deposited into the remediation chamber 320, 420. Once the ground medical waste and the MAF are in the remediation chamber, microwave radiation is applied to the remediation chamber 320, 420 from the magnetron 350, 450 to remediate the medical waste. The microwave radiation can also be applied to the first chamber 319, 419 that is filled or partially filled with the MAF. The application of the microwave radiation to the first chamber 319, 419 aids in sterilizing the first chamber 319, 419, including the grinder heads.

After the medical waste has been remediated, the MAF is drained from the first chamber 319, 419 and the remediation chamber 320, 420 through drain 329, 429. The used MAF is run through a filter 381, 481 and stored in a MAF reservoir 380 or 480 for later use. The remediated medical waste may be subjected to a spin cycle (i.e., a cycle similar to the spin cycle of a laundry washing machine) in the waste receptacle 302, 402 to remove MAF that is still in the medical waste after the remediation chamber 320, 420 has been drained.

The remediated medical waste may then be transferred to the waste container 313, 413 of the finish chamber 317, 417 by the opening of the valve 309A, 311A, 409A, 411A. To aid in the removal of the waste from the remediated waste, forced air may be introduced into the first chamber 319, 419, remediation chamber 320, 420, and/or finish chamber 317, 417.

The waste container 313, 413 can then be removed and the remediated medical waste disposed of with municipal waste.

Many other design variations are possible in the above-described embodiments, such that the initial cutter-piston action may be up or down, horizontal or vertical, and/or in the form of cutter-blades or grinders. The remediation chamber can be top opening, side opening, or bottom opening. With side and bottom opening, proper seals would be necessary to prevent leakage of the MAF. An additional fill/drain cycle may be used to further cool the MAF after the remediation. The MAF reservoir may be equipped with external, aerodynamic flutes, and a small fan may be provided for its further cooling. The filter trap process for retaining the solids from the MAF after remediation may be automated. Multiple magnetrons may be used. Single-mode and multimode microwave functionality may be introduced. Thus, the step of delivering the step of delivering the microwave radiation comprises an intermittent delivery of the microwave radiation.

Figure 16:
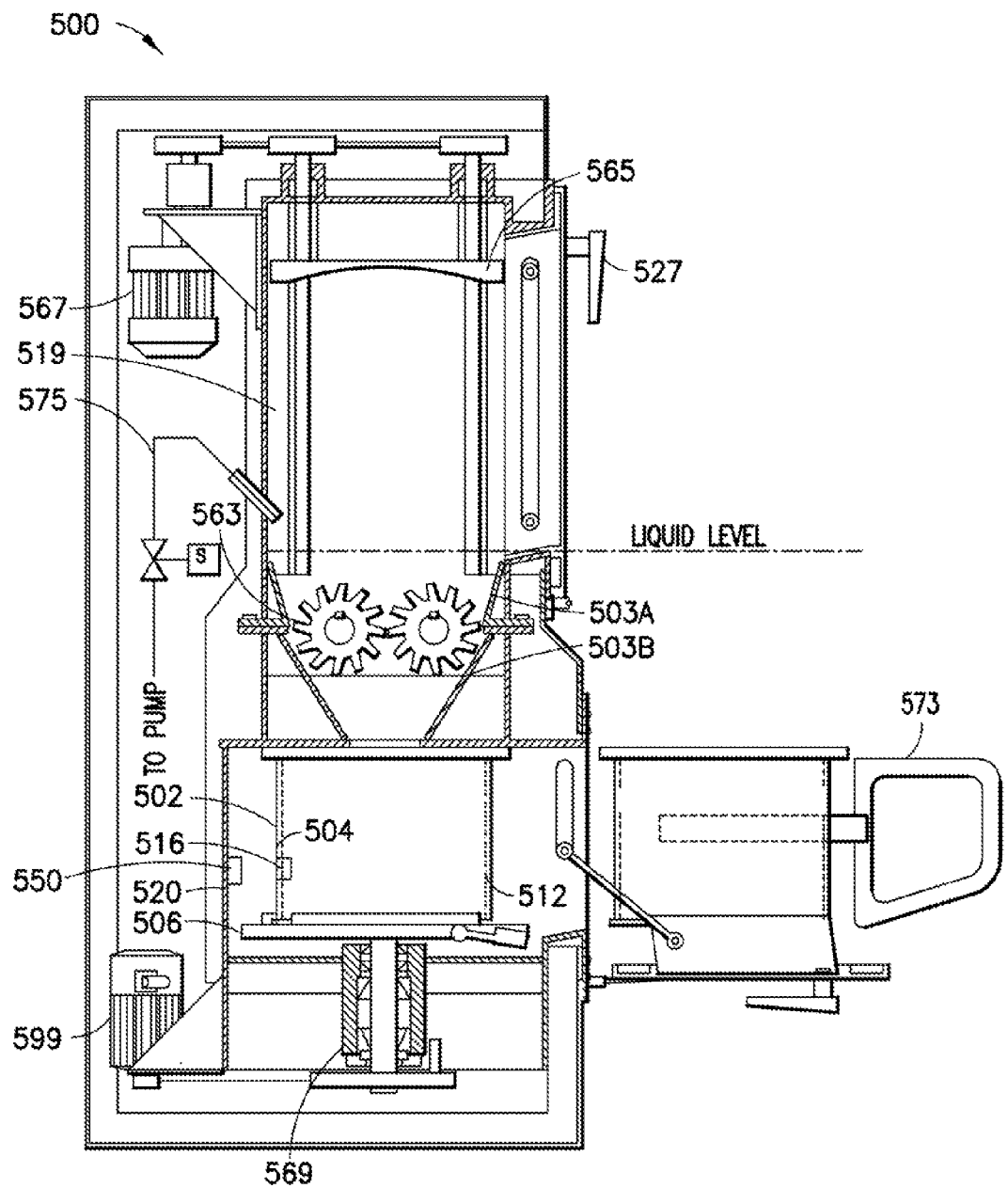
FIG. 16 is a side view of another apparatus for microwave treatment of medical waste.

Another system of the invention is illustrated in FIG. 16, which show a remediator 500. As will be set forth in further detail below, in contrast to remediators 300 and 400, the remediator 500 is front loading, does not contain a valve separating the upper and lower chamber and requires less than about 70 liters of MAF in contrast to about 200 liters of MAF. The remediator 500 includes a first chamber 519. As noted above, the first chamber 519 in contrast to remediators 300 and 400 is front loading. Waste is introduced by turning the knob 527 to create an opening and corresponds to step 202 set forth in Table 1 and FIG. 8C. The knob 527 also serves as a latch.

As shown in FIG. 16, on top of the remediator is a waste press 565 that acts as a means for directing the medical waste introduced in the first chamber 519 to two cutting wheels 563 that act as a rotatable cutting assembly and comminute the medical waste prior to remediation set forth in Table 1 and FIG. 8C. The waste press may be flush with one or both sides of the remediator and may be driven by at least one motor.

The cutting wheels 563 may be driven by at least one motor. The cutting wheels 563 work in a manner similar to the schemes set forth for cutting wheels 363 and 463. Further, the blades of the cutting wheels serve to control the flow of liquid from the first chamber 519 to the remediation chamber 520 and may prevent solids from passing between the two chambers. The blades of the cutting wheels may be lubricated with a cutter spray lubricator 575.

As shown, the first chamber 519 also includes an angled floor containing two components 503A and 503B for directing the ground medical waste to a remediation chamber 520, which is in fluid communication with the first chamber 519. The first chamber 519 and the remediation chamber 520 may be separated by, for example, a fluid permeable layer.

MAF from an MAF reservoir may be added to either the first chamber 519 or the remediation chamber 520 and allowed to fill up all of the remediation chamber 520 and a portion of the first chamber 519 and corresponds to steps 206 set forth in Table 1 and FIG. 8C. The MAF may be added before or after the grinding step.

The remediation chamber 520 includes a receptacle 502, which houses the ground waste during remediation. The receptacle 502 may be made of any of the same materials as described for vessel 2. PTFE is the preferred material for the waste receptacle 502 due to its microwave transparency, chemical inertness and thermal durability (to over 280° C.). The receptacle may also be made of metal, which is opaque to microwaves. The receptacle 502 includes a wall 504 and a base 506. The receptacle may be removable. The container may be unlocked via a handle 573. The wall 504 can be perforated with a plurality of holes 512 to permit MAF ingress and egress. The holes 512 in the waste receptacle wall 504 can be spaced randomly, asymmetrically or spaced evenly. If the receptacle is made of material that is not transparent to microwaves, such as metal, then the size of the holes or perforations depends on the desired microwave frequency. For example, for a microwave frequency from about 2 to about 3 GHz, the size of the holes or perforations are preferably greater than about 1 cm, more preferably greater than about 2 cm, and most preferably greater than 3 cm.

The waste receptacle 502 may be of various sizes, with the determinative factor on size being the waste receptacle's ability to fit into the remediator 500. The waste receptacle 502 can have a circular, triangular, or rectangular cross section, and it can have a cross section of any other symmetrical or asymmetrical shape. A cylindrical waste receptacle may have, for example, dimensions of about 12 cm diameter by about 20 cm depth, with a resultant volume capacity slightly over 2 liters. A cylindrical waste receptacle of that size can hold approximately 1.4 kg of medical waste.

The remediation chamber 520 may include one or more temperature sensors as described with respect to remediator 100. The remediation chamber 520 may include one or more liquid sensors 516 as described with respect to remediator 100. Medical waste is deposited into the remediation chamber 520 after the medical waste is ground.

The remediator 500 may also include at least one magnetron for delivering microwave radiation to at least the remediation chamber as set forth in step 208 of FIG. 8C and Table 1. More than one magnetron may be used. In a particular embodiment, two-six magnetrons are used. In a preferred embodiment, four magnetrons are used. In yet another preferred embodiment, the four may be placed at the four directions (north, south, east, west) on the four walls of the remediation chamber 520, for example ⅓ of the way up each wall. The remediator 500 may also include a waveguide for directing the microwave radiation from the magnetron into at least the remediation chamber 520, and preferably into the remediation chamber 520 and the first chamber 519. More than one waveguide may be used. As previously noted, the remediator contains a slanting floor 503. In a particular embodiment, the slanting floor 503 is microwave transparent (e.g., made of PTFE) and at least one magnetron is placed to the outside of the slanting floor. In the event that the slanting floor 503 is made of metal, the magnetron is placed in a different location. The microwave radiation can also be applied to the first chamber 519 that is filled or partially filled with the MAF.

The remediation chamber 520 may also contain a liquid cooling supply 569 that serves to cool the liquid in the remediator as set forth, for example in Step 210 of FIG. 8C and Table 1. The cooling supply may be controlled by one or more motors 599.

After the medical waste has been remediated, the MAF may be drained (see step 212 of FIG. 8C and Table 1) into the reservoir. The remediated medical waste may be subjected to a spin cycle (see step 214 of FIG. 8C and Table 1) in the waste receptacle to remove MAF that is still in the medical waste after the remediation chamber has been drained. The waste receptacle may be subsequently detached from the remediator and the contents may be emptied.

Thus, the description of the specific embodiments in the foregoing and in the examples below will fully reveal the general nature of this invention, such that others can, through application of current and extant knowledge, readily adapt the above-described specific embodiments without departing from the spirit and scope of the present invention. Such adaptations are intended to be understood within the meaning and range of equivalents of the disclosed embodiments, and the descriptions in this invention are for the purpose of illustration and not limitation.

Example 1

Microwave Activity

Microwave activity in a liquid molecule is dependent upon the presence of a strong dipole in the molecule. Thus, water, a small, polar molecule, displays significant microwave activity. Certain MALs display far greater microwave activity, as measured by the temperature (heating) effect, than water. Among these are poly(glycols), such as poly(propylene glycol) PPG or PEG. Their microwave activity, in comparison to that of water, can be illustrated by the temperature effect seen in the following example.

Seventy mL of de-ionized water were taken in a 100 mL beaker and placed at the midpoint of the platen in a 1.2 KW kitchen microwave (Sears KENMORE® Model 721.62462201) (Registered trademark of KCD IP, LLC, Hoffman Estates, Ill.) at an initial 25° C. The microwave was run on high for 2.5 minutes. The identical process was then carried out for 70 mL of PEG (molecular weight, $M_n$, 285-315). It was seen that the PEG attained a temperature of 257° C. but did not begin boiling, whereas the water achieved 97° C. and just started to boil.

The MAF compositions listed in Table 2 were irradiated using a Sears KENMORE® Model 721 62462 microwave oven (1.2 KW, 2.45 GHz, 13.5 Amperes). The MAL, where present in the MAF compositions, was poly(ethylene glycol) $M_n$=200-415 ("PEG"). The viscosity modifying agent, where present in the MAF compositions, was poly(ethylene oxide), $M_w$ 200,000 ("PEO"). The microwave enhancer, where present in the MAF compositions, was activated carbon, DARCO® (Registered trademark of Norit Americas, Inc.), 20 to 40 mesh ("activated-C"). Each composition comprised 50 mL fluid in a 100 mL beaker. All composition percentages are in wt. %. All were stable milk-like sols. The microwave activity of the MAF are illustrated, in comparison to that of water, in Table 2.

TABLE 2

| | | | | |
|---|---|---|---|---|
| Microwave activity of MAF compositions | | | | |
| MAF Composition | Temp. (° C.), initial | Temp. (° C.), at 60 sec | Temp. (° C.), at 120 sec | Temp. (° C.), at 157 sec |
| Tap water | 24.0 | 97.2 | 100, boiling | 100, boiling |
| PEG | 24.0 | 178.0 | 239.3 | 256.5 |
| 0.5% activated-C, 1% PEO in PEG | 24.0 | 180.5 | 233.5 | 255.0 |
| 1% SiC, 1% PEO in PEG | 24.0 | | | 274.3, boiling |
| 5% activated-C, 1% PEO in PEG | 24.0 | | | 325.1, boiling |
| 2.5% activated-C, 1% PEO in PEG | 24.0 | | | 311.3, boiling |
| 5% $Fe_3O_4$, 1% PEO in PEG | 24.0 | | | 271.0 |

Examples 2 to 7 illustrate the medical waste remediating capability of MAFs of the invention.

Example 2

AOAC (Association of Official Analytical Chemists) Sporicidal Test

The AOAC Sporicidal Test, an industry-standard test, was used to determine the remediation capability of an MAF of the present invention. The MAF used in these tests had the following composition: MAL=PEG, $M_n$ 200-415, b.p. >275° C. (Sigma-Aldrich); viscosity modifying agent=PEO $M_v$ 200,000 (Sigma-Aldrich), 1 wt. % in PEG; microwave enhancer=activated-charcoal ("decolorizing", Sigma-Aldrich), 1 wt. % in PEG. The MAF was prepared by dissolving the PEO in the MAL at 105° C. with stirring over 1.5 hours. The resulting solution was allowed to cool to 80° C. The activated-charcoal was added to the PEO/PEG solution with stirring at 80° C. for an additional 0.5 hour to form a sol. The sol was then allowed to cool to room temperature.

For each test, 10 mL of the MAF was placed in each of 6 sterile tubes. Five *Bacillus subtilis* AOAC Carriers (Porcelain Penicylinders or Black Silk Suture Loops) were inoculated into each of the six tubes. The preparation of test materials and the actual testing followed AOAC procedures required for a full AOAC Sporicidal Test. The tubes of MAF with carriers and without closures were placed in a 1.5 L PYREX® glass beaker, which was covered with a PYREX® glass plate. The covered beaker with carrier tubes was placed in a Sears KENMORE® microwave oven (Model 721.62461, 1200 Watts, 2.45 GHz). The covered beaker was placed at the end of one of the tripod legs in the microwave oven's rotating glass plate (i.e., off center). The covered beaker and its contents were exposed to microwave irradiation for a predetermined time, as noted in the results (Table 3) below. The tubes were positioned in the beaker with the bottoms pointing to the periphery of the beaker during the microwave exposure.

Following microwave exposure, the beaker was removed to a certified laminar flow bench. Exposed carriers were transferred to individual tubes of fluid thioglycolate medium. After a 30-minute neutralization period, carriers were subcultured from the first tube to a second tube of fluid thioglycolate medium. Both sets of subcultured tubes were incubated at 37° C. and observed for growth (+) or no growth (−). During exposure, suture loops disintegrated in some cases. Consequently, for subculturing in those cases where loops disintegrated, a standardized loop (4 mm) was used to subculture from the exposed tube and also for the second sub-cultured tube.

The MAF of the present invention achieved spore kill of *B. subtilis* in a shorter period than other non-traditional sporicidal products.

Results of the Sporicidal Test are listed in Table 3 below.

TABLE 3

AOAC Sporicidal Screening Test Results For An MAF With (*Bacillus subtilis* ATCC 19659),

| Test No. | Test Date | Exposure Time | Carriers/No | Results | Results |
|---|---|---|---|---|---|
| 1A | Feb. 10, 2007 | 15 min | P-30 | 0+/30 | 0+/30 |
| 2A | Feb. 14, 2007 | 15 min | S-30 | 3+/30 | 3+/30 |
| 3A | Feb. 19, 2007 | 11 min | P-30 | 0+/30 | 0+/30 |
| 4A | Feb. 24, 2007 | 5 min | P-30 | 0+/30 | 0+/30 |
| 5A | Mar. 3, 2007 | 17 min | S-30 | 1+/30 | 1+/30 |
| 6A | Mar. 19, 2007 | 19 min | S-30 | 0+/30 | 0+/30 |

(LEGEND: P = Penicylinder; S = Suture Loops.)
(Results quoted as Number positive/Number exposed. Thus 1+/30 indicates 1 positive result out of 30 exposed samples.)

Example 3

MAF Remediation of Bacteria

To determine the effect of MAF treatment on bacteria, substrates were inoculated with bacterial cultures to form infectious medical wastes ("IMW") as described as below. The IMW were treated with a quantity of the MAF prepared as in Example 2, and microwave irradiated. The treated and irradiated IMW were tested for biological activity as described below. MAF was also prepared as described in Example 2.

Accordingly, preparation of the IMW began by collecting substrates (samples), which included: bandages, cotton gauze, cotton balls, self-adhesive bandages (pad portion and adhesive portion), cotton plugs, latex and vinyl gloves, swabs, cultures, plastic syringes (plunger and receptacle part), metal syringe needles, disposable scalpels and other small surgical instruments. All non-metallic substrates were cut into strips of 1 cm by 3 cm. Metallic substrates (scalpels, syringe needles) were taken as is. In addition to the non-metallic and metallic substrates, commercially procured microbe sample strips and/or pellets (retained in open vials) (*B. subtilis*, MicroBiologics, St. Cloud, Minn. and Fisher Scientific, Pittsburgh, Pa.) were also used as substrates. Finally, a liquid content of at least 5 wt. %, absorbed into the cotton swabs and plugs, was ensured in order to emulate actual medical waste samples as close as possible. This was done by soaking dry swabs with a 5 wt. % liquid, such as, for example, water or a bacterial culture medium.

Bacteria for use in the present example included one or more of the following: *Bacillus cereus*, *B. subtilis* (aerobic bacteria, cultures procured from ATCC) (American Type Culture Collection, Manassas, Va.); *Clostridium beijerinckii* (anaerobic bacterium, cultures procured from ATCC), *B. anthracis* V1B, and *Mycobacterium tuberculosis* H37Rv (pathogenic bacteria, cultures at Center for Biodefense, University of Medicine & Dentistry of New Jersey ("UMDNJ", New Jersey Medical School), Newark, N.J.). For the *Bacillus* and *Clostridium* species, only spores were used for all tests. Spores are much hardier than the bacteria, and the killing of spores is more definitive proof of remediation than killing of bacteria. The work with the pathogenic organisms was carried out in a hood in a BSL-3 laboratory at the Center for Biodefense, Newark, N.J.

The porous or absorbent substrates, such as gauze and cotton plugs, were soaked in the bacterial culture. The non-absorbent substrates, such as the gloves and the plastic portion of self-adhesive bandages (such as BAND-AIDS®), were infected by pouring about 3 mL of liquid culture onto them, and allowing this to partially dry (about 20 mins in air). Syringe needle tips and the top part of syringes were simply filled with the culture. The culture was laid on metallic parts such as scalpels, and allowed to dry under incubation conditions. The infected parts were marked with circular markings using a microbiological marker pen. The medical wastes were enclosed in a perforated TEFLON® bag or envelope, for ease of handling and also to emulate practical use of the invention with "red bags". (TEFLON® is the material of choice for use in microwaves because it is substantially microwave-transparent and is chemically inert and non-stick.) In addition to the above, commercially available *B. subtilis* "microbe sample strips" were also included as part of the IMW.

The bacterial-inoculated IMW was then immersed in MAF in a cylindrical crystallizing dish made of borosilicate glass. The weight of the IMW was 400 g, and 600 mL of the MAF was used for immersion, providing a 1/1.5, w/v IMW/MAF ratio. A flat, circular borosilicate glass cover, or, alternatively, an inverted PYREX® backing dish, was placed loosely on top of the crystallizing dish. The crystallizing dish was then placed in a Sears KENMORE® microwave oven (Model 721.62461, 1.2 KW, 2.45 GHz), such that it was centered on the midpoint of one of the turntable tripod legs, i.e., about 10 cm off center. The microwave was then run on the "high" setting for 20 minutes. The temperature was monitored with a LUXTRON® One fluoro-optic sensor. The temperature observed at 10 min. was 235° C. The oven was switched off for 60 seconds ($10^{th}$ to $11^{th}$ minute). It was run again on "high" from the $12^{th}$ through the $17^{th}$ minute, switched off again from the $17^{th}$ to the $18^{th}$ minute, and run again through 20 minutes. The final temperature observed was 237° C. No fumes or other external manifestation of reactions or other processes were visible at the end of the microwave run. The dish and cover were then removed from the microwave using oven mitts and allowed to cool in ambient air for 15 minutes. The IMW was press-strained and then cultured, as described in the next paragraph.

For growth of cultures, a minimum of 96 hours (4 days) was allowed. Cultures were grown using Miller LB (Luria-Bertani) broth and LB agar Difco medium (Fisher Scientific), at 30° C., with Gram stain, for the aerobic organisms, and brain-heart infusion agar for the anaerobic cultures. Each experiment was carried out in triplicate.

The experiments in this example were preformed in the same manner and with the same materials as Example 3, except that in this Example, actual "red-bag medical wastes" (blood-soaked bandages, needles, etc.) were used as samples in place of the bacteria-inoculated IMW prepared as described in Example 3. The red-bag medical wastes were obtained from the UMDNJ Hospital, Newark, N.J. Tests were conducted in the Biosafety Level ("BSL")-3 facility at the Center for Bio-Defense, Newark, N.J. "Sample" runs, with microwave irradiation of the red-bag medical wastes immersed in the MAF, are designated in Table 4 as "M". "Reference" runs, with immersion of the medical wastes in the MAF but no microwave exposure, are designated in Table 4 as "R". "Control" runs, with neither immersion of the medical wastes in the MAF nor microwave exposure, are designated in Table 4 as "C".

The results are summarized in Table 4. The results are the summary of more than 100 individual experiments, each run in triplicate. The Reference and Control runs showed profuse culture growth.

TABLE 4

Results from Examples 3, 4: Use of MAF to Remediate IMW and Actual Red-Bag Hospital medical wastes

| Serial # | Medical waste Type, weight | Organism | Run Type | Results @ 96 h | Results @ 14 d |
|---|---|---|---|---|---|
| 1. | IMW, 400 g | *Bacillus cereus* (aerobe) | M, 11 minutes | (−) | (−) |
|  | IMW, 400 g | " | C | (+) |  |
|  | IMW, 400 g | " | R | (+) |  |
| 2. | IMW, 400 g | *B. subtilis* (aerobe) | M, 13 minutes | (−) | (−) |
|  | IMW, 400 g | " | C |  |  |
|  | IMW, 400 g | " | R | (+) |  |
| 3. | IMW, 550 g | *B. cereus* | M, 15 minutes | (−) | (−) |
|  | IMW, 550 g | " | C | (+) |  |
|  | IMW, 550 g | " | R | (+) |  |
| 4. | IMW, 350 g | *B. cereus* | M, 7 minutes | (−) | (−) |
|  | IMW, 350 g | " | C | (+) |  |
|  | IMW, 350 g | " | R | (+) |  |
| 5. | IMW, 400 g | *Clostridium beijerinckii* (anaerobe) | M, 13 minutes | (−) | (−) |
|  | IMW, 400 g | *Clostridium beijerinckii* (anaerobe) | C | (+) |  |
|  | IMW, 400 g | *Clostridium beijerinckii* (anaerobe) | R | (+) |  |
| 6. | IMW, 2 kg | *B. cereus* | M, 19 minutes | (−) | (−) |
|  | IMW, 2 kg | " | C | (+) |  |
|  | IMW, 2 kg | " | R | (+) |  |
| 7. | IMW, 300 g | *Bacillus anthracis* V1B (pathogen) | M, 13 minutes | (−) | (−) |
|  | IMW, 300 g | *Bacillus anthracis* V1B (pathogen) | C | (+) |  |
|  | IMW, 300 g | *Bacillus anthracis* V1B (pathogen) | R | (+) |  |
| 8. | IMW, 300 g | *Mycobacterium tuberculosis*, H37Rv (pathogen) | M, 13 minutes | (−) | (−) |
|  | IMW, 300 g | *Mycobacterium tuberculosis*, H37Rv (pathogen) | C | (+) |  |

TABLE 4-continued

Results from Examples 3, 4: Use of MAF to Remediate
IMW and Actual Red-Bag Hospital medical wastes

| Serial # | Medical waste Type, weight | Organism | Run Type | Results @ 96 h | Results @ 14 d |
|---|---|---|---|---|---|
| | IMW, 300 g | *Mycobacterium tuberculosis*, H37Rv (pathogen) | R | (+) | |
| 9. | "Red bag medical wastes", 350 g | Varied bacteria and viruses present in hospital medical wastes | M, 13 minutes | (−) | (−) |
| | "Red bag medical wastes", 350 g | Varied bacteria and viruses present in hospital medical wastes | C | (+) | |
| | "Red bag medical wastes", 350 g | Varied bacteria and viruses present in hospital medical wastes | R | (+) | |

ABBREVIATIONS:
For medical waste Type:
IMW = infected medical waste, mixed medical waste prepared as described above
For Run Type column:
R = "Reference", immersion in MAF but no microwave exposure;
C = "Control", no microwave liquid and no microwave exposure.
M = Microwave exposure run, exposure time given.
For Results column:
(+) = growth.
(−) = no growth.
h = hours
d = days

COMPARATIVE EXAMPLES

Comparative Example 5

Use of PEG to Remediate IMW

The experiments in this example were preformed in the same manner and with the same materials as Example 3, except that the IMW was immersed in PEG only, and not the fully formulated MAF as described in Example 3. Thus, no microwave enhancers and no viscosity modifying agents were added to the MAL. "Sample" runs, with microwave irradiation of the IMW immersed in the MAL, are designated in Table 5 as "M" (for "microwave"). "Reference" runs, with immersion of the IMW in the MAL but no microwave exposure, are designated in Table 5 as "R". "Control" runs, with neither immersion of the IMW in the MAL nor microwave exposure, are designated in Table 5 as "C".

TABLE 5

Summary Results Of Example 5: PEG
Only As The MAF To Remediate IMW

| Serial # | Medical waste Type, weight | Organism | Run Type | Results @ 96 h | Results @ 14 d |
|---|---|---|---|---|---|
| 10. | IMW, 400 g | *Bacillus cereus* (aerobe) | M, 18 minutes | (−) | (−) |
| | IMW, 400 g | *Bacillus cereus* (aerobe) | C | (+) | |
| | IMW, 400 g | *Bacillus cereus* (aerobe) | R | (+) | |
| 11. | IMW, 400 g | *B. subtilis* (aerobe) | M, 20 minutes | (−) | (−) |
| | IMW, 400 g | *B. subtilis* (aerobe) | C | (+) | |
| | IMW, 400 g | *B. subtilis* (aerobe) | R | (+) | |
| 12. | IMW, 400 g | *Clostridium beijerinckii* (anaerobe) | M, 22 minutes | (−) | (−) |
| | IMW, 400 g | *Clostridium beijerinckii* (anaerobe) | C | (+) | |
| | IMW, 400 g | *Clostridium beijerinckii* (anaerobe) | R | (+) | |

ABBREVIATIONS:
For medical waste Type:
IMW = infected medical waste, mixed medical waste prepared as described above.
For Run Type column:
R = "Reference", immersion in MAF but no microwave exposure;
C = "Control", no microwave liquid and no microwave exposure.
M = Microwave exposure run, exposure time given.
For Results column:
(+) = growth.
(−) = no growth.
h = hours
d = days It is seen that while PEG alone is able to achieve remediation, the microwave irradiation times are significantly longer than those for the fully formulated MAF of the present invention, as seen in the results presented in Table 5. Thus, the fully formulated MAF of the present invention is superior to PEG alone.

Comparative Example 6

Comparison of the Present Invention with Standard Steam Autoclaving

The microwave procedure as described in Example 3 was compared to autoclaving of the identical charge of 350 g of medical waste in a standard laboratory autoclave (All American "Electric Pressure Steam Sterilizer", Model No 25X, 120 V, 1050 W, 8.75 A, total capacity (volume) about. 10 L). The microwave procedure took 15 minutes to complete. The final temperature observed was 235° C. All samples showed no microbial growth after 14 days of culturing. The autoclave procedure took a total of 81 minutes, including the time required to reach the recommended steaming pressure of 20 psi and the recommended residence time of at least 20 minutes at this pressure. The autoclaved samples also showed no microbial growth after 14 days of culturing. The total energy expended in the microwave procedure was 0.279 KWH (kilowatt-hours), and that expended in the autoclave procedure was 1.418 KWH to obtain the same degree of sterilization. Thus, the microwave procedure expended just 19.7% of the energy of the autoclave procedure to obtain the same degree of sterilization. The microwave procedure also accommodated a sample of 700 g or larger, whereas the autoclave accommodated a maximum of 450 g, limited by volume of the container and supporting vessels within the autoclave.

Comparative Example 7

Comparison of Heat-Only Remediation Vs. Microwave-Based Remediation of the Present Invention The samples for this example comprised dry spores of *Bacillus subtilis* or *Bacillus cereus*, or cotton swabs inoculated with those spores.

In the microwave run, the samples were introduced into a microwave oven (Sears KENMORE® microwave oven (Model 721.62461, 1.2 KW, 2.45 GHz) and maintained at 150° C. for 1 minute or 3 minutes, immersed in 50 mL of MAF prepared according to Examples 2-4, held in a 100 mL beaker. MAF temperature was monitored carefully using LUXTRON® fiber-optic sensors. Two runs each of triplicates were carried out for all four sample types (dry *Bacillus subtilis*, dry *Bacillus cereus*, *Bacillus subtilis* cotton swab, *Bacillus cereus* cotton swab). Both exposure times, 1 min and 3 min, resulted in no microbial growth at 96 hours and 14 days for all four sample types.

In a corresponding, non-microwave, heat-only experiment, identically prepared samples were immersed in the same MAF (identical volume and identical vessel), but heated in a mineral oil bath, at a steady temperature of 150° C., for exposure times of 1, 3 and 7 minutes. Temperature was monitored with a thermometer immersed in the MAF. All three exposure times, i.e. 1, 3 and 7 minutes, showed significant microbial growth at 96 hours (TNTC, "too numerous to count").

In both the microwave and the non-microwave (heat-only) experiments, the following additional runs were also carried out: "Reference"—samples immersed in the MAF, but having no microwave or heat exposure; and "Control"—samples cultured directly, i.e. with no immersion in MAF and no microwave or heat exposure. All Reference and Control runs showed significant microbial growth, too numerous t count, at 96 hours, as expected, for all sample types.

These results demonstrate that the microwave chemistry effect in microwave remediation is not just a temperature effect. Microwaves cause disruption of the tertiary and quaternary structure of proteins in bacteria (or other organisms), "denaturing" them and thus eventually causing death of the organisms. The results show the unique and predominant effect of microwave chemistry as compared to non-microwave heat sterilization.

Example 8

Analyses of Post-Microwave Degradation/-Decomposition Products

One of the concerns with any remediation method for medical wastes is the possibility of potentially toxic or otherwise hazardous waste products. Table 6 summarizes results of a literature study conducted to identify possible degradation products that could result from the processes of the present invention. As just some examples of some of studies of direct relevance to the present invention are: (i) For analysis of products of burning of medical waste such as surgical gloves and cotton pads, Levendis, Y. A.; Atal, A.; Carlson, J. B.; del Mar Esperanza Quintana, M., "PAH and soot emissions from burning components of medical waste: examination/surgical gloves and cotton pads", *Chemosphere*, 42, 775-783 (2001); (ii) For semi-volatile and volatile compounds from pyrolysis and combustion of poly(vinyl chloride) (PVC) and polyethylene Aracil, I.; Font, R.; Conesa, J. A., "Semi-volatile compounds from the pyrolysis and combustion of polyvinyl chloride", *J. Anal. Applied Pyrolysis*, 74, 465-478 (2005); (iii) For studies on the thermal decomposition products of a variety of plastics specifically found in medical wastes and studies of "low-temperature" pyrolysis products of PEG Lattimer, R. P., "Mass spectral analysis of low-temperature pyrolysis products from poly(ethylene glycol)", *J. Anal. Applied Pyrolysis*, 56, 61-78 (2000). ("Pyrolysis" and "combustion" refer, respectively, to thermal breakdown in the absence and presence of oxygen.). The data from the literature study is compiled in Table 6.

TABLE 6

Summary Of Thermal Degradation (Pyrolysis And Combustion) Studies Of MAF Components And Medical wastes

A. PRODUCTS FROM POLY(ETHYLENE GLYCOL) (PEG)

A.1 Low Temperature Pyrolysis, 150 to 250° C.
PEG oligomers, HO—(—$C_2H_4$—O—)$_n$—H, n > 10 typically.
Oligomer of Ethyl ether, $C_2H_5$—O—(—$C_2H_4$—O—)$_n$—H, n > 10 typically.
A.2 Higher Temperature Pyrolysis, >250° C.
Other products, e.g. methyl, vinyl ethers, in oligomer form (n > 10 typically) as above.

B. FROM IMW ("RED BAG MEDICAL WASTES")

B.1 High temperature (1 000° C.) combustion, of latex gloves, sterile cotton pads, etc., all "red bag" medical wastes
Besides CO, $CO_2$, $NO_x$, main medical wastes are particulates (soot) and polynuclear aromatic compounds (PACs).
PACs:

From Latex: Naphthalene (most), phenanthrene (2$^{nd}$), acenaphthylene (3$^{rd}$), pyrene (4$^{th}$).
From Cotton: Acenaphthylene (most), naphthalene (2$^{nd}$), pyrene (4$^{th}$). But all much smaller quantities than from Latex.

C. FROM POLYETHYLENE (HDPE)

C.1 High temperature (500° C.) combustion
Mostly $CO_2$, CO. Alpha, omega- olefins, alpha-olefins, TABLE 6-continued Summary Of Thermal Degradation (Pyrolysis And Combustion) Studies Of MAF Components And Medical wastes n-paraffins other main products. E.g. ethylene, propylene, n-butane, 1,3-butadiene.
On the basis of this, it is expected that main products in our experiments would be expected to be oligo-ethylenes. We should also look out for aldehydes.
D. FROM POLY(VINYL CHLORIDE) (PVC)

D.1 At 500° C. (studied to 1000° C.)
Mainly $CO_2$, CO.
HCl produced which further reacts to give other products.
Methane, ethane, ethylene, benzene are other major products.

Using the information from Table 6 as a point of comparison, an analysis of the products (i.e., the medical waste and MAF after remediation), after 21 microwave runs, using the MAF prepared according to Example 2 were carried out, encompassing a wide variety of techniques, including spectroscopy (FTIR, $^{13}C$ and proton NMR, UV-Vis), mass spectrometry and chromatography. The present example summarizes these results. As the results show, no toxic or hazardous products were indicated.

Figure 13:
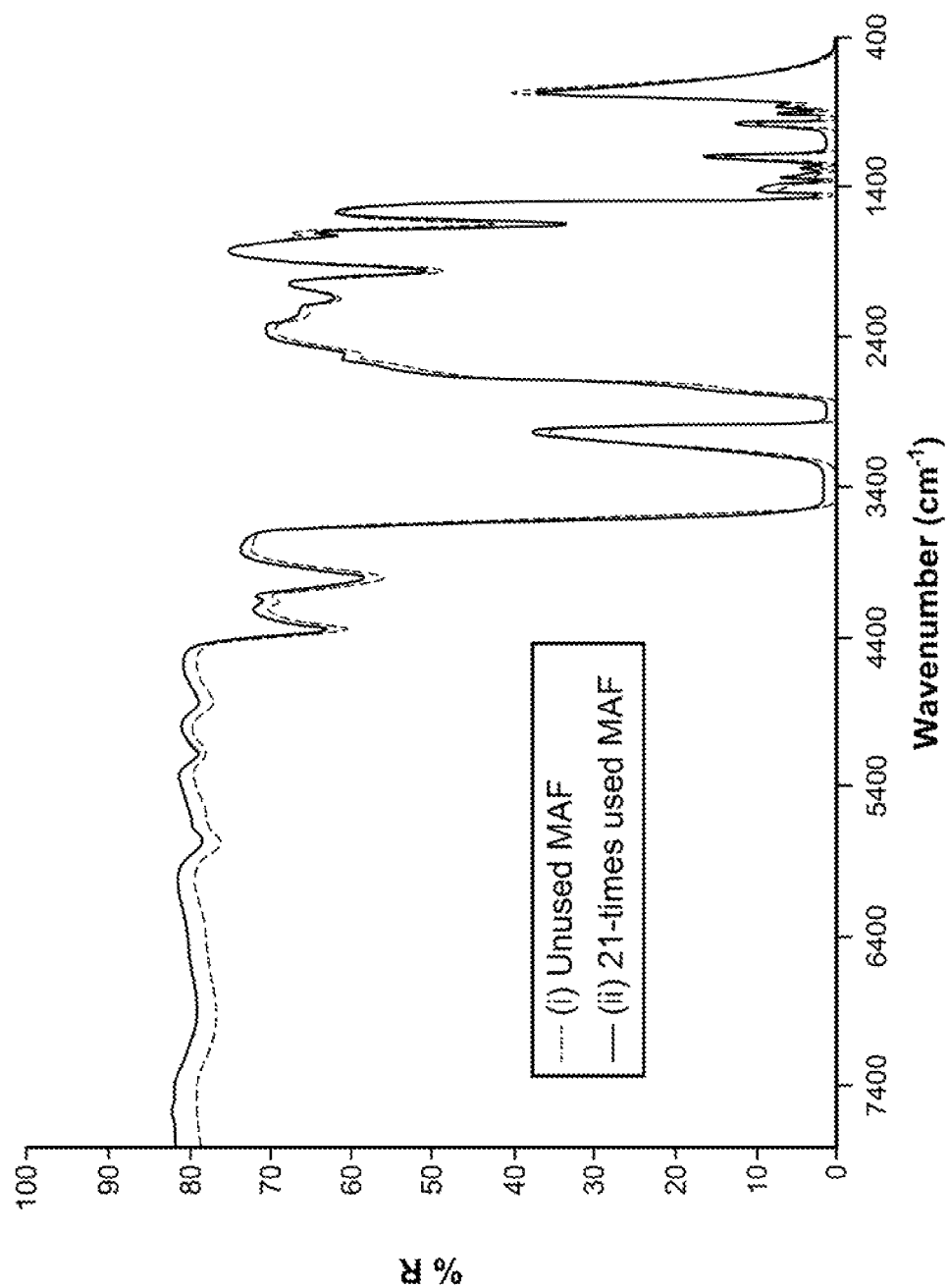
FIG. 13 shows the FTIR spectra of an unfiltered MAF according to the invention, (i) before microwave irradiation, and (ii) after 21 microwave irradiation cycles.

FIG. 13 shows the FTIR spectra of (i) Unused MAF prepared according to Example 2. The spectrum of the unused MAF was nearly identical to that of PEG, $M_n$ 200 to 415, which was the main component of the MAF. (ii) Used MAF prepared according to Example 2, and put through 21 microwave runs as described in Example 4. The MAF was not filtered during the runs. The spectra of the Unused MAF and the Used MAF were nearly identical. Thus, after 21 uses, the MAF was essentially free of degradation products.

Figure 14B:
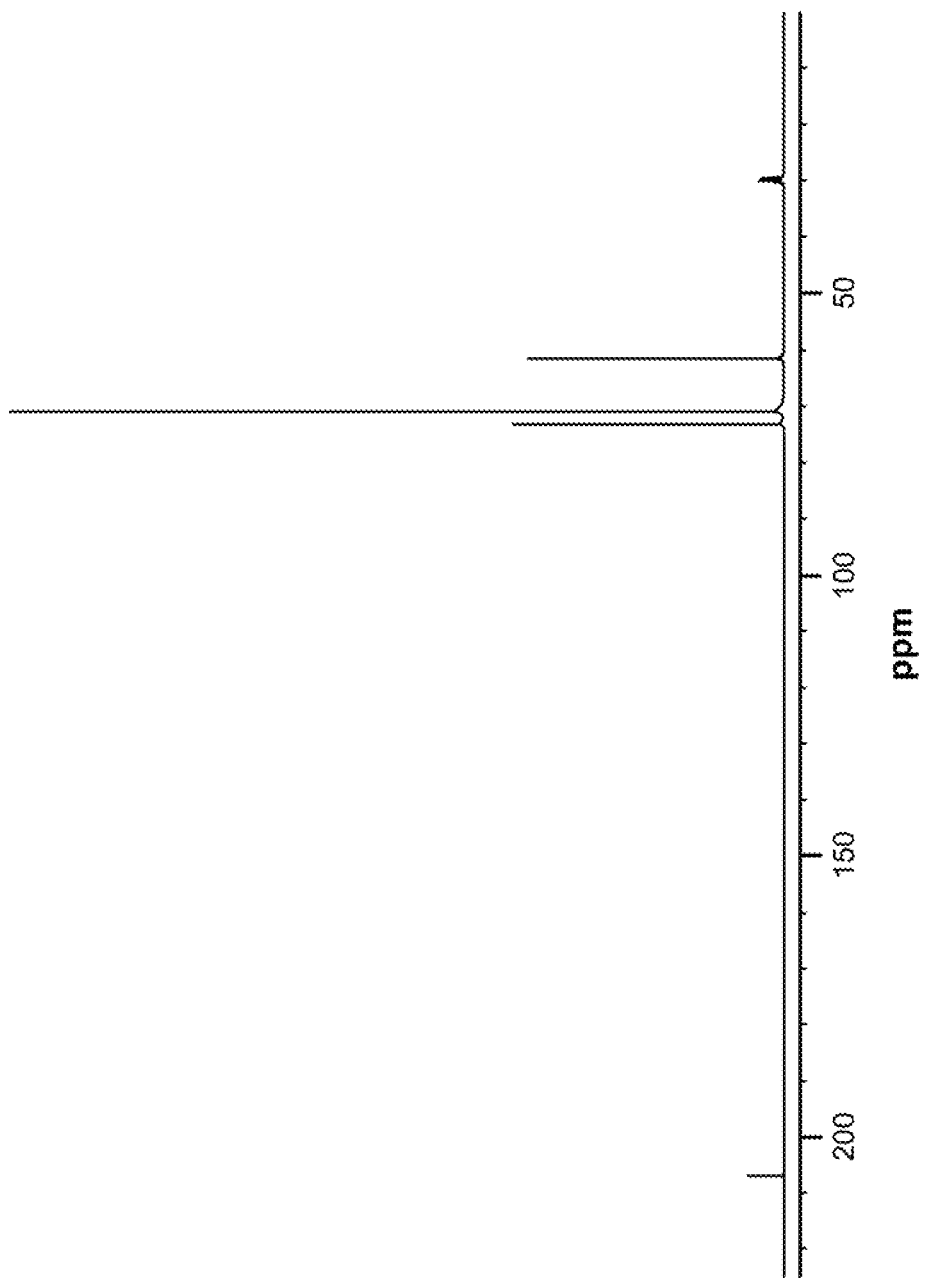
FIG. 14(b) shows a $^{13}C$ NMR spectrum for pure PEG.
Figure 14C:
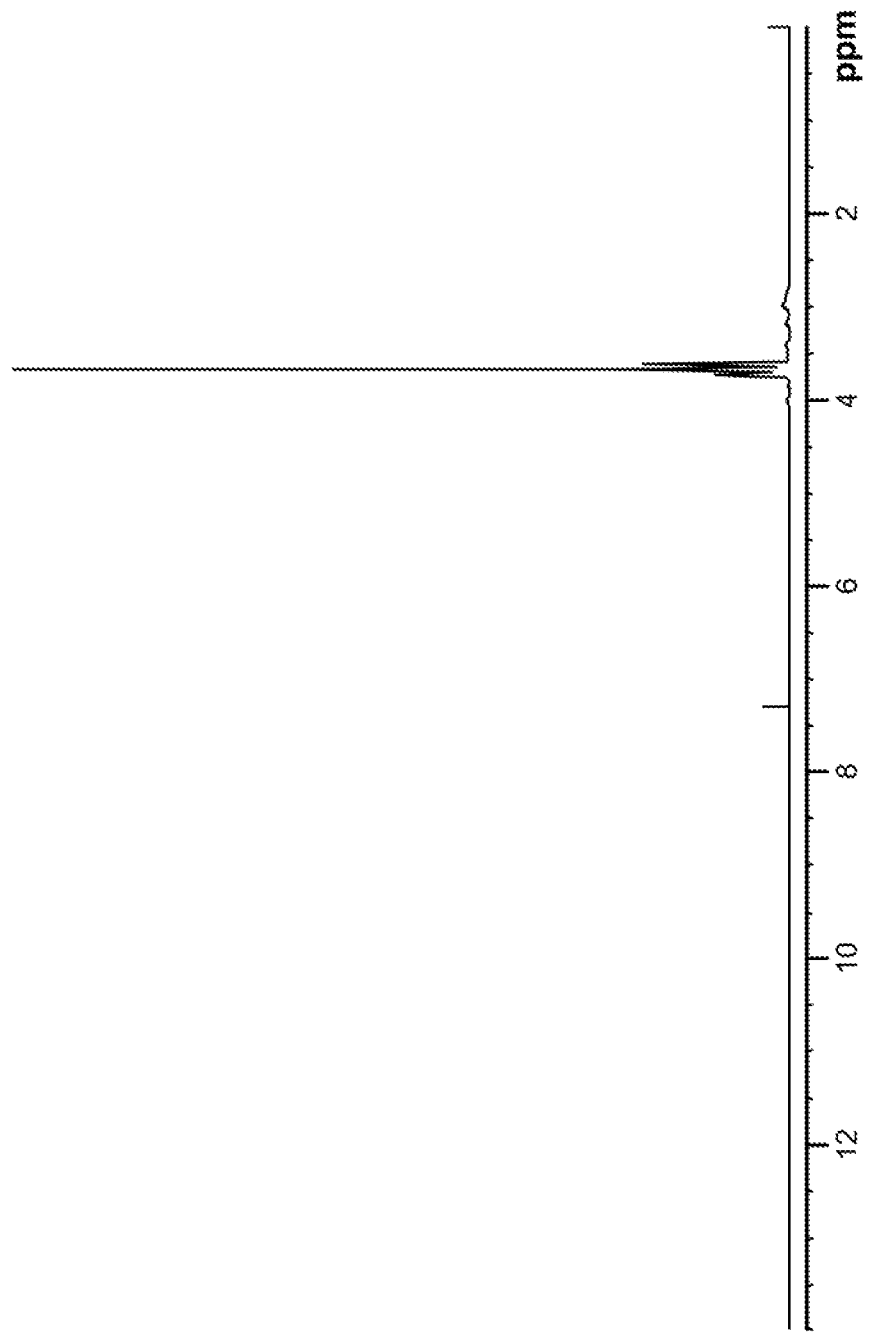
FIG. 14(c) shows a proton spectrum for an unfiltered MAF according to the invention, after 21 microwave cycles.
Figure 14D:
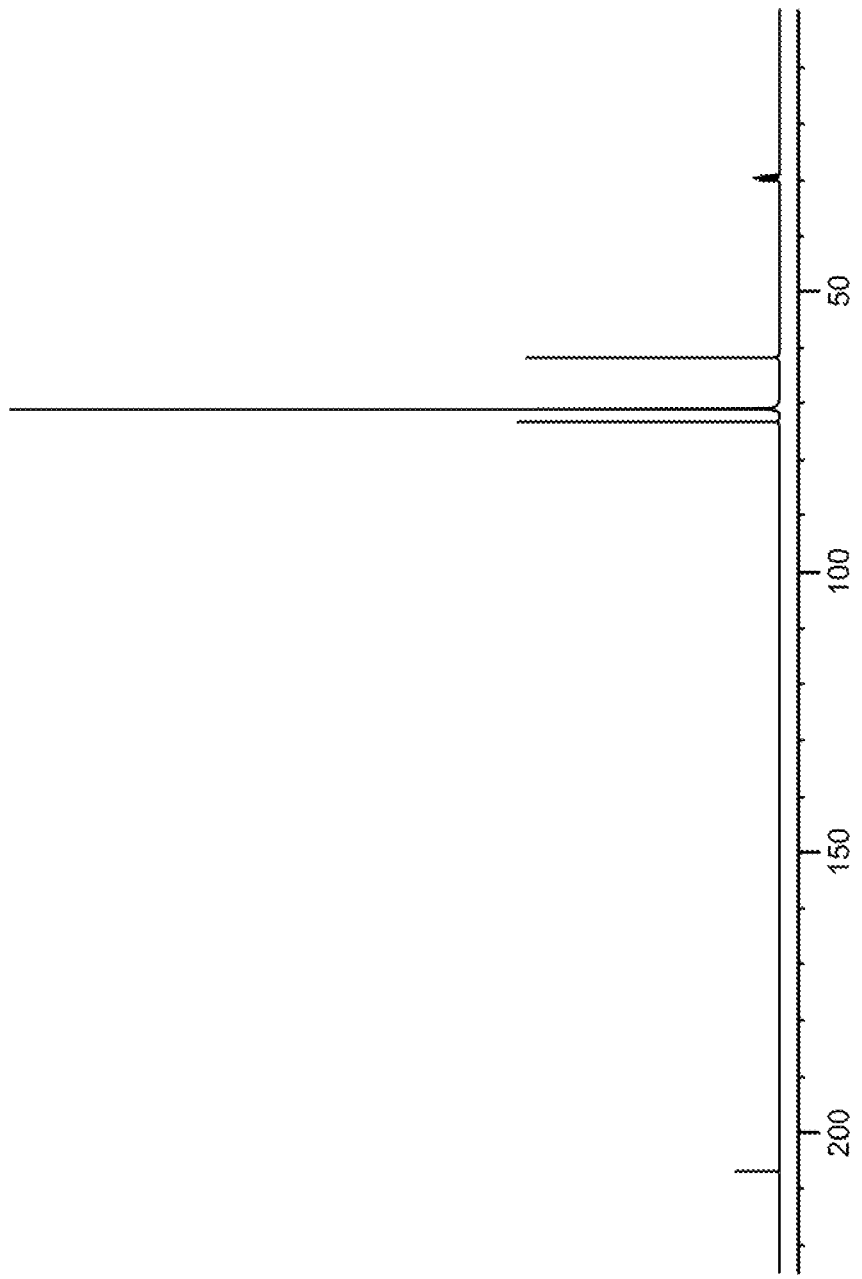
FIG. 14(d) shows a $^{13}C$ NMR spectrum for an unfiltered MAF according to the invention, after 21 microwave cycles. Samples were diluted with chloroform-d for the $^{1}H$ NMR and acetone-d6 for the $^{13}C$ NMR.

FIG. 14(a) shows a proton spectrum for pure PEG. FIG. 14(b) shows a $^{13}C$ NMR spectrum for pure PEG. FIG. 14(c) shows a proton spectrum for an unfiltered MAF according to the invention, after 21 microwave cycles. FIG. 14(d) shows a $^{13}C$ NMR spectrum for an unfiltered MAF according to the invention, after 21 microwave cycles. Samples were diluted with chloroform-d for the $^1H$ NMR and acetone-d6 for the $^{13}C$ NMR. In the proton spectra, the only other significant peaks are centered at 3.65 ppm. There are three types of H present: —O—$CH_2$—$CH_2$—O— (triplets, ethers, 3.0-4.0 ppm), HO—$CH_2\overline{\phantom{-}}$ (singlet, alcohols, 0.5-5.5 ppm) and HO—$\overline{C}H_2$—$CH_2$—O— (triplets, alcohols, 3.0-4.0 ppm). This is consistent with PEG. The peaks of the pure PEG and the Used MAF spectra are nearly identical. Some slight differences between the spectra can be attributed to sample preparation (dilution accuracies) for the NMR analysis. Thus, the pure PEG and the Used MAF spectra are identical, indicating no observable degradation products. Although the spectra of PEG decomposition products such as tetraethylene glycol are somewhat similar, they have distinctive features which are not seen in the Used MAF spectrum. Decomposition products such as saturated alkanes would show up in the 0-2 ppm range and vinyls would present in the 6-7 range. Any decomposition product from PVC again would present outside of the 3-4 ppm range. PACs would show up as aromatics in the 6.0-8.0 ppm range. None of these peaks are present in the Used MAF spectra, indicating that none of these decomposition products were produced.

In the case of the $^{13}C$ NMR spectra, C—O carbons resonate in the 50-70 ppm shift range. All carbons in PEG are C—O carbons, so the only peaks for PEG are in this range. The pure PEG and the Used MAF spectra both have three peaks in the 60-70 ppm range. These spectra are nearly identical.

Most of the proposed thermal degradation products (from Table 6) would appear as peaks outside of the 60-70 ppm region of PEG peaks. Aromatics, aldehydes, esters, and alkanes would appear above 100 ppm. No unidentified peaks were present in this range, once again indicating no decomposition products formed in the used MAF.

Figure 15A:
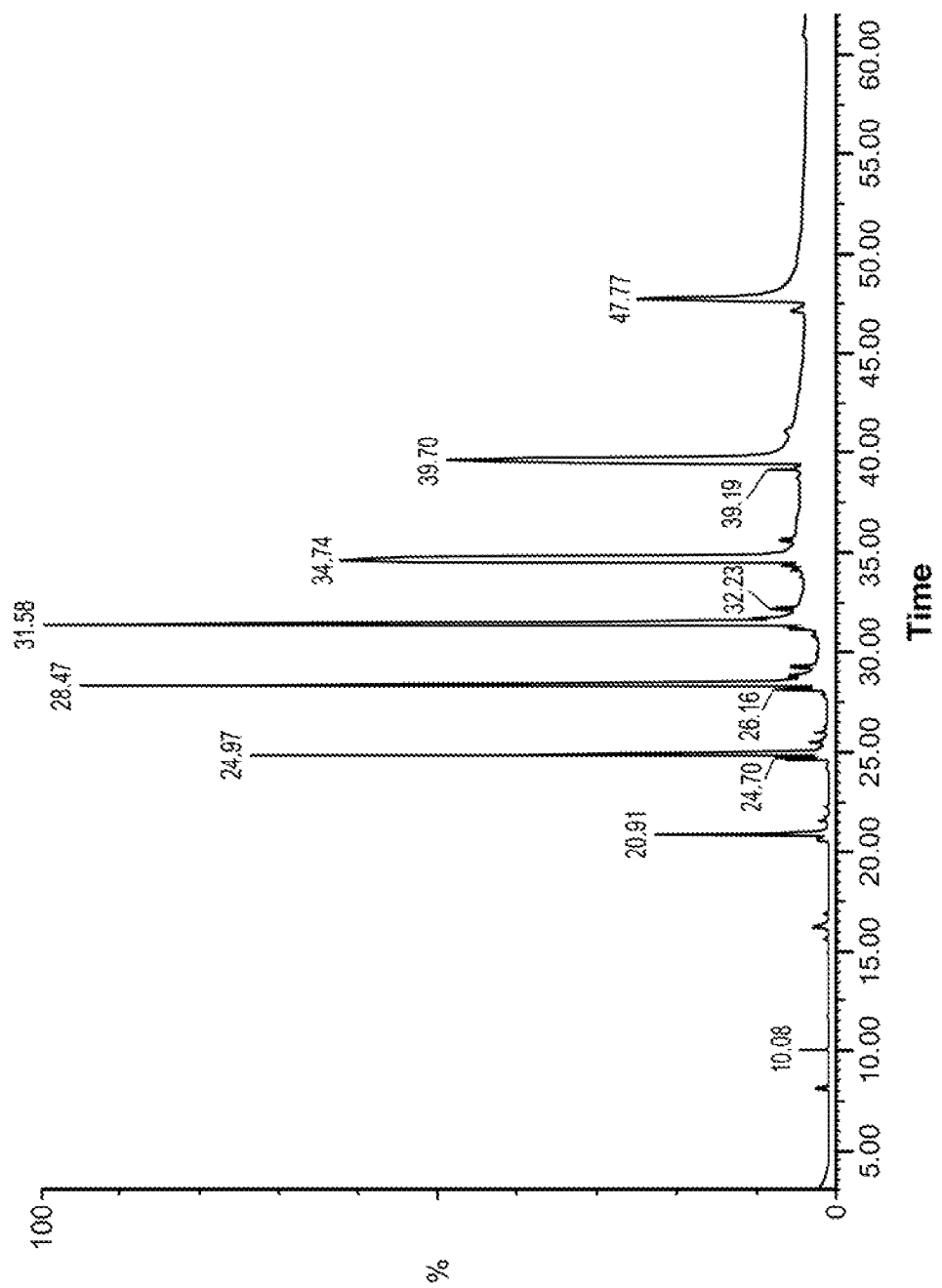
FIG. 15(a) shows the Total Ion Current (TIC) chromatogram from a representative GC-MS spectrum for an MAF according to the invention after 21 microwave irradiation cycles, giving elution times in minutes. This chromatogram was identical to that for pure poly(ethylene glycol) (PEG). For each of the observed chromatogram elution peaks, electron ionization (EI) mass spectra were obtained. These again corresponded to molecules expected from the EI mass spectra of PEG, and nothing else. A detailed analysis showed that these mass spectra products were just pyrolysis products of PEG, an artifact of the GC-MS technique, where the sample is ionized in a vacuum and then subject to high effective temperatures. The retention times of the elution peaks in the TIC chromatogram, and the corresponding compound (molecule), were: (16.25 min, 2,2'-oxybis-ethanol); (20.91 min, triethylene glycol); (24.97 min, 2,2'-[oxybis(2,1-ethanediyloxy)bis-ethanol]); (28.47 min, 18-crown-6-ether); 31.58 min, 18-crown-6-ether); (34.74 min, 18-crown-6-ether); (39.70 min, 18-crown-6-ether); (47.77 min, 18-crown-6-ether).
Figure 15B:
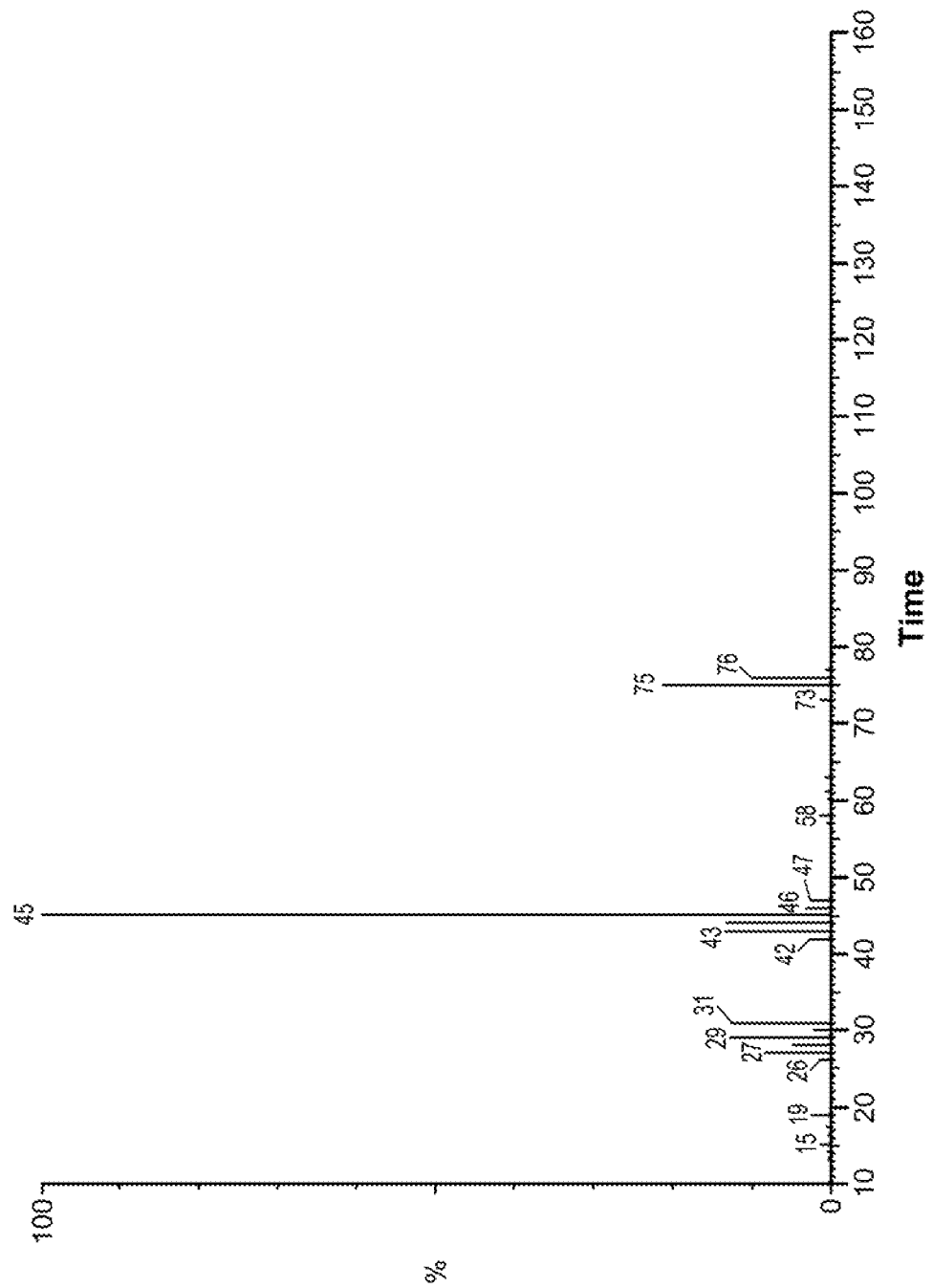
FIG. 15(b) shows the mass spectrum for one of the pyrolysis products, 2,2'-oxybis-ethanol, corresponding to the elution time of 16.25 min in the TIC chromatogram of FIG. 15(a).

FIG. 15(a) is a the chromatogram portion of a representative GC-MS spectrum for an MAF according to the invention after 21 microwave irradiation cycles, and gives elution times in minutes). FIG. 15(b) shows the mass spectrum for one of the pyrolysis products, 2,2'-oxybis-ethanol, corresponding to the elution time of 16.25 min in the TIC chromatogram of FIG. 15(a).

A detailed analysis showed that the products were just pyrolysis products of PEG, an artifact of the GC-MS technique, where the sample is ionized in a vacuum and then subject to high effective temperatures.

The conclusion from the comparative data in Table 6 and FIGS. 13-15 is that there is no trace of any hazardous or toxic decomposition products from microwave runs utilizing the present compositions and methods, and certainly nothing resembling the products typically found in the many studies of "low-temperature" pyrolysis and combustion of the components of the MAF and the components of the medical wastes, such as anthracene and poly-aromatic hydrocarbons (PAHs) (as summarized in Table 6). This applies to degradation products from both the MAF and the medical wastes.

One feature of nearly all the literature studies presented in Table 6 is that even when they refer to "low temperatures", the temperatures, typically are at least 300° C., which are higher than temperatures contemplated using the compositions and methods described herein. For example, Lattimer's "low-temperature" pyrolysis study of PEG actually describes pyrolysis under Argon ion flow at temperatures of 150° C. to 325° C. Other studies typically use even higher temperatures, of 500° C. to up to 1500° C. These higher temperatures facilitate a more, not less, advantageous comparison with the present compositions and methods. For if it is shown that the products observed from thermal degradation of the relevant materials at much higher temperatures are not observed with the much lower temperatures of the present invention, then this establishes that the much lower temperatures of the present invention could not produce any toxic or hazardous substances.

It will be appreciated by those skilled in the art that the present invention may be practiced in various alternate forms and configurations. The previously detailed descriptions of the disclosed compositions and methods are presented for clarity of understanding only, and no unnecessary limitations should be implied therefrom.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method for preparing a microwave active liquid composition for medical waste remediation, the method comprising the steps of:
(a) mixing a sol-stabilizing agent into a microwave active liquid having a boiling point from about 150° C. to about 300° C., while maintaining the temperature during mixing at about 100° C. to about 150° C. to form a solution;

(b) cooling the solution of (a) to less than about 30° C. to form a first gel comprising the microwave active liquid;

(c) adding a microwave enhancer to the first gel of (b) under conditions sufficient to form a sol;

(d) cooling the sol of (c) to at least 30° C. for a time sufficient for any unincorporated microwave enhancer to separate from said sol;

(e) irradiating the sol after the cooling of step (d) under conditions sufficient to heat the sol to at least about 150° C.;

(f) cooling the sol after the irradiation of step (e) to at least about 100° C.;

(g) optionally repeating steps (e) and (f) at least one time;

(h) irradiating the sol after the cooling of step (f) or (g) under conditions sufficient to heat the sol to at least about 150° C.;

(i) cooling the sol after the irradiation of step (h) to less than about 30° C. to form a second gel; and (j) isolating the second gel formed in (i) to yield the microwave active liquid composition for medical waste remediation.

2. The method of claim 1, wherein the sol in steps (e) and (h) is irradiated under conditions sufficient to heat the sol to between about 150° C. to about 300° C.

3. The method of claim 1, wherein the sol in step (f) is cooled to about 50° C. to about 100° C.

4. The method of claim 1, wherein the microwave active liquid is water soluble.

5. The method of claim 1, wherein the microwave active liquid comprises a poly(glycol), glycerol monostearate, glycerol lactate, glycerol acid esters, or combinations thereof.

6. The method of claim 5, wherein the poly(glycol) comprises poly(ethylene glycol), poly(propylene glycol), or combinations thereof.

7. The method of claim 1, wherein the microwave active liquid is poly(ethylene glycol).

8. The method of claim 7, wherein the poly(ethylene glycol) has an average molecular weight, $M_n$, from about 200 to about 420.

9. The method of claim 1, wherein the sol-stabilizing agent is poly(ethylene oxide).

10. The method of claim 1, wherein the microwave enhancer comprises activated carbon, SiC, $Fe_3O_4$, or combinations thereof.

* * * * *